US008415308B2

(12) United States Patent  
Cho et al.

(10) Patent No.: US 8,415,308 B2  
(45) Date of Patent: Apr. 9, 2013

(54) 1'-SUBSTITUTED-CARBA-NUCLEOSIDE PRODRUGS FOR ANTIVIRAL TREATMENT

(75) Inventors: Aesop Cho, Mountain View, CA (US); Choung U. Kim, San Carlos, CA (US); Adrian S. Ray, Redwood City, CA (US); Lijun Zhang, Los Altos Hills, CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

(21) Appl. No.: 13/117,060

(22) Filed: May 26, 2011

(65) Prior Publication Data

US 2012/0020921 A1 Jan. 26, 2012

Related U.S. Application Data

(60) Provisional application No. 61/349,597, filed on May 28, 2010, provisional application No. 61/353,351, filed on Jun. 10, 2010, provisional application No. 61/366,041, filed on Jul. 20, 2010.

(51) Int. Cl.
| | |
|---|---|
| A01N 43/04 | (2006.01) |
| A61K 31/70 | (2006.01) |
| C07H 5/04 | (2006.01) |
| C07H 7/06 | (2006.01) |

(52) U.S. Cl. ............ 514/23; 536/18.7; 536/29.2; 536/55
(58) Field of Classification Search .................. None
See application file for complete search history.

(56) References Cited

U.S. PATENT DOCUMENTS

| | | | |
|---|---|---|---|
| 7,368,437 | B1 | 5/2008 | Bojack et al. |
| 7,973,013 | B2 | 7/2011 | Cho et al. |
| 7,994,139 | B2 | 8/2011 | Babu et al. |
| 8,008,264 | B2 | 8/2011 | Butler et al. |
| 8,012,941 | B2 | 9/2011 | Cho et al. |
| 8,119,607 | B2 | 2/2012 | Francom et al. |
| 2004/0006002 | A1 | 1/2004 | Sommadossi et al. |
| 2011/0070194 | A1 | 3/2011 | Cho et al. |
| 2011/0230654 | A1 | 9/2011 | Butler et al. |
| 2011/0293563 | A1 | 12/2011 | Butler et al. |

FOREIGN PATENT DOCUMENTS

| | | |
|---|---|---|
| WO | 00/56734 A1 | 9/2000 |
| WO | 01/32153 A2 | 5/2001 |
| WO | 01/60315 A2 | 8/2001 |
| WO | 02/18404 A3 | 3/2002 |
| WO | 02/32920 A2 | 4/2002 |
| WO | 02/057287 A2 | 7/2002 |
| WO | 02/057425 A2 | 7/2002 |
| WO | 03/100009 A2 | 12/2003 |
| WO | 2004/046331 A2 | 6/2004 |
| WO | 2008/089105 A2 | 7/2008 |
| WO | WO2008/005542 | * 10/2008 |
| WO | 2008/141079 A1 | 11/2008 |
| WO | 2009/132135 A1 | 10/2009 |
| WO | WO2009/132135 | * 10/2009 |
| WO | 2011/035231 A1 | 3/2011 |
| WO | 2011/035250 A1 | 3/2011 |

OTHER PUBLICATIONS

International Search Report in International Application No. PCT/US2011/038253, dated Jul. 29, 2011 (2 pages).
Di Bisceglie, A. M., et al., "The Unmet Challenges of Hepatitis C," Scientific American, Inc., pp. 80-85 (1999).
Gordon, C. P., et al., "Control of Hepatitis C: A Medicinal Chemistry Perspective," J. Med. Chem., vol. 48, No. 1, pp. 1-20 (2005).
Moradpour, D., et al., "Replication of Hepatitis C Virus," Nat. Rev. Micro., vol. 5, pp. 453-463 (2007).
Dymock, B. W., et al., "Novel Approaches to the Treatment of Hepatitis C Virus Infection," Antiviral Chemistry & Chemotherapy, vol. 11, No. 2, pp. 79-96 (2000).
Scott, L. J., et al., "Interferon-a-2b Plus Ribavirin," Drugs, vol. 62, No. 3, pp. 507-556 (2002).
De Francesco, R., et al., "Approaching a New Era for Hepatitis C Virus Therapy: Inhibitors of the NS3-4A Serine Protease and the NS5B RNA-dependent RNA Polymerase," Antiviral Research, vol. 58, No. 1, pp. 1-16 (2003).
McGuigan, C., et al., "Intracellular Delivery of Bioactive AZT Nucleotides by Aryl Phosphate Derivatives of AZT," J Med. Chem., vol. 36, No. 8, pp. 1048-1052 (1993).
Perrone, P., et al., "Application of the Phosphoramidate ProTide Approach to 4'-Azidouridine Confers Sub-micromolar Potency versus Hepatitis C Virus on an Inactive Nucleoside," J. Med. Chem., vol. 50, No. 8, pp. 1840-1849 (2007).
Gardelli, C., et al., "Phosphoramidate Prodrugs of 2'-C-Methylcytidine for Therapy of Hepatitis C Virus Infection," J Med. Chem., vol. 52, No. 17, pp. 5394-5407 (2009).
Nishimura, N., et al., "Synthesis of Pyrrolo[2,1-f][1,2,4]triazine C-nucleosides. Isosteres of Sangivamycin, Tubercidin, and Toyocamycin," Carbohydrate Research, vol. 331, No. 1, pp. 77-82 (2001).
Otter, B. A., et al., "Conformational Properties of Purine-like C-Nucleosides," Nucleosides & Nucleotides, vol. 15, No. 1-3, pp. 793-807 (1996).
Patil, S. A., et al., "4-Aza-7,9-Dideazaadenosine, a New Cytotoxic Synthetic C-Nucleoside Analogue of Adenosine," Tetrahedron Lett., vol. 35, No. 30, pp. 5339-5342 (1994).
Hayashi, M., et al., "C-Nucleosides 17. A Synthesis of 2-Substituted 7-(b-D-ribofuranosyl)pyrrolo[2,1-f]-1,2,4-triazines. A New Type of "Purine-like" C-Nucleoside," Heterocycles, vol. 34, No. 3, pp. 569-574 (1992).
Knutsen, L. J. S., et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc., Perkin Trans. 1, pp. 229-238 (1984).
Knutsen, L. J. S., et al., "Synthesis of Imidazo-fused Bridgehead-nitrogen 2'-Deoxyribo-C-nucleosides: Coupling-Elimination Reactions of 2,5-Anhydro-3,4,6-tri-O-benzoyl-D-allonic Acid," J. Chem. Soc., Perkin Trans. 1, pp. 621-630 (1985).

(Continued)

Primary Examiner — Traviss C McIntosh, III  
(74) Attorney, Agent, or Firm — Fitzpatrick, Cella, Harper & Scinto

(57) ABSTRACT

Provided are prodrugs of pyrrolo[1,2-f][1,2,4]triazin-7-yl nucleoside phosphates wherein the 1' position of the nucleoside sugar is substituted with CN. The compounds, compositions, and methods provided are useful for the treatment Hepatitis C infections.

22 Claims, No Drawings

OTHER PUBLICATIONS

Bojack, G., et al., "Design and Synthesis of Inhibitors of Adenosine and AMP Deaminases," Org. Lett., vol. 3, No. 6, pp. 839-842 (2001).

Dudfield, P. J., et al., "Synthesis of C-ribosyl imidazo[2,1-f][1,2,4]triazines as Inhibitors of Adenosine and AMP Deaminases," J. Chem. Soc., Perkin Trans. 1, pp. 2929-2936 (1999).

Ramasamy, K., et al., "Synthesis and Antitumor Activity of Certain 3-b-D-Ribofuranosyl-1,2,4-triazolo[3,4-f]-1,2,4-triazines Related to Formycin Prepared via Ring Closure of a 1,2,4-Triazine Precursor," J. Med. Chem., vol. 29, No. 11, pp. 2231-2235 (1986).

International Preliminary Report on Patentability and Written Opinion of the International Searching Authority in International Application No. PCT/US2011/038253, dated Dec. 4, 2012 (6 pages).

* cited by examiner

U.S. 8,415,308 B2

1'-SUBSTITUTED-CARBA-NUCLEOSIDE PRODRUGS FOR ANTIVIRAL TREATMENT

This application is filed under 35 U.S.C. 111(a) claiming the benefit under 35 U.S.C. 119(e) of U.S. Provisional Application No. 61/349,597, entitled "Compound Having Antiviral Properties", filed May 28, 2010, U.S. Provisional Application No. 61/353,351, entitled "1'-Substituted-Carba-Nucleoside Prodrugs For Antiviral Treatment", filed Jun. 10, 2010, and U.S. Provisional Application No. 61/366,041, entitled "1'-Substituted-Carba-Nucleoside Prodrugs For Antiviral Treatment", filed Jul. 20, 2010, which are all incorporated herein by reference in their entireties for all purposes.

FIELD OF THE INVENTION

The invention relates generally to compounds with antiviral activity, most particularly to prodrugs of inhibitors of hepatitis C virus RNA-dependent RNA polymerase.

BACKGROUND OF THE INVENTION

The hepatitis C virus (HCV) is a leading cause of chronic liver disease worldwide (Boyer, N. et al. J Hepatol. 32:98-112, 2000) and may lead to hepatic fibrosis, cirrhosis and hepatocellular carcinoma (Cale, P., *Gastroenterology Clin. Biol.* 2009, 33, 958). A significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., *J. Med. Chem.* 2005, 48, 1-20; Maradpour, D.; et al., *Nat. Rev. Micro.* 2007, 5(6), 453-463). A number of HCV treatments are reviewed by Dymock et al. in Antiviral Chemistry & Chemotherapy, 11:2; 79-95 (2000).

Currently, there are primarily two antiviral compounds, ribavirin, a nucleoside analog, and interferon-alpha (α) (IFN), which are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079 but additional treatments for HCV infections have not yet become available for patients. Therefore, drugs having improved antiviral and pharmacokinetic properties with enhanced activity against development of HCV resistance, improved oral bioavailability, greater efficacy, fewer undesirable side effects and extended effective half-life in vivo (De Francesco, R. et al. (2003) Antiviral Research 58:1-16) are urgently needed.

RNA-dependent RNA polymerase (RdRp) is one of the best studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Virol. 22:73-89). Biochemical targets such as NS5B are important in developing HCV therapies since HCV does not replicate in the laboratory and there are difficulties in developing cell-based assays and preclinical animal systems.

Inhibition of viral replication by nucleosides has been extensively studied (De Clercq, E. (2001) J. Clin. Virol. 22:73-89) including nucleosides that inhibit RdRp. Generally, the antiviral activity of these nucleosides are attributed to the conversion of the nucleosides to their nucleoside triphosphates (NTPs) which act as inhibitors of DNA and RNA polymerases or as chain terminators following incorporation into the lengthening viral DNA or RNA strand. However, many NTPs lack adequate specificity for viral polymerases compared to host polymerases and, as a result, cause substantial toxicity. This has led to efforts to modify the core structures of nucleosides to achieve higher selectivity but many of the structural modifications have simultaneously compromised NTP production in the cells (Yamanaka, Antimicrob. Agents Chemother. 1999: 190-193).

The poor conversion of the nucleoside to NTP can often be attributed to the inability of nucleoside kinases to convert the nucleoside to the nucleoside 5'-monophosphate (NMP). NMP prodrugs have been used to bypass poor nucleoside kinase activity (Schultz, Bioorg. Med. Chem. 2003, 11, 885). Among these prodrugs, NMP phosphoramidates have been reported to increase intracellular concentrations of NTP compared to the nucleoside alone (McGuigan, J. Med. Chem. 1993, 36, 1048-1052). However, these NMP prodrugs are substrates for esterases and phosphodiesterases in the blood and other body tissues which can cleave the prodrug to a charged molecule or to the nucleoside, respectively. The charged molecule is then impermeable to the target organ or cell and the nucleoside is poorly phosphorylated intracellularly.

The development of a highly effective, non-toxic NMP prodrug is largely an unpredictable trial and error exercise requiring the balancing of the stability of the NMP prodrug in blood with the ability of the prodrug to reach a target organ or cell, be absorbed or actively taken up by the target cell, being efficiently cleaved to the NMP intracellularly and subsequently converted to a NTP that is selective for inhibiting the viral polymerase (Perrone, *J. Med. Chem.* 2007, 50, 1840-49; Gardelli, *J. Med. Chem.* 2009, 52, 5394-5407). For the case of an orally effective RdRp inhibitor for treating HCV infection, the NMP prodrug would need to be chemically stable to the conditions of the upper intestinal tract, be efficiently absorbed from the intestinal tract, survive the many esterases of the intestinal cells and blood, be efficiently extracted by the hepatocytes, and be cleaved to the NMP and subsequently converted to a NTP in hepatocytes that is specific for inhibiting the HCV NS5B polymerase.

Certain ribosides of the nucleobases pyrrolo[1,2-f][1,2,4]triazine, imidazo[1,5-f][1,2,4]triazine, imidazo[1,2-f][1,2,4]triazine, and [1,2,4]triazolo[4,3-f][1,2,4]triazine have been disclosed in *Carbohydrate Research* 2001, 331(1), 77-82; *Nucleosides & Nucleotides* (1996), 15(1-3), 793-807; *Tetrahedron Letters* (1994), 35(30), 5339-42; *Heterocycles* (1992), 34(3), 569-74; *J. Chem. Soc. Perkin Trans.* 1 1985, 3, 621-30; *J. Chem. Soc. Perkin Trans.* 1 1984, 2, 229-38; WO 2000056734; *Organic Letters* (2001), 3(6), 839-842; *J. Chem. Soc. Perkin Trans.* 1 1999, 20, 2929-2936; and *J. Med. Chem.* 1986, 29(11), 2231-5. However, these compounds have not been disclosed as useful for the treatment of HCV. Babu, Y. S., WO2008/089105 and WO2008/141079, discloses ribosides of pyrrolo[1,2-f][1,2,4]triazine nucleobases with antiviral, anti-HCV, and anti-RdRp activity.

Butler, et al., WO2009132135, disclose 1' substituted ribosides and prodrugs comprising pyrrolo[1,2-f][1,2,4]triazine nucleobases which have anti-HCV and anti-RdRp activity but does not disclose species of the 3'-O-acylated derivatives of those ribosides or the expected properties of such derivatives.

SUMMARY OF THE INVENTION

Provided are compounds that inhibit hepatitis C virus. The invention also comprises compounds that inhibit viral nucleic acid polymerases, particularly HCV RNA-dependent RNA polymerase (RdRp), rather than cellular nucleic acid polymerases. The compounds are prodrugs of nucleoside monophosphates that, when administered to animals, are efficiently extracted by the liver and are intracellularly converted to nucleoside triphosphates. The instant compounds are surprisingly more effectively extracted by the liver and converted to nucleoside triphosphates than the compounds disclosed by Butler, et al., WO2009132135. The enhanced extraction by the liver thereby limits the exposure of the non-target tissue to the prodrugs and nucleoside monophosphates. Therefore, the compounds of the instant invention are particularly suited for treating HCV infections in humans and other animals.

In one embodiment, provided is a compound of Formula I:

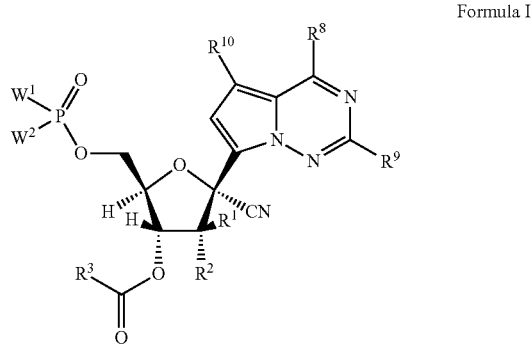

Formula I or a pharmaceutically acceptable salt or ester, thereof;

wherein:

$R^1$ is H, $(C_1-C_8)$alkyl, $(C_2-C_8)$alkenyl, or $(C_2-C_8)$alkynyl;

$R^2$ is OH or $-OC(O)R^3$;

each $R^3$ is independently H, $OR^4$, $NH(R^4)$, $N(R^4)_2$, $SR^4$, $(C_1-C_8)$alkyl, $(C_2-C_8)$alkenyl, $(C_2-C_8)$alkynyl, $(C_3-C_8)$ carbocyclyl, $(C_4-C_8)$ carbocyclylalkyl, aryl$(C_1-C_8)$alkyl, heterocyclyl$(C_1-C_8)$alkyl, aryl, heterocyclyl or heteroaryl;

each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

one of $W^1$ or $W^2$ is

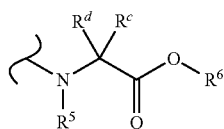

and the other of $W^1$ or $W^2$ is $OR^4$ or

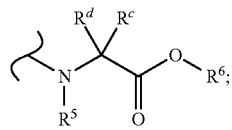

each $R^c$, $R^d$ or $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^8$ is halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NNHR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1-C_8)$alkyl, $(C_2-C_8)$alkenyl, $(C_2-C_8)$alkynyl, $(C_4-C_8)$carbocyclylalkyl, $(C_6-C_{20})$aryl, $(C_2-C_{20})$heterocyclyl, heteroaryl, $-C(=O)(C_1-C_8)$alkyl, $-S(O)_n(C_1-C_8)$alkyl, aryl$(C_1-C_8)$alkyl, $OR^{11}$ or $SR^{11}$;

each n is independently 0, 1, or 2;

each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, $-CH(=NR^{11})$, $-CH=NHNR^{11}$, $-CH=N(OR^{11})$, $-CH(OR^{11})_2$, $-C(=O)NR^{11}R^{12}$, $-C(=S)NR^{11}R^{12}$, $C(=O)OR^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, $-C(=O)(C_1-C_8)$alkyl, $-S(O)_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of $R^c$, $R^d$, $R^1$, $R^2$, $R^3$, $R^4$, $R^5$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

In another aspect, the present invention includes compounds of Formula I and pharmaceutically acceptable salts thereof and all racemates, enantiomers, diastereomers, tautomers, polymorphs, pseudopolymorphs and amorphous forms thereof.

In another aspect, the present invention provides novel compounds of Formula I with activity against infectious HCV viruses. Without wishing to be bound by theory, the compounds of the invention may inhibit viral RNA-dependent RNA polymerase and thus inhibit the replication of the virus. They are useful for treating human patients infected with a human virus such as hepatitis C.

In another aspect, the invention provides a pharmaceutical composition comprising an effective amount of a Formula I compound, or a pharmaceutically acceptable salt or ester thereof, in combination with a pharmaceutically acceptable diluent or carrier.

In another embodiment, the present application provides for combination pharmaceutical agent comprising:

a) a first pharmaceutical composition comprising a compound of Formula I; or a pharmaceutically acceptable salt, solvate, or ester thereof and b) a second pharmaceutical composition comprising at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof.

In another embodiment, the present application provides for a method of inhibiting HCV polymerase, comprising contacting a cell infected with HCV with an effective amount of a compound of Formula I; or a pharmaceutically acceptable salts, solvate, and/or ester thereof and at least one additional therapeutic agent.

In another embodiment, the present application provides for a method of treating HCV in a patient, comprising administering to said patient a therapeutically effective amount of a compound of Formula I; or a pharmaceutically acceptable salt, solvate, and/or ester thereof.

In another embodiment, the present application provides for a method of treating HCV in a patient, comprising administering to said patient a therapeutically effective amount of a compound of Formula I; or a pharmaceutically acceptable salt, solvate, and/or ester thereof; and at least one additional therapeutic agent.

Another aspect of the invention provides a method for the treatment or prevention of the symptoms or effects of an HCV infection in an infected animal which comprises administering to, i.e. treating, said animal with a pharmaceutical combination composition or formulation comprising an effective amount of a Formula I compound, and a second compound having anti-HCV properties.

In another aspect, the invention also provides a method of inhibiting HCV, comprising administering to a mammal infected with HCV an amount of a Formula I compound, effective to inhibit the replication of HCV in infected cells in said mammal.

In another aspect, the invention also provides processes and novel intermediates disclosed herein which are useful for preparing Formula I compounds of the invention.

In other aspects, novel methods for synthesis, analysis, separation, isolation, purification, characterization, and testing of the compounds of this invention are provided.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In another embodiment, compounds of Formula I are represented by Formula II:

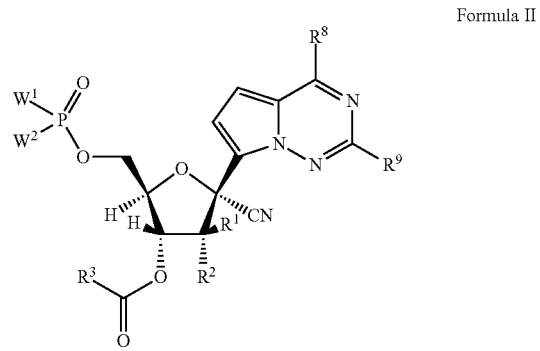

Formula II or a pharmaceutically acceptable salt or ester, thereof; wherein:
$R^1$ is H, $(C_1-C_8)$alkyl, $(C_2-C_8)$alkenyl, or $(C_2-C_8)$alkynyl;
$R^2$ is OH or $-OC(O)R^3$;
each $R^3$ is independently H, $OR^4$, $NH(R^4)$, $N(R^4)_2$, $SR^4$, $(C_1-C_8)$alkyl, $(C_2-C_8)$alkenyl, $(C_2-C_8)$alkynyl, $(C_3-C_8)$carbocyclyl, $(C_4-C_8)$ carbocyclylalkyl, aryl$(C_1-C_8)$alkyl, heterocyclyl$(C_1-C_8)$alkyl, aryl, heterocyclyl or heteroaryl;
each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;
one of $W^1$ or $W^2$ is

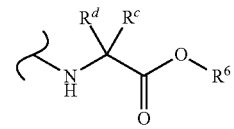

and the other of $W^1$ or $W^2$ is $OR^4$ or

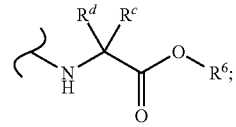

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;
each $R^8$ is halogen, $NR^{11}R^{12}$, $N(R^{11})OR^{11}$, $NR^{11}NR^{11}R^{12}$, $N_3$, $-S(O)_n(C_1-C_8)$alkyl, $OR^{11}$ or $SR^{11}$;
each n is independently 0, 1, or 2;
each $R^9$ is independently H, halogen, $NR^{11}R^{12}$, $N(R^{11})OR^{11}$, $NR^{11}NR^{11}R^{12}$, $N_3$, $OR^{11}$ or $SR^{11}$;
each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, $-C(=O)(C_1-C_8)$alkyl, $-S(O)_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of $R^c$, $R^d$, $R^1$, $R^2$, $R^3$, $R^4$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

In one embodiment of Formula II, $R^1$ is H. In another embodiment of Formula II, $R^1$ is $(C_1-C_8)$alkyl. In another embodiment of Formula II, $R^1$ is methyl. In another embodiment of Formula II, $R^1$ is $(C_2-C_8)$alkenyl. In another embodiment of Formula II, $R^1$ is ethenyl. In another embodiment of Formula II, $R^1$ is $(C_2-C_8)$alkynyl. In another embodiment of Formula II, $R^1$ is ethynyl.

In one embodiment of Formula II, $R^2$ is OH. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_2-C_8)$alkenyl. In another aspect of this embodiment, $R^1$ is ethenyl. In another aspect of this embodiment, $R^1$ is $(C_2-C_8)$alkynyl. In another aspect of this embodiment, $R^1$ is ethynyl.

In one embodiment of Formula II, $R^2$ is —$OC(O)R^3$. In another aspect of this embodiment, $R^1$ is H.

In one embodiment of Formula II, each $R^3$ is independently H, $OR^4$, $NH(R^4)$, $N(R^4)_2$ or $SR^4$.

In one embodiment of Formula II, each $R^3$ is independently $(C_1-C_8)$alkyl, $(C_2-C_8)$alkenyl, $(C_2-C_8)$alkynyl, $(C_3-C_8)$carbocyclyl, $(C_4-C_8)$ carbocyclylalkyl, aryl$(C_1-C_8)$alkyl, heterocyclyl$(C_1-C_8)$alkyl, aryl, heterocyclyl or heteroaryl. In another aspect of this embodiment, each $R^3$ is independently $(C_1-C_8)$alkyl. In another aspect of this embodiment, each $R^3$ is independently $(C_1-C_8)$alkyl wherein said $(C_1-C_8)$alkyl is optionally substituted with $NH_2$. In another aspect of this embodiment, each $R^3$ and $R^1$ are independently $(C_1-C_8)$alkyl. In another aspect of this embodiment, each $R^3$ is independently $(C_1-C_8)$alkyl and $R^1$ is methyl. In another aspect of this embodiment, $R^3$ is $(C_1-C_8)$alkyl, $R^1$ is methyl and $R^2$ is OH. In another aspect of this embodiment, each $R^3$ is independently $(C_1-C_8)$alkyl, $R^1$ is H and $R^2$ is —$OC(O)R^3$.

In one embodiment of Formula II, each $W^1$ and $W^2$ is independently

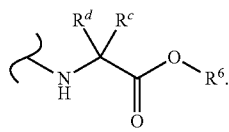

In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

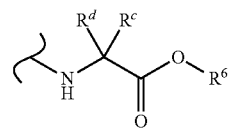

comprises a nitrogen-linked naturally occurring α-amino acid ester.

In another embodiment of Formula II, each $W^1$ and $W^2$ is independently

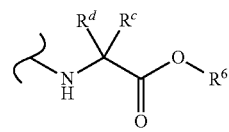

and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl. In another aspect of this embodiment, each $R^6$ is independently $(C_1-C_8)$alkyl. In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

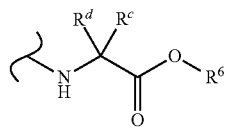

comprises a nitrogen-linked naturally occurring α-amino acid ester.

In one embodiment of Formula II, each $W^1$ and $W^2$ is independently

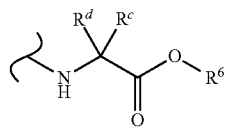

and each $R^6$ is independently $(C_1-C_8)$alkyl. In another aspect of this embodiment, each $R^6$ is independently secondary alkyl. In another aspect of this embodiment, each $R^6$ is 2-propyl. In another aspect of this embodiment, each $R^c$ is H and each $R^d$ is methyl. In another aspect of this embodiment, each $R^c$ is H and each $R^d$ is methyl wherein the chirality of the carbon to which said $R^c$ and $R^d$ is attached is S. In another aspect of this embodiment, each $R^c$ is H and each $R^d$ is methyl wherein the chirality of the carbon to which said $R^c$ and $R^d$ is attached is R. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, each

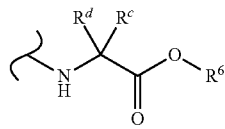

comprises a nitrogen-linked naturally occurring α-amino acid ester.

In one embodiment of Formula II, one of $W^1$ or $W^2$ is $OR^4$ and the other of $W^1$ or $W^2$ is

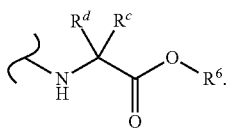

In another aspect of this embodiment, $R^4$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, $R^4$ is $(C_6-C_{20})$aryl, $(C_2-C_{20})$heterocyclyl or heteroaryl. In another aspect of this embodiment, $R^4$ is $(C_6-C_{20})$aryl. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, each

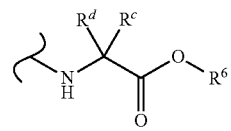

comprises a nitrogen-linked naturally occurring α-amino acid ester.

In one embodiment of Formula II, one of $W^1$ or $W^2$ is $OR^4$ and the other of $W^1$ or $W^2$ is

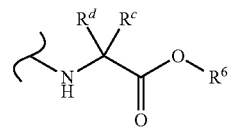

wherein $R^4$ is unsubstituted phenyl. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is $(C_1-C_8)$alkyl. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

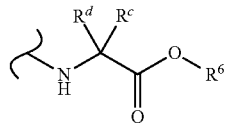

comprises a nitrogen-linked naturally occurring α-amino acid ester.

In one embodiment of Formula II, one of $W^1$ or $W^2$ is $OR^4$ and the other of W or $W^2$ is

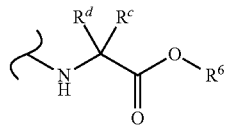

wherein one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^c$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, the chirality at phosphorus is S. In another aspect of this embodiment, the chirality at phosphorus is R. In another aspect of this embodiment, each

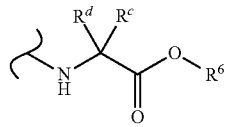

comprises a nitrogen-linked naturally occurring α-amino acid ester.

In one embodiment of Formula II, one of $W^1$ or $W^2$ is $OR^4$ and the other of $W^1$ or $W^2$ is

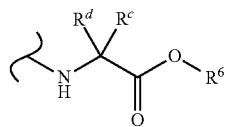

wherein $R^4$ is unsubstituted phenyl, one of $R^c$ or $R^d$ is H and the other of $R^c$ or $R^d$ is methyl. In another aspect of this embodiment, the chirality at phosphorous is R. In another aspect of this embodiment, the chirality at phosphorous is S. In another aspect of this embodiment, the chirality of the carbon to which said $R^c$ and $R^d$ is attached is S. In another aspect of this embodiment, the chirality of the carbon to which said $R^c$ and $R^d$ is attached is S and the chirality at phosphorus is S. In another aspect of this embodiment, the chirality of the carbon to which said $R^c$ and $R^d$ is attached is S and the chirality at phosphorus is R. In another aspect of this embodiment, the chirality of the carbon to which said $R^c$ and $R^d$ is attached is R. In another aspect of this embodiment, the chirality of the carbon to which said $R^c$ and $R^d$ is attached is R and the chirality at phosphorus is S. In another aspect of this embodiment, the chirality of the carbon to which said $R^c$ and $R^d$ is attached is R and the chirality at phosphorus is R. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, each

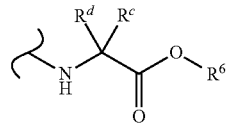

comprises a nitrogen-linked naturally occurring α-amino acid ester.

In one embodiment of Formula II, one of $W^1$ or $W^2$ is $OR^4$ and the other of $W^1$ or $W^2$ is

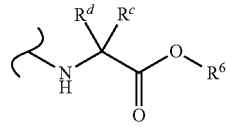

wherein $R^4$ is unsubstituted phenyl and $R^6$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl. In another aspect of this embodiment, $R^6$ is $(C_1-C_8)$alkyl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is $(C_1-C_8)$alkyl. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

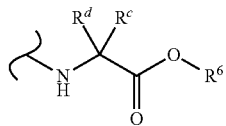

comprises a nitrogen-linked naturally occurring α-amino acid ester.

In one embodiment of Formula II, one of $W^1$ or $W^2$ is $OR^4$ and the other of $W^1$ or $W^2$ is

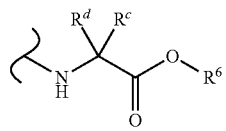

wherein one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$ alkyl. In another aspect of this embodiment, the chirality at phosphorus is S. In another aspect of this embodiment, the chirality at phosphorus is R. In another aspect of this embodiment, each

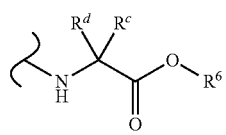

comprises a nitrogen-linked naturally occurring α-amino acid ester.

In one embodiment of Formula II, one of $W^1$ or $W^2$ is $OR^4$ and the other of $W^1$ or $W^2$ is

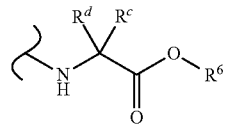

wherein $R^4$ is unsubstituted phenyl, one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$ alkyl. In another aspect of this embodiment, the chirality at phosphorus is S. In another aspect of this embodiment, the chirality at phosphorus is R. In another aspect of this embodiment, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH. In another aspect of this embodiment, $R^9$ is $SR^{11}$. In another aspect of this embodiment, $R^9$ is SH. In another aspect of this embodiment, each

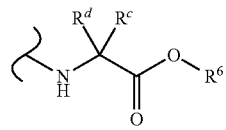

comprises a nitrogen-linked naturally occurring α-amino acid ester.

In another embodiment of Formula II, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$.

In another aspect of this embodiment, $R^9$ is OH. In another aspect of this embodiment, $R^9$ is $SR^{11}$. In another aspect of this embodiment, $R^9$ is SH.

In another embodiment of Formula II, $R^8$ is $NH_2$ and $R^9$ is H. In another aspect of this embodiment, $R^1$ is H. In another aspect of this embodiment, $R^1$ is $(C_1$-$C_8)$alkyl. In another aspect of this embodiment, $R^1$ is $(C_2$-$C_8)$alkenyl. In another aspect of this embodiment, $R^1$ is $(C_2$-$C_8)$alkynyl. In another aspect of this embodiment, $R^2$ is OH. In another aspect of this embodiment, $R^2$ is OH and $R^3$ is $(C_1$-$C_8)$alkyl. In another aspect of this embodiment, each $R^c$ is H and each $R^d$ is methyl. In another aspect of this embodiment, each $R^c$ is H and each $R^d$ is methyl wherein the chirality of the carbon to which each said $R^c$ and $R^d$ is attached is S. In another aspect of this embodiment, each $R^c$ is H and each $R^d$ is methyl wherein the chirality of the carbon to which each said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$.

In another embodiment of Formula II, $R^8$ is $NH_2$, $R^9$ is H and $R^1$ is $(C_1$-$C_8)$alkyl. In another aspect of this embodiment, $R^2$ is OH. In another aspect of this embodiment, $R^2$ is OH and $R^3$ is $(C_1$-$C_8)$alkyl. In another aspect of this embodiment, each $R^6$ is independently $(C_1$-$C_8)$alkyl. In another aspect of this embodiment, each $R^6$ is independently secondary alkyl. In another aspect of this embodiment, each $W^1$ and $W^2$ is independently

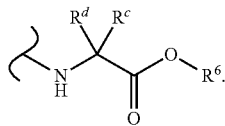

In another aspect of this embodiment, one of $W^1$ or $W^2$ is $OR^4$ and the other of $W^1$ or $W^2$ is

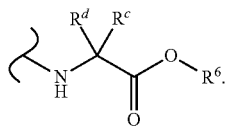

In another aspect of this embodiment, each

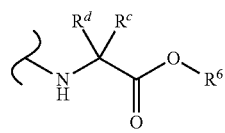

comprises a nitrogen-linked naturally occurring α-amino acid ester.

In another embodiment of Formula II, $R^8$ is $NH_2$, $R^9$ is H and one of $W^1$ or $W^2$ is $OR^4$ and the other of $W^1$ or $W^2$ is

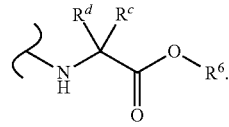

In another aspect of this embodiment, one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^c$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, the chirality at phosphorus is S. In another aspect of this embodiment, the chirality at phosphorus is R. In another aspect of this embodiment, each

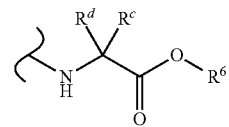

comprises a nitrogen-linked naturally occurring α-amino acid ester.

In another embodiment of Formula II, $R^8$ is $NH_2$, $R^9$ is H, $R^1$ is $(C_1$-$C_8)$alkyl and one of $W^1$ or $W^2$ is $OR^4$ and the other of $W^1$ or $W^2$ is

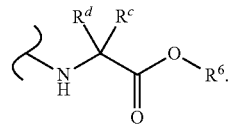

In another aspect of this embodiment, $R^2$ is OH. In another aspect of this embodiment, $R^2$ is OH and $R^3$ is $(C_1$-$C_8)$alkyl. In another aspect of this embodiment, $R^6$ is $(C_1$-$C_8)$alkyl. In another aspect of this embodiment, $R^6$ is secondary alkyl. In another aspect of this embodiment, one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^C$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, the chirality at phosphorus is S. In another aspect of this embodiment, the chirality at phosphorus is R. In another aspect of this embodiment, each

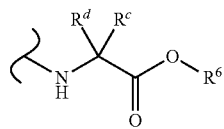

comprises a nitrogen-linked naturally occurring α-amino acid ester.

In another embodiment of Formula II, $R^8$ is $NH_2$ and $R^9$ is $NH_2$.

In another embodiment of Formula II, $R^8$ is OH and $R^9$ is $NH_2$.

In another embodiment of Formula II, $R^8$ is OH and $R^9$ is OH.

In another embodiment, compounds of Formula I are represented by Formula III:

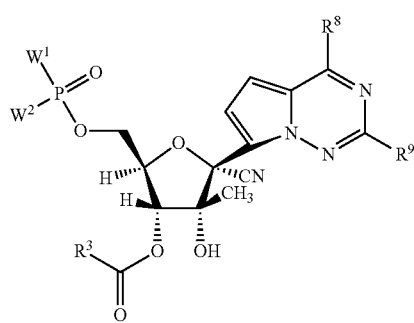

Formula III or a pharmaceutically acceptable salt or ester, thereof; wherein:

$R^3$ is $(C_1-C_8)$alkyl, $(C_2-C_8)$alkenyl, $(C_2-C_8)$alkynyl, $(C_3-C_8)$carbocyclyl, $(C_4-C_8)$ carbocyclylalkyl, aryl$(C_1-C_8)$alkyl, heterocyclyl$(C_1-C_8)$alkyl, aryl, heterocyclyl or heteroaryl;

each $R^a$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

one of $W^1$ or $W^2$ is

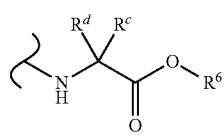

and the other of $W^1$ or $W^2$ is $OR^4$ or

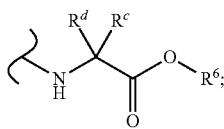

each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^4$ is $(C_6-C_{20})$aryl or heteroaryl;

each $R^8$ is halogen, $NR^{11}R^{12}$, $N(R^{11})OR^{11}$, $NR^{11}NR^{11}R^{12}$, $N_3$, $—S(O)_n(C_1-C_8)$alkyl, $OR^{11}$ or $SR^{11}$;

each n is independently 0, 1, or 2;

each $R^9$ is independently H halogen $NR^{11}R^{12}$, $N(R^{11})OR^{11}$, $NR^{11}NR^{11}R^{12}$, $N_3$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, $—C(=O)(C_1-C_8)$alkyl, $—S(O)_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $—O—$, $—S(O)_n—$ or $—NR^a—$; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of $R^c$, $R^d$, $R^3$, $R^4$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_n R^a$, $S(O)_2N(R^a)_2$, $S(O)_2NH(R^a)$, $S(O)_2NH_2$, $OR^a$ or $R^a$.

In one embodiment of Formula III, $R^3$ is $(C_1-C_8)$alkyl, $(C_2-C_8)$alkenyl, $(C_2-C_8)$alkynyl or $(C_3-C_8)$carbocyclyl. In another embodiment of Formula III, $R^3$ $(C_1-C_8)$alkyl. In embodiment of Formula III, $R^3$ is $(C_1-C_8)$alkyl wherein said $(C_1-C_8)$alkyl is optionally substituted with $NH_2$.

In one embodiment of Formula III, each $W^1$ and $W^2$ is independently

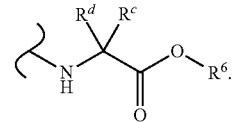

In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

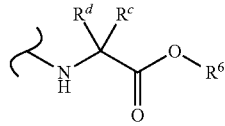

comprises a nitrogen-linked naturally occurring α-amino acid ester.

In another embodiment of Formula III, each $W^1$ and $W^2$ is independently

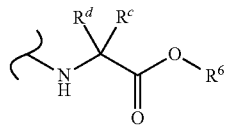

and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl. In another aspect of this embodiment, each $R^6$ is independently $(C_1-C_8)$alkyl. In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

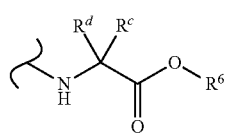

comprises a nitrogen-linked naturally occurring α-amino acid ester.

In one embodiment of Formula III, each $W^1$ and $W^2$ is independently

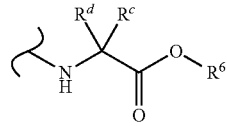

and each $R^6$ is independently $(C_1-C_8)$alkyl. In another aspect of this embodiment, each $R^6$ is independently secondary alkyl. In another aspect of this embodiment, each $R^6$ is 2-propyl. In another aspect of this embodiment, each $R^c$ is H and each $R^d$ is methyl. In another aspect of this embodiment, each $R^c$ is H and each $R^d$ is methyl wherein the chirality of the carbon to which said $R^c$ and $R^d$ is attached is S. In another aspect of this embodiment, each $R^c$ is H and each $R^d$ is methyl wherein the chirality of the carbon to which said $R^c$ and $R^d$ is attached is R. In another aspect of this embodiment, each

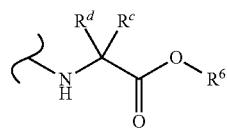

comprises a nitrogen-linked naturally occurring α-amino acid ester.

In one embodiment of Formula III, one of $W^1$ or $W^2$ is $OR^4$ and the other of $W^1$ or $W^2$ is

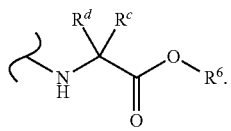

In another aspect of this embodiment, $R^4$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, $R^4$ is $(C_6-C_{20})$aryl, $(C_2-C_{20})$heterocyclyl or heteroaryl. In another aspect of this embodiment, $R^4$ is $(C_6-C_{20})$aryl. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, each

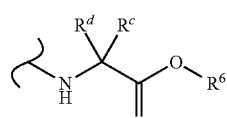

comprises a nitrogen-linked naturally occurring α-amino acid ester.

In one embodiment of Formula III, one of $W^1$ or $W^2$ is $OR^4$ and the other of $W^1$ or $W^2$ is

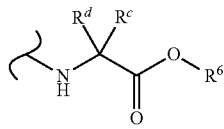

wherein $R^4$ is unsubstituted phenyl. In another aspect of this embodiment, $R^3$ is $(C_1-C_8)$alkyl. In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is $(C_1-C_8)$alkyl. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

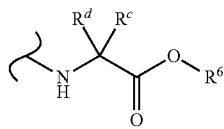

comprises a nitrogen-linked naturally occurring α-amino acid ester.

In one embodiment of Formula III, one of $W^1$ or $W^2$ is $OR^4$ and the other of $W^1$ or $W^2$ is

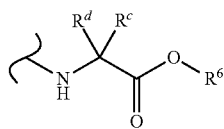

wherein one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^c$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2 NH(R^a)$, $S(O)_2NH_2$, $OR^a$ or $R^a$. In another aspect of this embodiment, $R^3$ is $(C_1-C_8)$alkyl. In another aspect of this embodiment, the chirality at phosphorus is S. In another aspect of this embodiment, the chirality at phosphorus is R. In another aspect of this embodiment, each

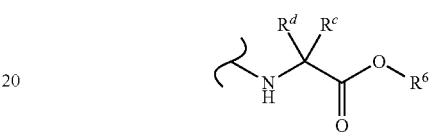

comprises a nitrogen-linked naturally occurring α-amino acid ester.

In one embodiment of Formula III, one of $W^1$ or $W^2$ is $OR^4$ and the other of $W^1$ or $W^2$ is

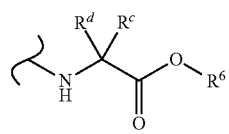

wherein $R^4$ is unsubstituted phenyl, one of $R^c$ or $R^d$ is H and the other of $R^c$ or $R^d$ is methyl. In another aspect of this embodiment, the chirality at phosphorous is R. In another aspect of this embodiment, the chirality at phosphorous is S. In another aspect of this embodiment, the chirality of the carbon to which said $R^c$ and $R^d$ is attached is S. In another aspect of this embodiment, the chirality of the carbon to which said $R^c$ and $R^d$ is attached is S and the chirality at phosphorus is S. In another aspect of this embodiment, the chirality of the carbon to which said $R^c$ and $R^d$ is attached is S and the chirality at phosphorus is R. In another aspect of this embodiment, the chirality of the carbon to which said $R^c$ and $R^d$ is attached is R. In another aspect of this embodiment, the chirality of the carbon to which said $R^c$ and $R^d$ is attached is R and the chirality at phosphorus is S. In another aspect of this embodiment, the chirality of the carbon to which said $R^c$ and $R^d$ is attached is R and the chirality at phosphorus is R. In another aspect of this embodiment, $R^3$ is $(C_1-C_8)$alkyl. In another aspect of this embodiment, each

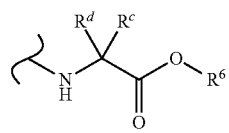

comprises a nitrogen-linked naturally occurring α-amino acid ester.

In one embodiment of Formula III, one of $W^1$ or $W^2$ is $OR^4$ and the other of $W^1$ or $W^2$ is

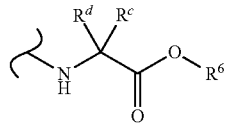

wherein $R^4$ is unsubstituted phenyl and $R^6$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl. In another aspect of this embodiment, $R^6$ is $(C_1-C_8)$alkyl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is $(C_1-C_8)$alkyl. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

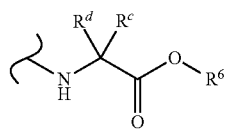

comprises a nitrogen-linked naturally occurring α-amino acid ester.

In one embodiment of Formula II, one of $W^1$ or $W^2$ is $OR^4$ and the other of $W^1$ or $W^2$ is

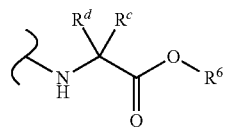

wherein one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2 NH(R^a)$, $S(O)_2NH_2$, $OR^a$ or $R^a$. In another aspect of this embodiment, $R^3$ is $(C_1-C_8)$alkyl. In another aspect of this embodiment, the chirality at phosphorus is S. In another aspect of this embodiment, the chirality at phosphorus is R. In another aspect of this embodiment, each

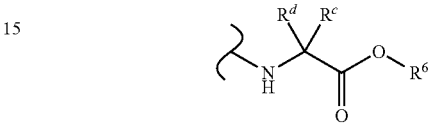

comprises a nitrogen-linked naturally occurring α-amino acid ester.

In one embodiment of Formula III, one of $W^1$ or $W^2$ is $OR^4$ and the other of $W^1$ or $W^2$ is

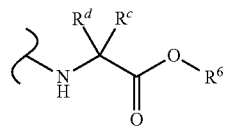

wherein $R^4$ is unsubstituted phenyl, one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^3$ is $(C_1-C_8)$alkyl. In another aspect of this embodiment, the chirality at phosphorus is S. In another aspect of this embodiment, the chirality at phosphorus is R. In another aspect of this embodiment, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH. In another aspect of this embodiment, $R^9$ is $SR^{11}$. In another aspect of this embodiment, $R^9$ is SH. In another aspect of this embodiment, each

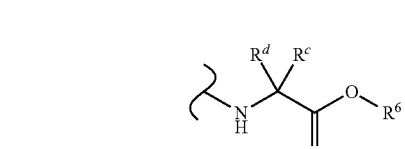

comprises a nitrogen-linked naturally occurring α-amino acid ester.

In another embodiment of Formula III, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$ or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH. In another aspect of this embodiment, $R^9$ is $SR^{11}$. In another aspect of this embodiment, $R^9$ is SH.

In another embodiment of Formula III, $R^8$ is $NH_2$ and $R^9$ is H. In another aspect of this embodiment, $R^3$ is $(C_1-C_8)$alkyl. In another aspect of this embodiment, each $R^c$ is H and each $R^d$ is methyl. In another aspect of this embodiment, each $R^c$ is H and each $R^d$ is methyl wherein the chirality of the carbon to which each said $R^c$ and $R^d$ is attached is S. In another aspect of this embodiment, each $R^c$ is H and each $R^d$ is methyl wherein the chirality of the carbon to which each said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, each $R^6$ is independently $(C_1-C_8)$alkyl. In another aspect of this embodiment, each $R^6$ is independently secondary alkyl. In another aspect of this embodiment, each $W^1$ and $W^2$ is independently

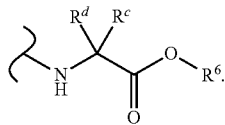

In another aspect of this embodiment, one of $W^1$ or $W^2$ is $OR^4$ and the other of $W^1$ or $W^2$ is

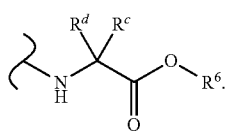

In another aspect of this embodiment, each

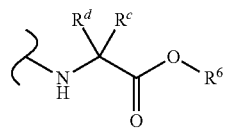

comprises a nitrogen-linked naturally occurring α-amino acid ester.

In another embodiment of Formula III, $R^8$ is $NH_2$, $R^9$ is H and one of $W^1$ or $W^2$ is $OR^4$ and the other of $W^1$ or $W^2$ is

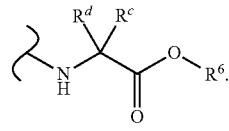

In another aspect of this embodiment, one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^c$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, the chirality at phosphorus is S. In another aspect of this embodiment, the chirality at phosphorus is R. In another aspect of this embodiment, each

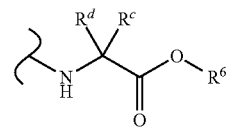

comprises a nitrogen-linked naturally occurring α-amino acid ester.

In another embodiment of Formula III, $R^8$ is $NH_2$ and $R^9$ is $NH_2$.

In another embodiment of Formula III, $R^8$ is OH and $R^9$ is $NH_2$.

In another embodiment of Formula III, $R^8$ is OH and $R^9$ is OH.

In another embodiment, compounds of Formula I are represented by Formula IV:

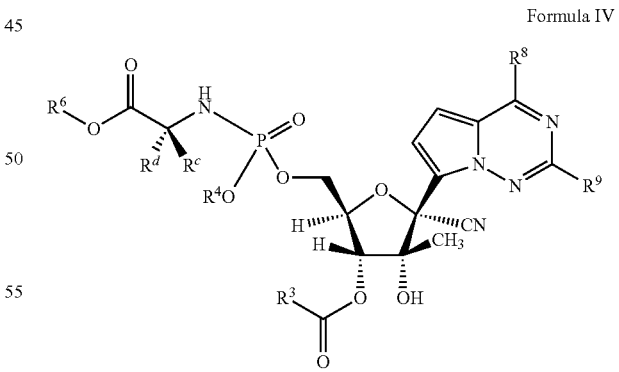

Formula IV or a pharmaceutically acceptable salt or ester, thereof; wherein:

$R^3$ is $(C_1-C_8)$alkyl, $(C_2-C_8)$alkenyl, $(C_2-C_8)$alkynyl, $(C_3-C_8)$carbocyclyl or $(C_4-C_8)$ carbocyclylalkyl;

each $R^a$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;

each $R^c$ or $R^d$ is independently H or methyl;

$R^4$ is $(C_6-C_{20})$aryl;

$R^6$ is $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl;

each $R^8$ is halogen, $NR^{11}R^{12}$, $N(R^{11})OR^{11}$, $NR^{11}NR^{11}R^{12}$, $N_3$, $-S(O)_n(C_1-C_8)$alkyl, $OR^{11}$ or $SR^{11}$;

each n is independently 0, 1, or 2;

each $R^9$ is independently H, halogen, $NR^{11}R^{12}$, $N(R^{11})OR^{11}$, $NR^{11}NR^{11}R^{12}$, $N_3$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, $-C(=O)(C_1-C_8)$alkyl, $-S(O)_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of $R^3$, $R^4$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

In one embodiment of Formula IV, $R^6$ is $(C_1-C_8)$alkyl. In another aspect of this embodiment, $R^3$ is $(C_1-C_8)$alkyl. In another aspect of this embodiment, $R^3$ is 2-propyl. In another aspect of this embodiment, $R^c$ is methyl and $R^d$ is H. In another aspect of this embodiment, $R^c$ is methyl, $R^d$ is H and the chirality at phosphorous is S. In another aspect of this embodiment, $R^c$ is methyl, $R^d$ is H and the chirality at phosphorous is R. In another aspect of this embodiment, $R^c$ is H and $R^d$ is methyl. In another aspect of this embodiment, $R^c$ is H, $R^d$ is methyl and the chirality at phosphorous is S. In another aspect of this embodiment, $R^c$ is H, $R^d$ is methyl and the chirality at phosphorous is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^4$ is unsubstituted phenyl. In another aspect of this embodiment, $R^8$ is halogen, $NR^{11}R^{12}$, $OR^{11}$, or $SR^{11}$. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH.

In one embodiment of Formula IV, $R^6$ is 2-propyl. In another aspect of this embodiment, $R^3$ is $(C_1-C_8)$alkyl. In another aspect of this embodiment, $R^3$ is 2-propyl. In another aspect of this embodiment, $R^c$ is methyl and $R^d$ is H. In another aspect of this embodiment, $R^c$ is methyl, $R^d$ is H and the chirality at phosphorous is S. In another aspect of this embodiment, $R^c$ is methyl, $R^d$ is H and the chirality at phosphorous is R. In another aspect of this embodiment, $R^c$ is H and $R^d$ is methyl. In another aspect of this embodiment, $R^c$ is H, $R^d$ is methyl and the chirality at phosphorous is S. In another aspect of this embodiment, $R^c$ is H, $R^d$ is methyl and the chirality at phosphorous is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^4$ is unsubstituted phenyl. In another aspect of this embodiment, $R^8$ is halogen, $NR^{11}R^{12}$, $OR^{11}$, or $SR^{11}$. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH.

In another embodiment of Formula IV, $R^8$ is $NH_2$ and $R^9$ is H. In another aspect of this embodiment, $R^3$ is $(C_1-C_8)$alkyl. In another aspect of this embodiment, $R^6$ is secondary alkyl. In another aspect of this embodiment, $R^3$ and $R^6$ are 2-propyl. In another aspect of this embodiment, $R^c$ is methyl and $R^d$ is H. In another aspect of this embodiment, the chirality at phosphorus is S. In another aspect of this embodiment, the chirality at phosphorus is R. In another aspect of this embodiment, $R^c$ is methyl, $R^d$ is H and the chirality at phosphorous is S. In another aspect of this embodiment, $R^c$ is methyl, $R^d$ is H and the chirality at phosphorous is R. In another aspect of this embodiment, $R^c$ is H and $R^d$ is methyl. In another aspect of this embodiment, $R^c$ is H, $R^d$ is methyl and the chirality at phosphorous is S. In another aspect of this embodiment, $R^c$ is H, $R^d$ is methyl and the chirality at phosphorous is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^4$ is unsubstituted phenyl. In another aspect of this embodiment, $R^4$ is unsubstituted phenyl and the chirality at phosphorous is S. In another aspect of this embodiment, $R^4$ is unsubstituted phenyl and the chirality at phosphorous is R. In another aspect of this embodiment, $R^3$ and $R^6$ are 2-propyl, $R^4$ is unsubstituted phenyl and the chirality at phosphorus is S. In another aspect of this embodiment, $R^3$ and $R^6$ are 2-propyl, $R^4$ is unsubstituted phenyl and the chirality at phosphorous is R. In another aspect of this embodiment, $R^3$ and $R^6$ are 2-propyl, $R^c$ is methyl and $R^d$ is H. In another aspect of this embodiment, $R^3$ and $R^6$ are 2-propyl, $R^c$ is methyl, $R^d$ is H and the chirality at phosphorous is S. In another aspect of this embodiment, $R^3$ and $R^6$ are 2-propyl, $R^c$ is methyl, $R^d$ is H and the chirality at phosphorous is R.

In another embodiment of Formula IV, $R^8$ is $NH_2$ and $R^9$ is $NH_2$. In another aspect of this embodiment, $R^3$ is $(C_1-C_8)$alkyl. In another aspect of this embodiment, $R^6$ is secondary alkyl. In another aspect of this embodiment, $R^3$ and $R^6$ are 2-propyl. In another aspect of this embodiment, $R^c$ is methyl and $R^d$ is H. In another aspect of this embodiment, the chirality at phosphorus is S. In another aspect of this embodiment, the chirality at phosphorus is R. In another aspect of this embodiment, $R^c$ is methyl, $R^d$ is H and the chirality at phosphorous is S. In another aspect of this embodiment, $R^c$ is methyl, $R^d$ is H and the chirality at phosphorous is R. In another aspect of this embodiment, $R^c$ is H and $R^d$ is methyl. In another aspect of this embodiment, $R^c$ is H, $R^d$ is methyl and the chirality at phosphorous is S. In another aspect of this embodiment, $R^c$ is H, $R^d$ is methyl and the chirality at phosphorous is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^4$ is unsubstituted phenyl. In another aspect of this embodiment, $R^4$ is unsubstituted phenyl and the chirality at phosphorous is S. In another aspect of this embodiment, $R^4$ is unsubstituted phenyl and the chirality at phosphorous is R. In another aspect of this embodiment, $R^3$ and $R^6$ are 2-propyl, $R^4$ is unsubstituted phenyl and the chirality at phosphorous is S. In another aspect of this embodiment, $R^3$ and $R^6$ are 2-propyl, $R^4$ is unsubstituted phenyl and the chirality at phosphorous is R. In another aspect of this embodiment, $R^3$ and $R^6$ are 2-propyl, $R^c$ is methyl and $R^d$ is H. In another aspect of this embodiment, $R^3$ and $R^6$ are 2-propyl, $R^c$ is methyl, $R^d$ is H and the chirality at phosphorous is S. In another aspect of this embodiment, $R^3$ and $R^6$ are 2-propyl, $R^c$ is methyl, $R^d$ is H and the chirality at phosphorous is R.

In another embodiment of Formula IV, $R^8$ is OH and $R^9$ is $NH_2$. In another aspect of this embodiment, $R^3$ is $(C_1-C_8)$ alkyl. In another aspect of this embodiment, $R^6$ is secondary alkyl. In another aspect of this embodiment, $R^3$ and $R^6$ are 2-propyl. In another aspect of this embodiment, $R^c$ is methyl and $R^d$ is H. In another aspect of this embodiment, the chirality at phosphorus is S. In another aspect of this embodiment, the chirality at phosphorus is R. In another aspect of this embodiment, $R^c$ is methyl, $R^d$ is H and the chirality at phosphorous is S. In another aspect of this embodiment, $R^c$ is methyl, $R^d$ is H and the chirality at phosphorous is R. In another aspect of this embodiment, $R^c$ is H and $R^d$ is methyl. In another aspect of this embodiment, $R^c$ is H, $R^d$ is methyl and the chirality at phosphorous is S. In another aspect of this embodiment, $R^c$ is H, $R^d$ is methyl and the chirality at phosphorous is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^4$ is unsubstituted phenyl. In another aspect of this embodiment, $R^4$ is unsubstituted phenyl and the chirality at phosphorous is S. In another aspect of this embodiment, $R^4$ is unsubstituted phenyl and the chirality at phosphorous is R. In another aspect of this embodiment, $R^3$ and $R^6$ are 2-propyl, $R^4$ is unsubstituted phenyl and the chirality at phosphorous is S. In another aspect of this embodiment, $R^3$ and $R^6$ are 2-propyl, $R^4$ is unsubstituted phenyl and the chirality at phosphorous is R. In another aspect of this embodiment, $R^3$ and $R^6$ are 2-propyl, $R^c$ is methyl and $R^d$ is H. In another aspect of this embodiment, $R^3$ and $R^6$ are 2-propyl, $R^c$ is methyl, $R^d$ is H and the chirality at phosphorous is S. In another aspect of this embodiment, $R^3$ and $R^6$ are 2-propyl, $R^c$ is methyl, $R^d$ is H and the chirality at phosphorous is R.

In another embodiment of Formula IV, $R^8$ is OH and $R^9$ is OH.

In one embodiment of Formulas I-IV, $R^{11}$ or $R^{12}$ is independently H, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —C(=O)($C_1-C_8$)alkyl, —S(O)$_n$ ($C_1-C_8$)alkyl or aryl($C_1-C_8$)alkyl. In another embodiment, $R^{11}$ and $R^{12}$ taken together with a nitrogen to which they are both attached, form a 3 to 7 membered heterocyclic ring wherein any one carbon atom of said heterocyclic ring can optionally be replaced with —O—, —S— or —NR$^a$—. Therefore, by way of example and not limitation, the moiety —NR$^{11}$R$^{12}$ can be represented by the heterocycles:

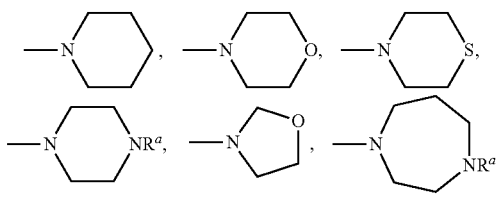

and the like.

In another embodiment, Formula I-IV is a compound selected from the group consisting of

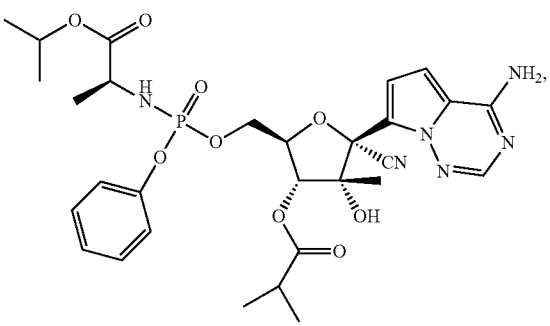

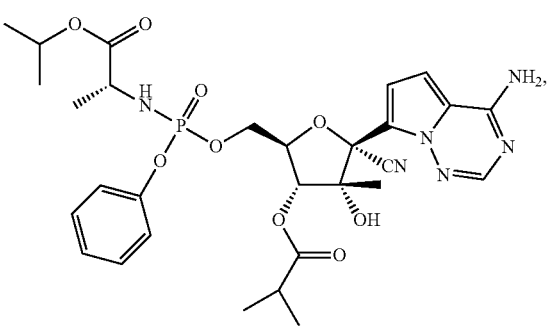

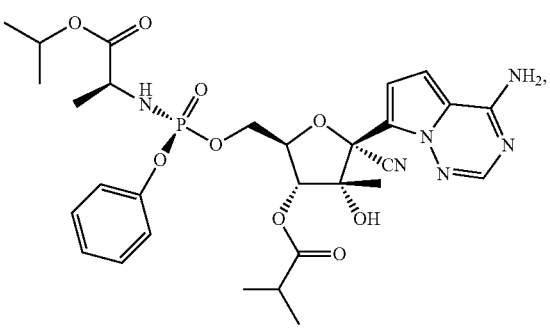

31
-continued
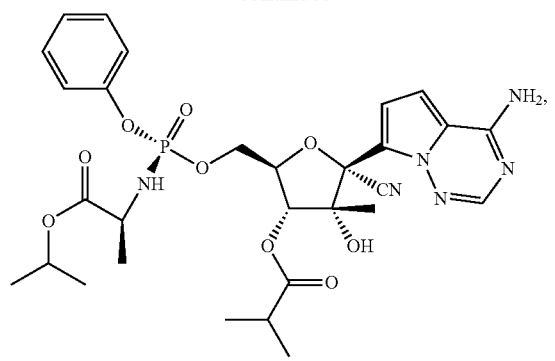
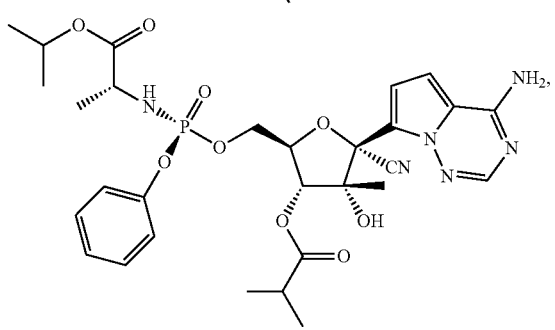
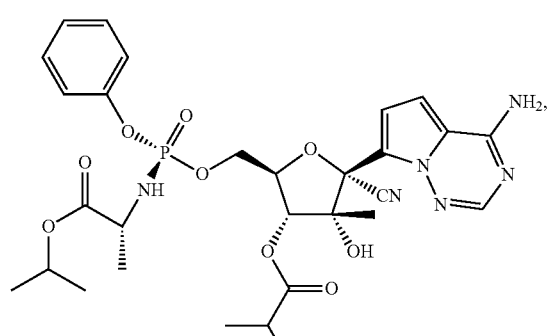
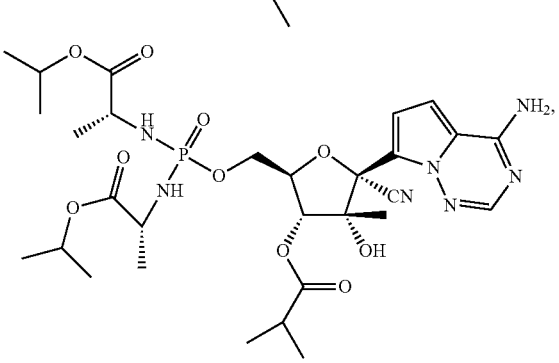
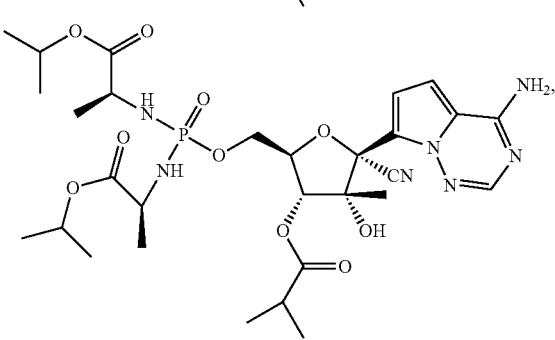
32
-continued
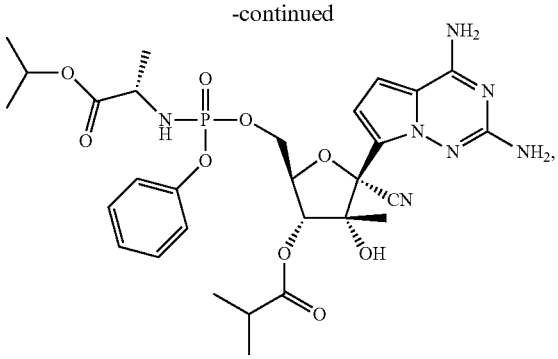
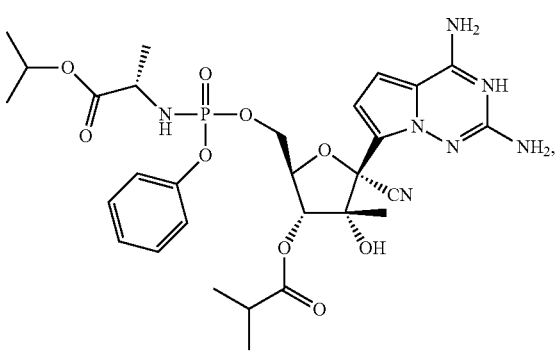
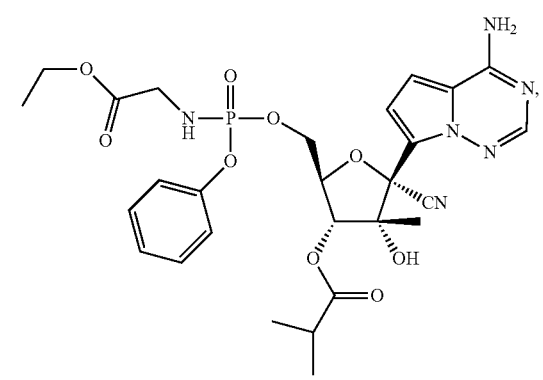
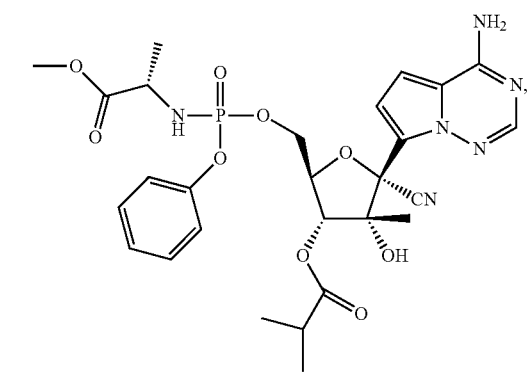

33
-continued
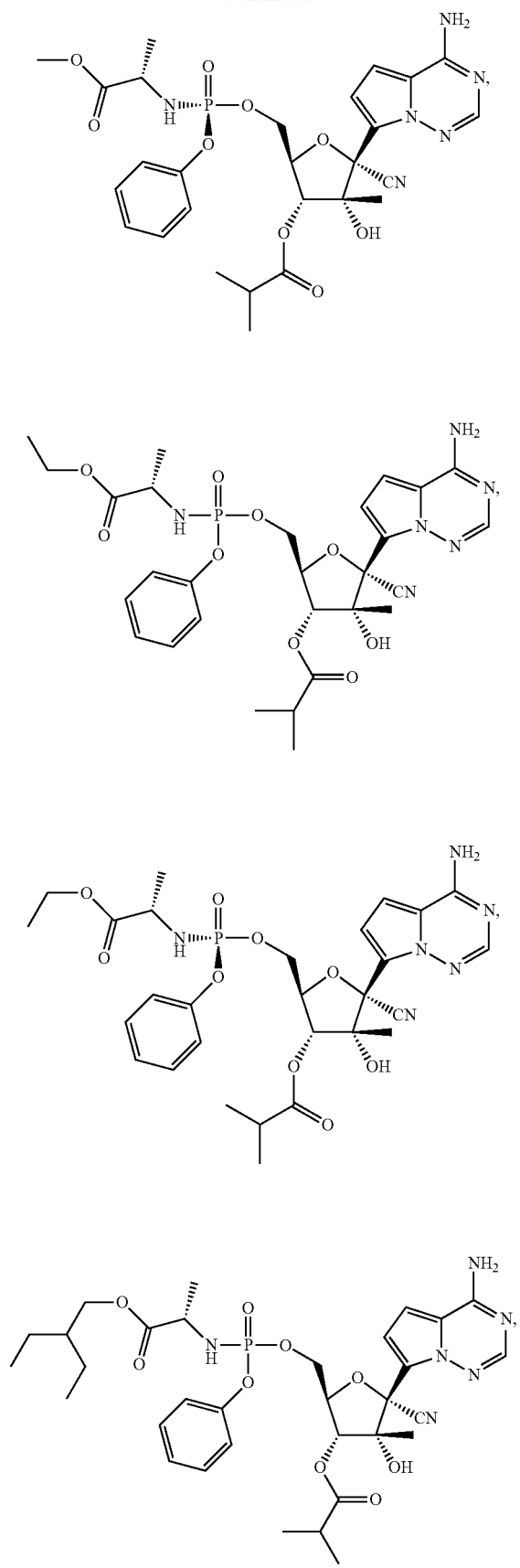
34
-continued
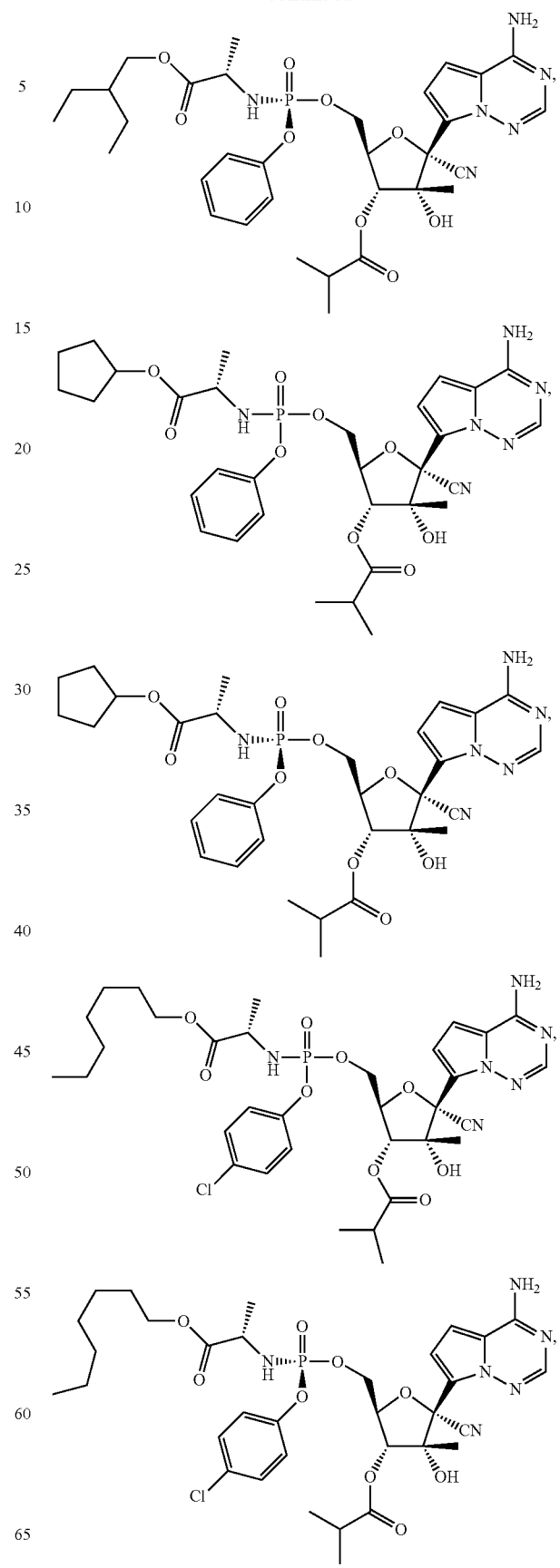

35
-continued
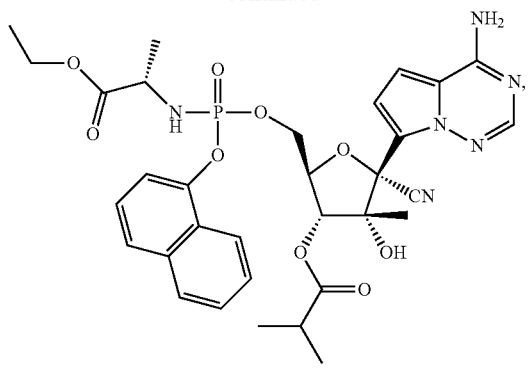
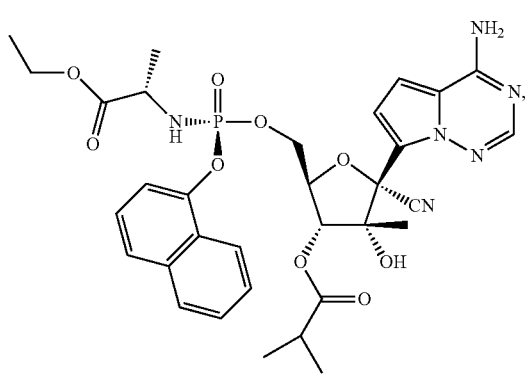
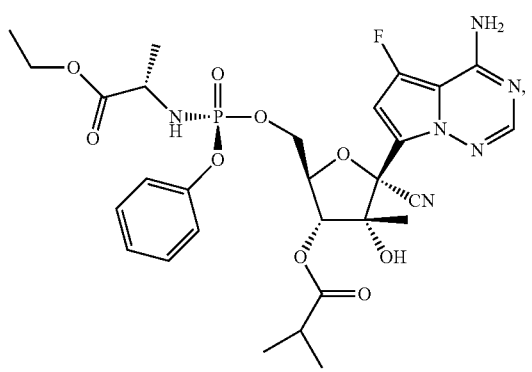
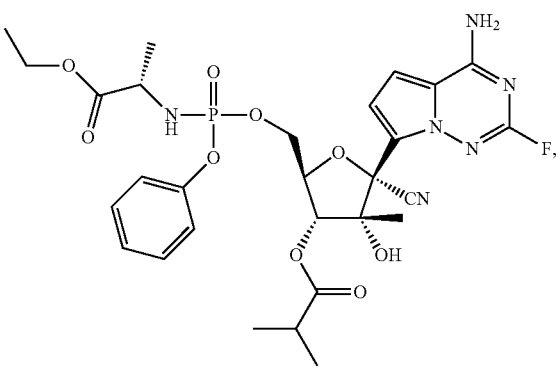
36
-continued
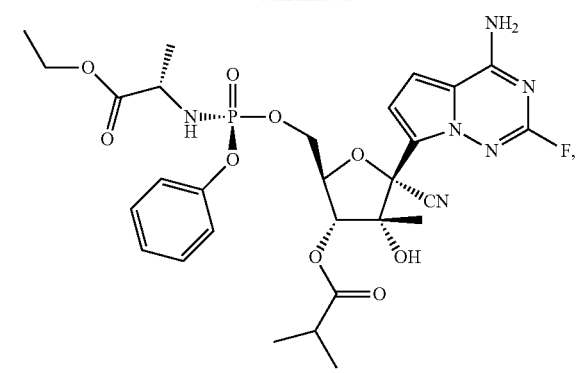
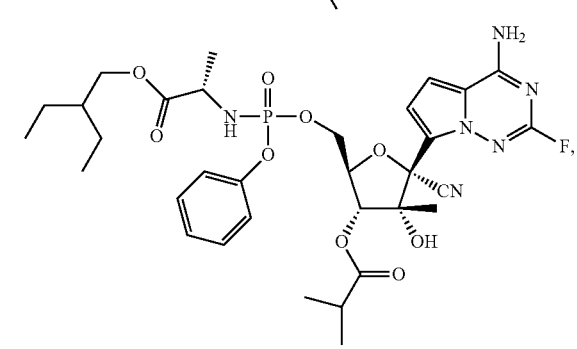
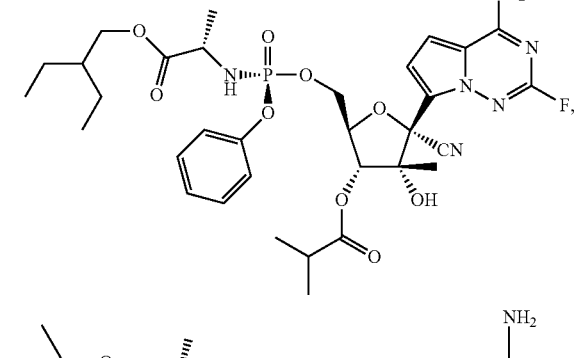
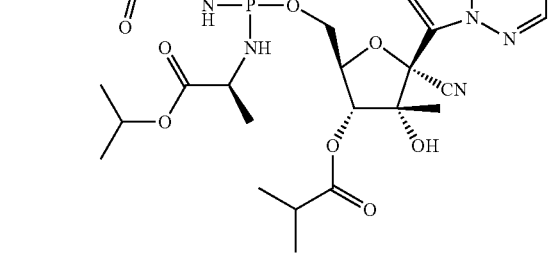
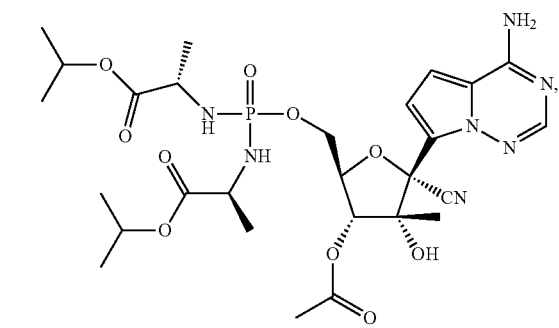

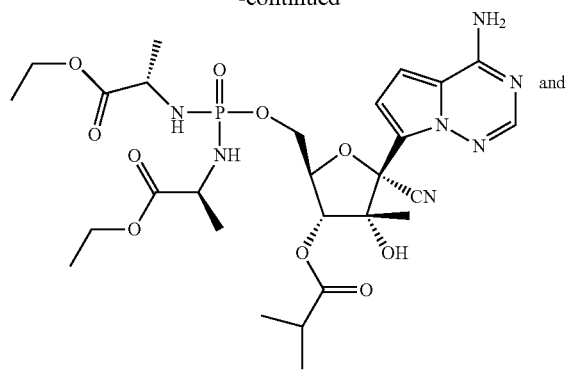
and
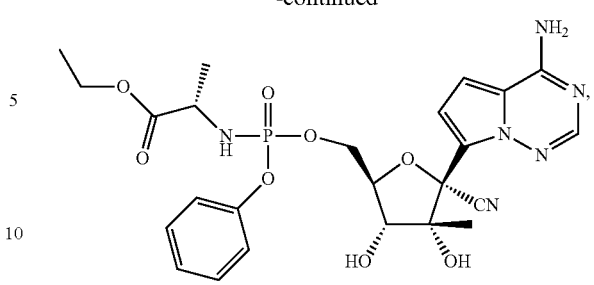
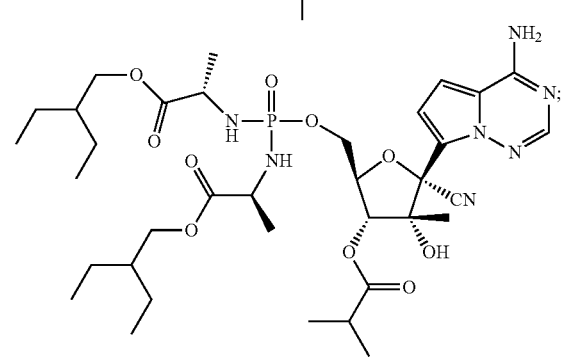
or a pharmaceutically acceptable salt or ester thereof.
In another embodiment, provided are compounds useful for synthesizing the compounds of Formula I selected form the group consisting of
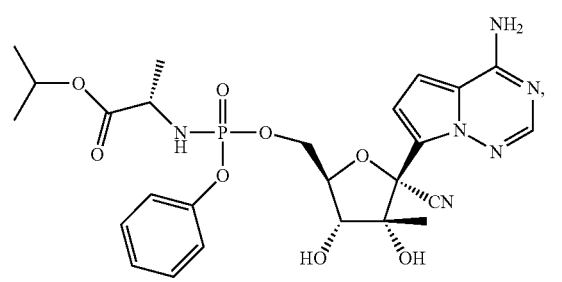
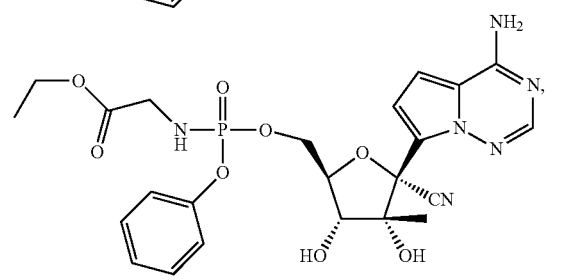
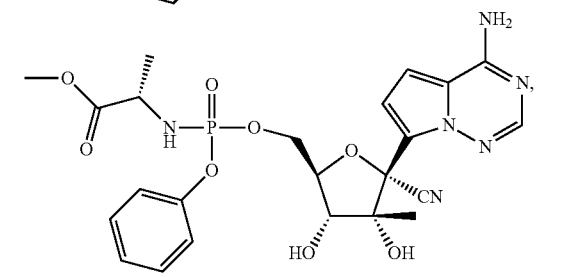
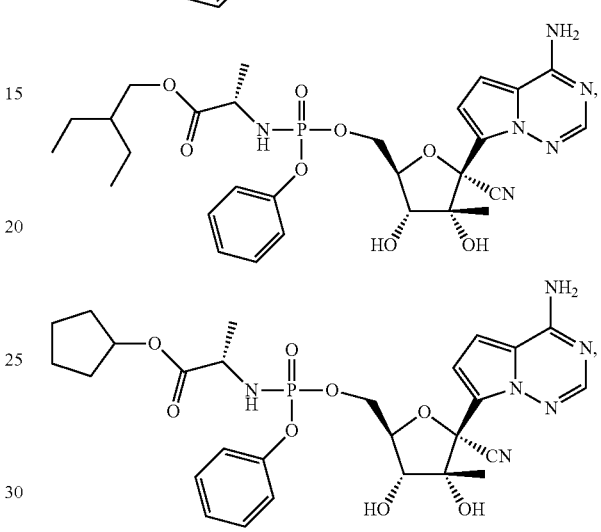
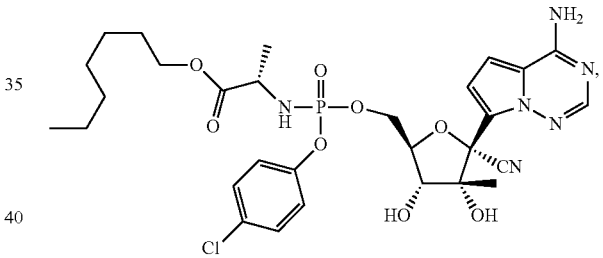
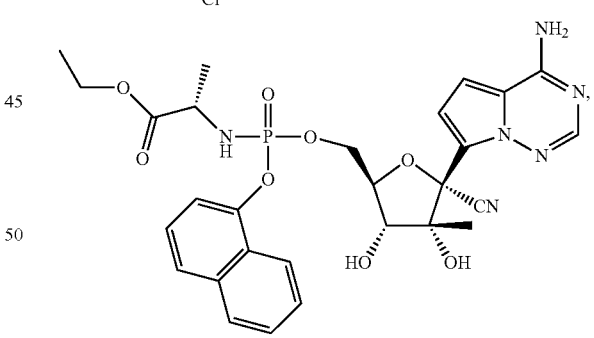
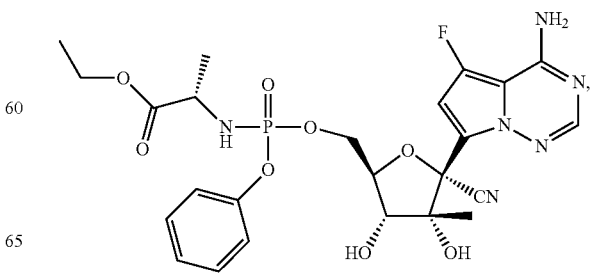

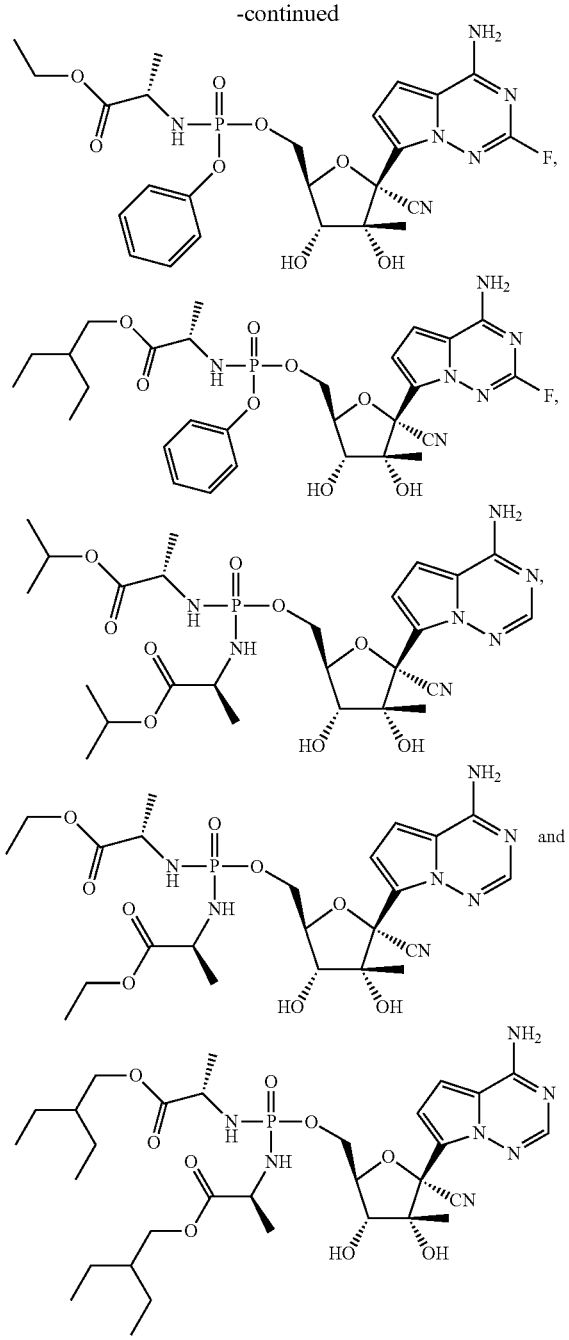

salt or esters thereof.

DEFINITIONS

Unless stated otherwise, the following terms and phrases as used herein are intended to have the following meanings:

When trade names are used herein, applicants intend to independently include the tradename product and the active pharmaceutical ingredient(s) of the tradename product.

As used herein, "a compound of the invention" or "a compound of Formula I" means a compound of Formula I or a pharmaceutically acceptable salt, thereof. Similarly, with respect to isolatable intermediates, the phrase "a compound of Formula (number)" means a compound of that formula and pharmaceutically acceptable salts, thereof.

The term "treating" and grammatical equivalents thereof, when used in the context of treating a disease, means slowing or stopping the progression of a disease, or ameliorating at least one symptom of a disease, more preferably ameliorating more than one symptom of a disease. For example, treatment of a hepatitis C virus infection can include reducing the HCV viral load in an HCV infected human being, and/or reducing the severity of jaundice present in an HCV infected human being.

"Alkyl" is hydrocarbon containing normal, secondary, tertiary or cyclic carbon atoms. For example, an alkyl group can have 1 to 20 carbon atoms (i.e., $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_7CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH═$CH_2$), allyl (—$CH_2$CH═$CH_2$), cyclopentenyl (—$C_5H_7$), and 5-hexenyl (—$CH_2CH_2CH_2CH_2$CH═$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—CH$_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—CH$_2$—), 1,1-ethyl (—CH(CH$_3$)—), 1,2-ethyl (—CH$_2$CH$_2$—), 1,1-propyl (—CH(CH$_2$CH$_3$)—), 1,2-propyl (—CH$_2$CH (CH$_3$)—), 1,3-propyl (—CH$_2$CH$_2$CH$_2$—), 1,4-butyl (—CH$_2$CH$_2$CH$_2$CH$_2$—), and the like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH═CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene (—C≡C—), propargyl (—CH$_2$C≡C—), and 4-pentynyl (—CH$_2$CH$_2$CH$_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately sp$^3$. Nonlimiting types of amino include —NH$_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl) (aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH (CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C (O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl" means, unless otherwise stated, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, ═O, —OR$^b$, —SR$^b$, —S$^-$, —NR$^b_2$, —N$^+$R$^b_3$, ═NR$^b$, —CX$_3$, —CN, —OCN, —SCN, —N═C═O, —NCS, —NO, —NO$_2$, ═N$_2$, —N$_3$, —NHC (═O)R$^b$, —OC(═O)R$^b$, —NHC(═O)NR$^b_2$, —S(═O)$_2$—, —S(═O)$_2$OH, —S(═O)$_2$R$^b$, —OS(═O)$_2$OR$^b$, —S(═O)$_2$NR$^b_2$, —S(═O)R$^b$, —OP(═O)(OR$^b$)$_2$, —P(═O)(OR$^b$)$_2$, —P(═O)(O$^-$)$_2$, —P(═O)(OH)$_2$, —P(O)(OR$^b$)(O$^-$), —C(═O)R$^b$, —C(═O)X, —C(S)R$^b$, —C(O)OR$^b$, —C(O) O$^-$, —C(S)OR$^b$, —C(O)SR$^b$, —C(S)SR$^b$, —C(O)NR$^b_2$, —C(S)NR$^b_2$, —C(═NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of Formula I-IV should be selected in order to provide a compound which is sufficiently stable to provide a pharmaceutically useful compound which can be formulated into an acceptably stable pharmaceutical composition. Compounds of Formula I-IV which have such stability are contemplated as falling within the scope of the present invention.

The compounds of Formula I-IV also include molecules that incorporate isotopes of the atoms specified in the particular molecules. Non-limiting examples of these isotopes include D, T, $^{14}$C, $^{13}$C and $^{15}$N. All such isotopic variations of these molecules are comprised within the instant invention.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., —OCH$_3$, etc.), an amine (e.g., —NHCH$_3$, —N(CH$_3$)$_2$, etc.), or a thioalkyl group (e.g., —SCH$_3$). If a non-terminal carbon atom of the alkyl group which is not attached to the parent molecule is replaced with a heteroatom (e.g., O, N, or S) the resulting heteroalkyl groups are, respectively, an alkyl ether (e.g., —CH$_2$CH$_2$—O—CH$_3$, etc.), an alkyl amine (e.g., —CH$_2$NHCH$_3$, —CH$_2$N(CH$_3$)$_2$, etc.), or a thioalkyl ether (e.g., —CH$_2$—S—CH$_3$). If a terminal carbon atom of the alkyl group is replaced with a heteroatom (e.g., O, N, or S), the resulting heteroalkyl groups are, respectively, a hydroxyalkyl group (e.g., —CH$_2$CH$_2$—OH), an aminoalkyl group (e.g., —CH$_2$NH$_2$), or an alkyl thiol group (e.g., —CH$_2$CH$_2$—SH). A heteroalkyl group can have, for example, 1 to 20 carbon atoms, 1 to 10 carbon atoms, or 1 to 6 carbon atoms. A C$_1$-C$_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W.A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocyclyls include, for example, heterocyclic rings substituted with any of the substituents disclosed herein including carbonyl groups. A non-limiting example of a carbonyl substituted heterocyclyl is:

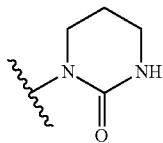 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

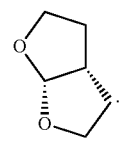

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylalkyl" refers to an acyclic alkyl radical in which one of the hydrogen atoms bonded to a carbon atom, typically a terminal or sp$^3$ carbon atom, is replaced with a heterocyclyl radical (i.e., a heterocyclyl-alkylene-moiety). Typical heterocyclyl alkyl groups include, but are not limited to heterocyclyl-CH$_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 3 to 20 carbon atoms, e.g., the alkyl portion of the arylalkyl group is 1 to 6 carbon atoms and the heterocyclyl moiety is 2 to 14 carbon atoms. Examples of heterocyclylalkyls include by way, of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, etc., 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, etc.

"Heterocyclylalkenyl" refers to an acyclic alkenyl radical in which one of the hydrogen atoms bonded to a carbon atom, typically a terminal or $sp^3$ carbon atom, but also a $sp^2$ carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 4 to 20 carbon atoms, e.g., the alkenyl portion of the heterocyclyl alkenyl group is 2 to 6 carbon atoms and the heterocyclyl moiety is 2 to 14 carbon atoms.

"Heterocyclylalkynyl" refers to an acyclic alkynyl radical in which one of the hydrogen atoms bonded to a carbon atom, typically a terminal or $sp^3$ carbon atom, but also an sp carbon atom, is replaced with a heterocyclyl radical (i.e., a heterocyclyl-alkynylene-moiety). The heterocyclyl portion of the heterocyclyl alkynyl group includes any of the heterocyclyl groups described herein, including those described in *Principles of Modern Heterocyclic Chemistry*, and the alkynyl portion of the heterocyclyl alkynyl group includes any of the alkynyl groups disclosed herein. One skilled in the art will also understand that the heterocyclyl group can be attached to the alkynyl portion of the heterocyclyl alkynyl by means of a carbon-carbon bond or a carbon-heteroatom bond, with the proviso that the resulting group is chemically stable. The heterocyclyl alkynyl group comprises 4 to 20 carbon atoms, e.g., the alkynyl portion of the heterocyclyl alkynyl group is 2 to 6 carbon atoms and the heterocyclyl moiety is 2 to 14 carbon atoms.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo[4,5], [5,5], [5,6] or [6,6] system, or 9 or 10 ring atoms arranged as a bicyclo[5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to an acyclic alkyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Arylheteroalkyl" refers to a heteroalkyl as defined herein, in which a hydrogen atom (which may be attached either to a carbon atom or a heteroatom) has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, etc. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include —$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, etc.

The term "optionally substituted" in reference to a particular moiety of the compound of Formula I-IV (e.g., an optionally substituted aryl group) refers to a moiety wherein all substituents are hydrogen or wherein one or more of the hydrogens of the moiety may be replaced by substituents such as those listed under the definition of "substituted".

The term "optionally replaced" in reference to a particular moiety of the compound of Formula I-IV (e.g., the carbon atoms of said ($C_1$-$C_8$)alkyl may be optionally replaced by —O—, —S—, or —$NR^a$—) means that one or more of the methylene groups of the ($C_1$-$C_8$)alkyl may be replaced by 0, 1, 2, or more of the groups specified (e.g., —O—, —S—, or —$NR^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —$CH_2(C^*)H_2(C^*)H_2CH_3$ or alkylene moiety —$CH_2(C^*)H_2(C^*)H_2CH_2$— the $C^*$ atoms would be considered to be the non-terminal carbon atoms.

"Linker" or "link" means a chemical moiety comprising a covalent bond or a chain of atoms. Linkers include repeating units of alkyloxy (e.g. polyethyleneoxy, PEG, polymethyleneoxy) and alkylamino (e.g. polyethyleneamino, Jeffamine™); and diacid ester and amides including succinate, succinamide, diglycolate, malonate, and caproamide.

The terms such as "oxygen-linked", "nitrogen-linked", "carbon-linked", "sulfur-linked", or "phosphorous-linked"

mean that if a bond between two moieties can be formed by using more than one type of atom in a moiety, then the bond formed between the moieties is through the atom specified. For example, a nitrogen-linked amino acid would be bonded through a nitrogen atom of the amino acid rather than through an oxygen or carbon atom of the amino acid.

Some embodiments of the compounds of Formula I-IV comprise the moiety

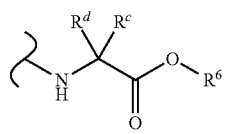

which may comprise a radical of a nitrogen-linked naturally occurring α-amino acid ester. Examples of naturally occurring amino acids include isoleucine, leucine, lysine, methionine, phenylalanine, threonine, tryptophan, valine, alanine, asparagine, aspartic acid, cysteine, glutamic acid, glutamine, glycine, proline, selenocysteine, serine, tyrosine, arginine, histidine, ornithine and taurine. The esters of these amino acids comprise any of those described for the substituent $R^6$, particularly those in which $R^6$ is optionally substituted ($C_1$-$C_8$)alkyl.

Unless otherwise specified, the carbon atoms of the compounds of Formula I-IV are intended to have a valence of four. In some chemical structure representations where carbon atoms do not have a sufficient number of variables attached to produce a valence of four, the remaining carbon substituents needed to provide a valence of four should be assumed to be hydrogen. For example,

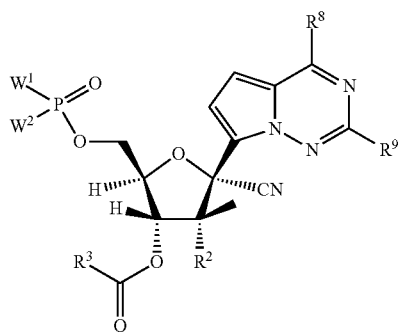

has the same meaning as

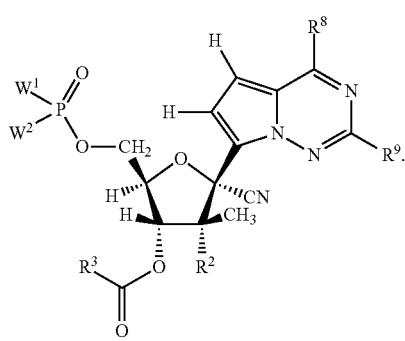

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

Protected compounds may also exhibit altered, and in some cases, optimized properties in vitro and in vivo, such as passage through cellular membranes and resistance to enzymatic degradation or sequestration. In this role, protected compounds with intended therapeutic effects may be referred to as prodrugs. Another function of a protecting group is to convert the parental drug into a prodrug, whereby the parental drug is released upon conversion of the prodrug in vivo. Because active prodrugs may be absorbed more effectively than the parental drug, prodrugs may possess greater potency in vivo than the parental drug. Protecting groups are removed either in vitro, in the instance of chemical intermediates, or in vivo, in the case of prodrugs. With chemical intermediates, it is not particularly important that the resulting products after deprotection, e.g. alcohols, be physiologically acceptable, although in general it is more desirable if the products are pharmacologically innocuous.

"Prodrug moiety" means a labile functional group which separates from the active inhibitory compound during metabolism, systemically, inside a cell, by hydrolysis, enzymatic cleavage, or by some other process (Bundgaard, Hans, "Design and Application of Prodrugs" in Textbook of Drug Design and Development (1991), P. Krogsgaard-Larsen and H. Bundgaard, Eds. Harwood Academic Publishers, pp. 113-191). Enzymes which are capable of an enzymatic activation mechanism with the phosphonate prodrug compounds of the invention include, but are not limited to, amidases, esterases, microbial enzymes, phospholipases, cholinesterases, and phosphases. Prodrug moieties can serve to enhance solubility, absorption and lipophilicity to optimize drug delivery, bioavailability and efficacy. A prodrug moiety may include an active metabolite or drug itself.

The phosphate group may be a phosphate prodrug moiety. The prodrug moiety may be sensitive to hydrolysis. Alternatively, the prodrug moiety may be sensitive to enzymatic potentiated cleavage, such as a lactate ester or a phosphonamidate-ester group.

It is to be noted that all enantiomers, diastereomers, and racemic mixtures, tautomers, polymorphs, pseudopolymorphs of compounds within the scope of Formula I-IV and pharmaceutically acceptable salts thereof are embraced by the present invention. All mixtures of such enantiomers and diastereomers are within the scope of the present invention.

A compound of Formula I-IV and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I-IV and their pharmaceutically acceptable salts.

A compound of Formula I-IV and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I-IV and their pharmaceutically acceptable salts.

Selected substituents comprising the compounds of Formula I-IV are present to a recursive degree. In this context, "recursive substituent" means that a substituent may recite another instance of itself. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents are an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

The modifier "about" used in connection with a quantity is inclusive of the stated value and has the meaning dictated by the context (e.g., includes the degree of error associated with measurement of the particular quantity).

Any reference to the compounds of the invention described herein also includes a reference to a physiologically acceptable salt thereof. Examples of physiologically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR^a_4{}^+$ (wherein $R^a$ is defined herein). Physiologically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Physiologically acceptable salts of a compound of a hydroxy group include the anion of said compound in combination with a suitable cation such as $Na^+$ and $NR^a_4{}^+$.

For therapeutic use, salts of active ingredients of the compounds of the invention will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

Finally, it is to be understood that the compositions herein comprise compounds of the invention in their un-ionized, as well as zwitterionic form, and combinations with stoichiometric amounts of water as in hydrates.

The compounds of the invention, exemplified by Formula I-IV have chiral centers, e.g. chiral carbon or phosphorus atoms. For example, the phosphorous atoms of Formula I-IV may be chiral because they have four different substituents. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, reactivities and biological properties. For example, the compounds of Formula I-IV may have a chiral phosphorus atom when phosphorus has four different substituents, e.g., Formula IV, where the chirality is R or S. When $R^c$ and $R^d$ of the amino acid of the phosphoramidate of Formula IV are different, there are two centers of chirality in the molecule leading to potential diastereomeric mixtures of compounds, e.g. R,S; S,R; S,S and R,R isomers. Mixtures of diastereomers may be separate under high resolution analytical procedures such as electrophoresis, crystallization and/or chromatography. Diastereomeres may have different physical attributes such as, but not limited to, solubility, chemical stabilities and crystallinity and may also have different biological properties such as, but not limited to, enzymatic stability, absorption and metabolic stability.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

Whenever a compound described herein is substituted with more than one of the same designated group, e.g., "$R^a$" or "$R^1$", then it will be understood that the groups may be the same or different, i.e., each group is independently selected. Wavy lines, $\sim\sim\sim$, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that the pyrrolo[1,2-f][1,2,4]triazine nucleosides can exist in tautomeric forms. For example, but not by way of limitation, structures (a) and (b) can have equivalent tautomeric forms as shown below:

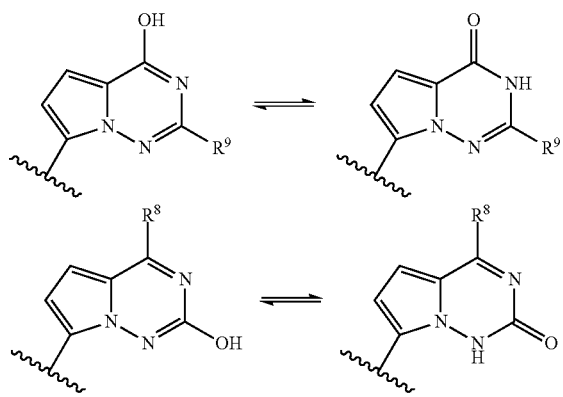

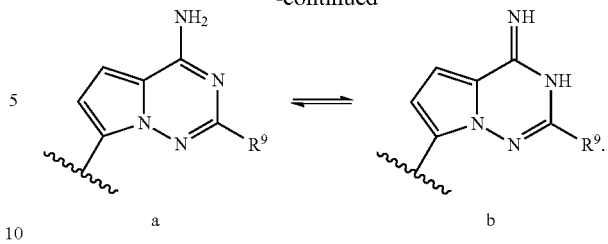

All possible tautomeric forms of the heterocycles in all of the embodiments disclosed herein are within the scope of the invention.

The compounds of Formula I-IV also include molecules that incorporate isotopes of the atoms specified in the particular molecules. Non-limiting examples of these isotopes include D, T, $^{14}C$, $^{13}C$ and $^{15}N$. All such isotopic variations of these molecules are provided by the instant invention.

Methods of Inhibition of HCV Polymerase

Another aspect of the invention relates to methods of inhibiting the activity of HCV polymerase comprising the step of treating a sample suspected of containing HCV with a composition of the invention.

Compositions of the invention may act as inhibitors of HCV polymerase, as intermediates for such inhibitors or have other utilities as described below. The inhibitors will bind to locations on the surface or in a cavity of HCV polymerase having a geometry unique to HCV polymerase. Compositions binding HCV polymerase may bind with varying degrees of reversibility. Those compounds binding substantially irreversibly are ideal candidates for use in this method of the invention. Once labeled, the substantially irreversibly binding compositions are useful as probes for the detection of HCV polymerase. Accordingly, the invention relates to methods of detecting HCV polymerase in a sample suspected of containing HCV polymerase comprising the steps of: treating a sample suspected of containing HCV polymerase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl, carboxyl, sulfhydryl or amino.

Within the context of the invention, samples suspected of containing HCV polymerase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces HCV polymerase, frequently a pathogenic organism such as HCV. Samples can be contained in any medium including water and organic solvent\water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of HCV polymerase after application of the composition can be observed by any method including direct and indirect methods of detecting HCV polymerase activity. Quantitative, qualitative, and semiquantitative methods of determining HCV polymerase activity are all contemplated. Typically one of the screening methods described above are applied, however, any other method such as observation of the physiological properties of a living organism are also applicable.

Organisms that contain HCV polymerase include the HCV virus. The compounds of this invention are useful in the treatment or prophylaxis of HCV infections in animals or in man.

However, in screening compounds capable of inhibiting human immunodeficiency viruses, it should be kept in mind that the results of enzyme assays may not correlate with cell culture assays. Thus, a cell based assay should be the primary screening tool.

Screens for HCV Polymerase Inhibitors

Compositions of the invention are screened for inhibitory activity against HCV polymerase by any of the conventional techniques for evaluating enzyme activity. Within the context of the invention, typically compositions are first screened for inhibition of HCV polymerase in vitro and compositions showing inhibitory activity are then screened for activity in vivo. Compositions having in vitro Ki (inhibitory constants) of less then about $5\times10^{-6}$ M, typically less than about $1\times10^{-7}$ M and preferably less than about $5\times10^{-8}$ M are preferred for in vivo use.

Useful in vitro screens have been described in detail and will not be elaborated here. However, the examples describe suitable in vitro assays.

Pharmaceutical Formulations

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcelluose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

Routes of Administration

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

Combination Therapy

Compositions of the invention are also used in combination with other active ingredients. Preferably, the other active therapeutic ingredients or agents are interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

Combinations of the compounds of Formula I-IV are typically selected based on the condition to be treated, cross-reactivities of ingredients and pharmaco-properties of the combination. For example, when treating an infection (e.g., HCV), the compositions of the invention are combined with one or more other active therapeutic agents (such as, but not limited to, those described herein).

Suitable active therapeutic agents or ingredients which can be combined with the compounds of Formula I-IV can include interferons, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon; ribavirin analogs, e.g., rebetol, copegus, VX-497, and viramidine (taribavirin); NS5a inhibitors, e.g., A-831, A-689 and BMS-790052; NS5b polymerase inhibitors, e.g., NM-283, valopicitabine, R1626, PSI-6130 (R1656), IDX184, PSI-7851, HCV-796, BILB 1941, MK-0608, NM-107, R7128, VCH-759, PF-868554, GSK625433, and XTL-2125; NS3 protease inhibitors, e.g., SCH-503034 (SCH-7), VX-950 (Telaprevir), ITMN-191, and BILN-2065; alpha-glucosidase 1 inhibitors, e.g., MX-3253 (celgosivir) and UT-231B; hepatoprotectants, e.g., IDN-6556, ME 3738, MitoQ, and LB-84451; pharmacokinetic enhancers, e.g., BAS-100, SPI-452, PF-4194477, TMC-41629, GS-9350, GS-9585, and roxythromycin; TLR-7 agonists, e.g., imiquimod, 852A, GS-9524, ANA-773, ANA-975, AZD-8848 (DSP-3025), PF-04878691, and SM-360320; mevalonate decarboxylase antagonists, e.g., statins, HMGCoA synthase inhibitors (e.g., hymeglusin), squalene synthesis inhibitors (e.g., zaragozic acid); angiotensin II receptor antagonists, e.g., losartan, irbesartan, olmesartan, candesartan, valsartan, telmisartan, eprosartan; angiotensin-converting enzyme inhibitors, e.g., captopril, zofenopril, enalapril, ramipril, quinapril, perindopril, lisinopril, benazepril, fosinopril; other anti-fibrotic agents, e.g., amiloride and endothelin antagonists, e.g. bosentan and ambrisentan; non-nucleoside inhibitors of HCV, e.g., benzimidazole derivatives, benzo-1,2,4-thiadiazine derivatives, and phenylalanine derivatives; and other drugs for treating HCV, e.g., zadaxin, nitazoxanide (alinea), BIVN-401 (virostat), DEBIO-025, VGX-410C, EMZ-702, ABT-450, AVI 4065, bavituximab, BMS650032, VX-813, GS-9256, ABT-072, BMS791325, MK-3281, VCH-222, AZD7295, SCY-635, BMS-824393, MK-1220, MK-5172, BI201335, MK-7009, SCH 900518, TMC435, ABT-333, ANA-598, BI207127, GS-9190, PF-00868554, BMS790052, oglufanide, PYN-17, KPE02003002, actilon (CPG-10101), KRN-7000, civacir, GI-5005, ANA-773, ANA-975, PF-04878691, XTL-6865, ANA 971, NOV-205, tarvacin, EHC-18, and NIM811. One preferred combination comprises a compound of Formula I-IV or pharmaceutically acceptable salt thereof and ribavirin. Another preferred combination comprises a compound of Formula I-IV or pharmaceutically acceptable salt thereof and telaprevir. Another preferred combination comprises a compound of Formula I-IV or pharmaceutically acceptable salt thereof and boceprevir. Another preferred combination comprises a compound of Formula I-IV or pharmaceutically acceptable salt thereof and INX-08189. Another preferred combination comprises a compound of Formula I-IV or pharmaceutically acceptable salt thereof and PSI-7851 or PSI-7977. Another preferred combination comprises a compound of Formula I-IV or pharmaceutically acceptable salt thereof and RG7128. Another preferred combination comprises a compound of Formula I-IV or pharmaceutically acceptable salt thereof and R7227. Another preferred combination comprises a compound of Formula I-IV or pharmaceutically acceptable salt thereof and locteron, albuferon, Peg-Intron, Pegasys or Copegus. Another preferred combination comprises a compound of Formula I-IV or pharmaceutically acceptable salt thereof and DEBIO-025. Another preferred combination comprises a compound of Formula I-IV or pharmaceutically acceptable salt thereof and GS-9190. Another preferred combination comprises a compound of Formula I-IV or pharmaceutically acceptable salt thereof and RG7348.

In yet another embodiment, the present application discloses pharmaceutical compositions comprising a compound of the present invention, or a pharmaceutically acceptable salt, solvate, and/or ester thereof, in combination with at least one additional therapeutic agent, and a pharmaceutically acceptable carrier or exipient.

According to the present invention, the therapeutic agent used in combination with the pharmaceutical compositions comprising a compound of the present invention can be any agent having a therapeutic effect when used in combination with the compound of the present invention. For example, the therapeutic agent used in combination with the compound of the present invention can be interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

In another embodiment, the present application provides pharmaceutical compositions comprising a compound of the present invention, or a pharmaceutically acceptable salt, solvate, and/or ester thereof, in combination with at least one additional therapeutic agent selected from the group consisting of pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, albuferon, rebetol, copegus, VX-497, viramidine (taribavirin), A-831, A-689, NM-283, valopicitabine, R1626, PSI-6130 (R1656), HCV-796, BILB 1941, MK-0608, NM-107, R7128, VCH-759, PF-868554, GSK625433, XTL-2125, SCH-503034 (SCH-7), VX-950 (Telaprevir), ITMN-191, and BILN-2065, MX-3253 (celgosivir), UT-231B, IDN-6556, ME 3738, MitoQ, and LB-84451, BAS-100, SPI-452, PF-4194477, TMC-41629, GS-9350, GS-9585, and roxythromycin, imiquimod, 852A, GS-9524, ANA-773, ANA-975, AZD-8848 (DSP-3025), PF-04878691 and SM-360320 benzimidazole derivatives, benzo-1,2,4-thiadiazine derivatives, and phenylalanine derivatives, zadaxin, nitazoxanide (alinea), BIVN-401 (virostat), DEBIO-025, VGX-410C, EMZ-702, ABT-450, AVI 4065, bavituximab, BMS650032, VX-813, GS-9256, ABT-072, BMS791325, MK-3281, VCH-222, AZD7295, SCY-635, BMS-824393, MK-1220, MK-5172, BI201335, MK-7009, SCH 900518, TMC435, ABT-333, ANA-598, BI207127, GS-9190, PF-00868554, BMS790052, oglufanide, PYN-17, KPE02003002, actilon (CPG-10101), KRN-7000, civacir, GI-5005, ANA-773, ANA-975, PF-04878691, XTL-6865, ANA 971, NOV-205, tarvacin, EHC-18, statins, hymeglusin, zaragozic acid, angiotensin II receptor antagonists, angiotensin-converting enzyme inhibitors, amiloride, endothelin antagonists and NIM811 and a pharmaceutically acceptable carrier or exipient. One preferred pharmaceutical composition comprises a compound of Formula I-IV or pharmaceutically acceptable salt thereof and ribavirin. Another preferred pharmaceutical composition comprises a compound of Formula I-IV or pharmaceutically acceptable salt thereof and telaprevir. Another preferred pharmaceutical composition comprises a compound of Formula I-IV or pharmaceutically acceptable salt thereof and boceprevir. Another preferred pharmaceutical composition comprises a compound of Formula I-IV or pharmaceutically acceptable salt thereof and INX-08189. Another preferred pharmaceutical composition comprises a compound of Formula I-IV or pharmaceutically acceptable salt thereof and PSI-7851 or PSI-7977. Another preferred pharmaceutical composition comprises a compound of Formula I-IV or pharmaceutically acceptable salt thereof and RG7128. Another preferred pharmaceutical composition comprises a compound of Formula I-IV or pharmaceutically acceptable salt thereof and R7227. Another preferred pharmaceutical composition comprises a compound of Formula I-IV or pharmaceutically acceptable salt thereof and locteron, albuferon, Peg-Intron, Pegasys or Copegus. Another preferred pharmaceutical composition comprises a compound of Formula I-IV or pharmaceutically acceptable salt thereof and DEBIO-025. Another preferred pharmaceutical composition comprises a compound of Formula I-IV or pharmaceutically acceptable salt thereof and GS-9190. Another preferred pharmaceutical composition comprises a compound of Formula I-IV or pharmaceutically acceptable salt thereof and RG7348.

In yet another embodiment, the present application provides a combination pharmaceutical agent comprising:

a) a first pharmaceutical composition comprising a compound of the present invention, or a pharmaceutically acceptable salt, solvate, or ester thereof; and b) a second pharmaceutical composition comprising at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV, and combinations thereof.

Combinations of the compounds of Formula I-IV and additional active therapeutic agents may be selected to treat patients infected with HCV and other conditions such as HIV infections. Accordingly, the compounds of Formula I-IV may be combined with one or more compounds useful in treating HIV, for example HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

More specifically, one or more compounds of the present invention may be combined with one or more compounds selected from the group consisting of 1) HIV protease inhibitors, e.g., amprenavir, atazanavir, fosamprenavir, indinavir, lopinavir, ritonavir, lopinavir+ritonavir, nelfinavir, saquinavir, tipranavir, brecanavir, darunavir, TMC-126, TMC-114, mozenavir (DMP-450), JE-2147 (AG1776), AG1859, DG35, L-756423, RO0334649, KNI-272, DPC-681, DPC-684, and GW640385X, DG17, PPL-100, 2) a HIV non-nucleoside inhibitor of reverse transcriptase, e.g., capravirine, emivirine, delaviridine, efavirenz, nevirapine, (+) calanolide A, etravirine, GW5634, DPC-083, DPC-961, DPC-963, MIV-150, and TMC-120, TMC-278 (rilpivirine), efavirenz, BILR 355 BS, VRX 840773, UK-453,061, RDEA806, 3) a HIV nucleoside inhibitor of reverse transcriptase, e.g., zidovudine, emtricitabine, didanosine, stavudine, zalcitabine, lamivudine, abacavir, amdoxovir, elvucitabine, alovudine, MIV-210, racivir (±-FTC), D-d4FC, emtricitabine, phosphazide, fozivudine tidoxil, fosalvudine tidoxil, apricitibine (AVX754), amdoxovir, KP-1461, abacavir+lamivudine, abacavir+lamivudine+zidovudine, zidovudine+lamivudine, 4) a HIV nucleotide inhibitor of reverse transcriptase, e.g., tenofovir, tenofovir disoproxil fumarate+emtricitabine, tenofovir disoproxil fumarate+emtricitabine+efavirenz, and adefovir, 5) a HIV integrase inhibitor, e.g., curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, zintevir (AR-177), L-870812, and L-870810, MK-0518 (raltegravir), BMS-707035, MK-2048, BA-011, BMS-538158, GSK364735C, 6) a gp41 inhibitor, e.g., enfuvirtide, sifuvirtide, FB006M, TRI-1144, SPC3, DES6, Locus gp41, CovX, and REP 9, 7) a CXCR4 inhibitor, e.g., AMD-070, 8) an entry inhibitor, e.g., SP01A, TNX-355, 9) a gp120 inhibitor, e.g., BMS-488043 and BlockAide/CR, 10) a G6PD and NADH-oxidase inhibitor, e.g., immunitin, 10) a CCR5 inhibitor, e.g., aplaviroc, vicriviroc, INCB9471, PRO-140, INCB15050, PF-232798, CCR5 mAb004, and maraviroc, 11) an interferon, e.g., pegylated rIFN-alpha 2b, pegylated rIFN-alpha 2a, rIFN-alpha 2b, IFN alpha-2b XL, rIFN-alpha 2a, consensus IFN alpha, infergen, rebif, locteron, AVI-005, PEG-infergen, pegylated IFN-beta, oral interferon alpha, feron, reaferon, intermax alpha, r-IFN-beta, infergen+actimmune, IFN-omega with DUROS, and albuferon, 12) ribavirin analogs, e.g., rebetol, copegus, VX-497, and viramidine (taribavirin) 13) NS5a inhibitors, e.g., A-831, A-689 and BMS-790052, 14) NS5b polymerase inhibitors, e.g., NM-283, valopicitabine, R1626, PSI-6130 (R1656), HCV-796, BILB 1941, MK-0608, NM-107, R7128, VCH-759, PF-868554, GSK625433, and XTL-2125, 15) NS3 protease inhibitors, e.g., SCH-503034 (SCH-7), VX-950 (Telaprevir), ITMN-191, and BILN-2065, 16) alpha-glucosidase 1 inhibitors, e.g., MX-3253 (celgosivir) and UT-231B, 17) hepatoprotectants, e.g., IDN-6556, ME 3738, MitoQ, and LB-84451, 18) mevalonate decarboxylase antagonists, e.g., statins, HMGCoA synthase inhibitors (e.g., hymeglusin), squalene synthesis inhibitors (e.g., zaragozic acid), 19) angiotensin II receptor antagonists, e.g. losartan, irbesartan, olmesartan, candesartan, valsartan, telmisartan, eprosartan, 20) angiotensin-converting enzyme inhibitors, e.g., captopril, zofenopril, enalapril, ramipril, quinapril, perindopril, lisinopril, benazepril, fosinopril, 21) other anti-fibrotic agents, e.g., amiloride and endothelin antagonists, e.g. bosentan and ambrisentan, 22) non-nucleoside inhibitors of HCV, e.g., benzimidazole derivatives, benzo-1,2,4-thiadiazine derivatives, and phenylalanine derivatives, 23) other drugs for treating HCV, e.g., zadaxin, nitazoxanide (alinea), BIVN-401 (virostat), DEBIO-025, VGX-410C, EMZ-702, AVI 4065, bavituximab, oglufanide, PYN-17, KPE02003002, actilon (CPG-10101), KRN-7000, civacir, GI-5005, ANA-975, XTL-6865, ANA 971, NOV-205, tarvacin, EHC-18, and NIM811, 24) pharmacokinetic enhancers, e.g., BAS-100, cobicistat and SP1452, 25)RNAse H inhibitors, e.g., ODN-93 and ODN-112, 24) other anti-HIV agents, e.g., VGV-1, PA-457 (bevirimat), ampligen, HRG214, cytolin, polymun, VGX-410, KD247, AMZ 0026, CYT 99007, A-221 HIV, BAY 50-4798, MDX010 (iplimumab), PBS119, ALG889, and PA-1050040.

It is also possible to combine any compound of the invention with one or more other active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g. in separate tablets, pills or capsules, or by different injections in separate syringes. In general, during alternation therapy, an effective dosage of each active ingredient is administered sequentially, i.e. serially, whereas in combination therapy, effective dosages of two or more active ingredients are administered together. A synergistic anti-viral effect denotes an antiviral effect which is greater than the predicted purely additive effects of the individual compounds of the combination.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, whereby HCV polymerase is inhibited. In a preferred aspect of this embodiment, the compound of Formula I-IV is at least 70% a single diastereomer, 80% a single diastereomer, 90% a single diastereomer or most preferably 95% a single diastereomer.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent, whereby HCV polymerase is inhibited. In a preferred aspect of this embodiment, the compound of Formula I-IV is at least 70% a single diastereomer, 80% a single diastereomer, 90% a single diastereomer or most preferably 95% a single diastereomer.

In still yet another embodiment, the present application provides for methods of inhibiting HCV polymerase in a cell, comprising: contacting a cell infected with HCV with an effective amount of a compound of Formula I-IV, or a pharmaceutically acceptable salt, solvate, and/or ester thereof, and at least one additional active therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV. In a preferred aspect of this embodiment, the compound of Formula I-IV is at least 70% a single diastereomer, 80% a single diastereomer, 90% a single diastereomer or most preferably 95% a single diastereomer.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof. In a preferred aspect of this embodiment, the compound of Formula I-IV is, at least, 70% a single diastereomer, 80% a single diastereomer, 90% a single diastereomer or most preferably 95% a single diastereomer.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent, whereby HCV polymerase is inhibited. In a preferred aspect of this embodiment, the compound of Formula I-IV is, at least, 70% a single diastereomer, 80% a single diastereomer, 90% a single diastereomer or most preferably 95% a single diastereomer.

In still yet another embodiment, the present application provides for methods of treating HCV in a patient, comprising: administering to the patient a therapeutically effective amount of a compound of Formula I-IV, or a pharmaceutically acceptable salt, solvate, and/or ester thereof, and at least one additional active therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV. In a preferred aspect of this embodiment, the compound of Formula I-IV is, at least, 70% a single diastereomer, 80% a single diastereomer, 90% a single diastereomer or most preferably 95% a single diastereomer.

In still yet another embodiment, the present application provides for the use of a compound of Formula I-IV, or a pharmaceutically acceptable salt, solvate, and/or ester thereof, for the preparation of a medicament for treating an HCV infection in a patient. In a preferred aspect of this embodiment, the compound of Formula I-IV is, at least, 70% a single diastereomer, 80% a single diastereomer, 90% a single diastereomer or most preferably 95% a single diastereomer.

In still yet another embodiment, the present application provides for the use of a compound of Formula I-IV, or a pharmaceutically acceptable salt, solvate, and/or ester thereof, for treating an HCV infection. In a preferred aspect of this embodiment, the compound of Formula I-IV is, at least, 70% a single diastereomer, 80% a single diastereomer, 90% a single diastereomer or most preferably 95% a single diastereomer.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $^{14}C$ or $^{3}H$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no HCV polymerase inhibitory activity of their own.

Recipes and methods for determining stability of compounds in surrogate gastrointestinal secretions are known. Compounds are defined herein as stable in the gastrointestinal tract where less than about 50 mole percent of the protected groups are deprotected in surrogate intestinal or gastric juice upon incubation for 1 hour at 37° C. Simply because the compounds are stable to the gastrointestinal tract does not mean that they cannot be hydrolyzed in vivo. The prodrugs of the invention typically will be stable in the digestive system but may be substantially hydrolyzed to the parental drug in the digestive lumen, liver or other metabolic organ, or within cells in general.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
|---|---|
| Ac₂O | acetic anhydride |
| AIBN | 2,2'-azobis(2-methylpropionitrile) |
| Bn | benzyl |
| BnBr | benzylbromide |
| BSA | bis(trimethylsilyl)acetamide |
| BzCl | benzoyl chloride |
| CDI | carbonyl diimidazole |
| DABCO | 1,4-diazabicyclo[2.2.2]octane |
| DBN | 1,5-diazabicyclo[4.3.0]nonene-5 |
| DDQ | 2,3-dichloro-5,6-dicyano-1,4-benzoquinone |

TABLE 1-continued

List of abbreviations and acronyms.

| Abbreviation | Meaning |
|---|---|
| DBU | 1,5-diazabicyclo[5.4.0]undecene-5 |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH⁺ | mass plus 1 |
| MH⁻ | mass minus 1 |
| MsOH | methanesulfonic acid |
| MS or ms | mass spectrum |
| MTBE | methyl t-butyl ether |
| NBS | N-bromosuccinimide |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| δ | parts per million down field from tetramethylsilane |

Preparation of Compounds

Compound 1a-1f

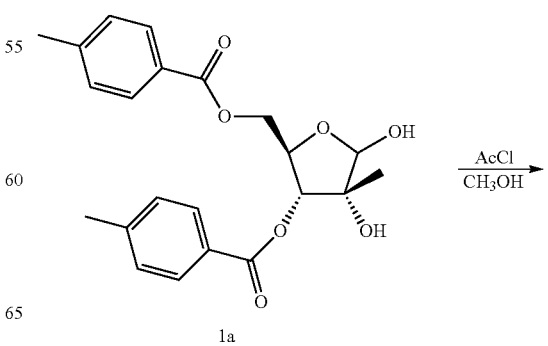

1a

67

-continued

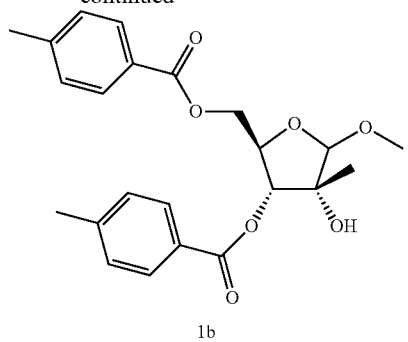

1b

To a solution of 1a (22.0 g, 54.9 mmol, prepared according to the procedures described in *J.O.C.*, 2004, 6257) in methanol (300 mL) was dropwise added acetyl chloride (22 mL) at 0° C. using a dropping funnel over a period of 30 min and then stirred at room temperature for 16 h. The mixture was concentrated, re-dissolved in ethyl acetate (400 mL), washed with ice-cold 2 N NaOH, and concentrated to dryness, affording the crude methyl ether 1b as an oil. MS=437.2 (M+Na⁺).

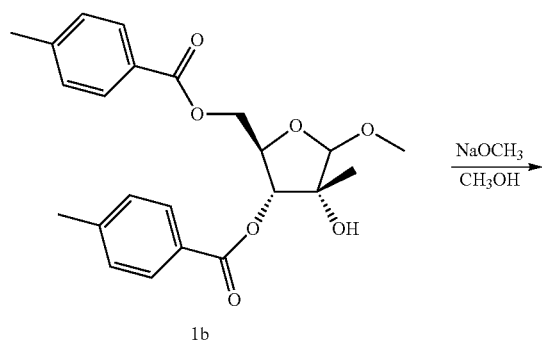

To a solution of 1b (obtained from the previous step) in methanol (300 mL) was added 0.5 M sodium methoxide solution in methanol (20 mL, 10 mmol), and stirred for 16 h at room temperature. The reaction was quenched with 4.0 N HCl solution in dioxane (2.5 mL, 10 mmol). The mixture was then concentrated, affording the crude 1c. MS=201.0 (M+Na⁺).

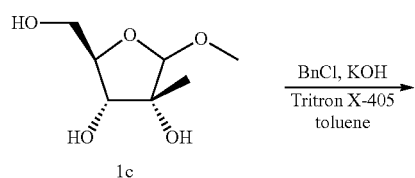

68

-continued

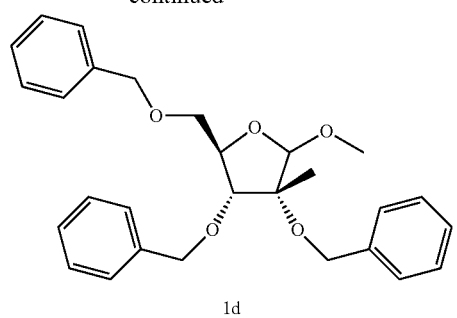

1d

A mixture of 1c (obtained from the previous step), Tritron X-405 (70% in water, 6.0 g), 50% KOH (in water, 85 g) in toluene (500 mL) was heated to reflux with a Dean-Stark trap attached. After 1 h collecting ~25 mL of water, benzyl chloride (33 g, 260 mmol) was added and continued to reflux with stirring for 16 h. The mixture was then cooled and partitioned between ethyl acetate (400 mL) and water (300 mL). The organic layer was washed with water (300 mL), and concentrated. The residue was purified by silica gel column chromatography (~20% EtOAc/hexanes), affording the methyl ether 1d as an oil (22.0 g, 89% in three steps). $^1$H NMR (300 MHz, CDCl$_3$): 7.3 (m, 15H), 4.5-4.9 (m, 7H), 4.37 (m, 1H), 3.87 (d, 1H), 3.56 (m, 2H), 3.52 (s, 3H), 1.40 (s, 3H).

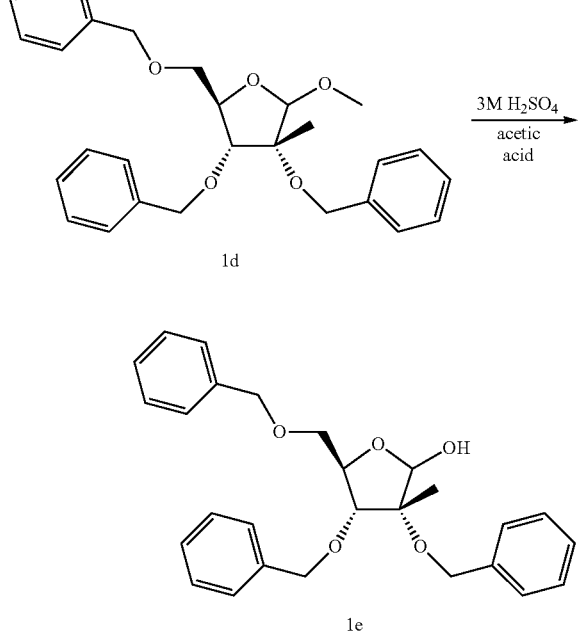

To a solution of id (22.0 g, 49.0 mmol) in acetic acid (110 mL) was added ~3 M sulfuric acid (prepared by mixing 4.8 g of concentrated sulfuric acid with 24 mL of water) and stirred at 70° C. for 8 h. The mixture was concentrated to a volume of ~20 mL, and partitioned between ethyl acetate and ice-cold 2N NaOH. The ethyl acetate layer was concentrated, and purified by silica gel column chromatography (~35% EtOAc/hexanes), affording 1e as an oil (17.0 g, 80%). MS=457.2 (M+Na⁺).

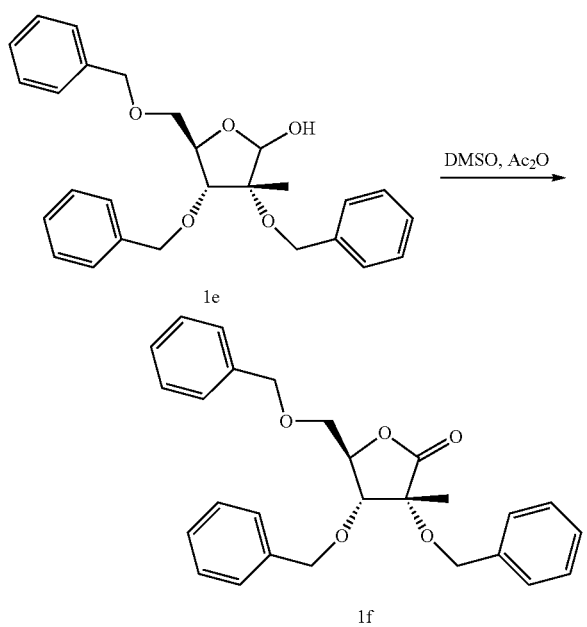

To a solution of 1e (45 g, 104 mmol) in DMSO (135 mL) was dropwise added acetic anhydride (90 mL, 815 mmol) at room temperature under argon. The mixture was stirred for 16 h at room temperature, and then poured into ice-water (1 L) while stirring. After ice was completely melted (~30 min), ethyl acetate (~500 mL) was added. The organic layer was separated. This extraction process was repeated three times (3×500 mL). The organic extracts were combined and concentrated. The residue was purified by silica gel column chromatography (~20% EtOAc/hexanes), affording 1f as an oil (39 g, 88%). $^1$H NMR (300 MHz, DMSO-d$_6$): δ 7.3 (m, 15H), 4.4-4.8 (m, 7H), 4.08 (d, J=7.5 Hz, 1H), 3.75 (dd, J=2.4, 11.4 Hz, 1H), 3.64 (dd, J=5.4, 11.4 Hz, 1H), 1.51 (s, 3H).

Compound 2

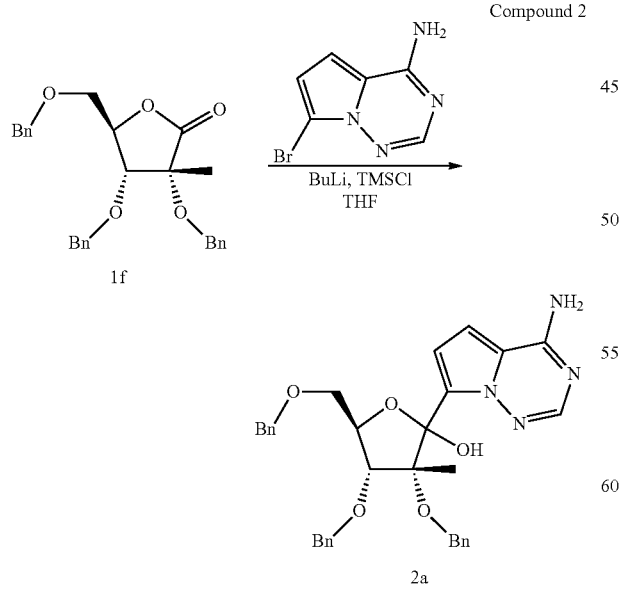

To a dry, argon purged round bottom flask (100 mL) were added 7-bromo-pyrrolo[2,1-f][1,2,4]triazin-4-ylamine (234 mg, 1.10 mmol) (prepared according to WO2007056170) and anhydrous THF (1.5 mL). TMSCl (276 μL, 2.2 mmol) was then added and the reaction mixture stirred for 2 h. The flask was placed into a dry ice/acetone bath (~−78° C.) and BuLi (2.5 mL, 4.0 mmol, 1.6M in hexanes) was added dropwise. After 1 h, a solution of 1f (432.5 mg, 1.0 mmol) in THF was cooled to 0° C. and then added to the reaction flask dropwise. After 1 h of stirring at −78° C., the flask was warmed to 0° C. and sat. NH$_4$Cl (5 mL) was added to quench the reaction. The organics were extracted using EtOAc (3×10 mL) and the combined organic layers were dried using MgSO$_4$. The solvent was removed under reduced pressure and the crude material was purified using flash chromatography (hexanes/EtOAc). 560 mg (90%) of 2a was isolated as a mixture of two anomers. LC/MS=567.2 (M+H$^+$). $^1$H NMR (300 MHz, CDCl$_3$): δ 7.85 (m, 1H), 7.27 (m, 15H), 7.01 (m, 1H), 6.51 (m, 1H), 4.66 (m, 8H), 4.40 (m, 2H), 3.79 (m, 3H), 1.62 (s, 2'-CH$_3$ from the one anomer), 1.18 (s, 2'-CH$_3$ from the other anomer).

Alternative Procedures for 2a

To a dry, argon purged round bottom flask were added 7-bromo-pyrrolo[2,1-f][1,2,4]triazin-4-ylamine (9.6 g, 45 mmol) and anhydrous THF (60 mL). TMSCl (12.4 mL, 99 mmol) was then added and the reaction mixture stirred for 2 h. The flask was placed into a dry ice/acetone bath (~−78° C.) and BuLi (98 mL, 158 mmol, 1.6M in hexanes) was added dropwise. After 1 h, this reaction mixture was added to a solution of 1f (13.0 g, 30 mmol) in THF at −78° C. via cannula. After 2 h of stirring at −78° C., the flask was warmed to 0° C. Saturated NH$_4$Cl (150 mL) was added to quench the reaction. The organics were extracted using EtOAc (3×100 mL) and the combined organic layers were dried using MgSO$_4$. The solvent was removed under reduced pressure and the crude material was purified using flash silica gel chromatography (hexanes/EtOAc). 7.5 g (44%) of the desired material 2a was isolated. LC/MS 567.2 (M+H$^+$).

Compound 5

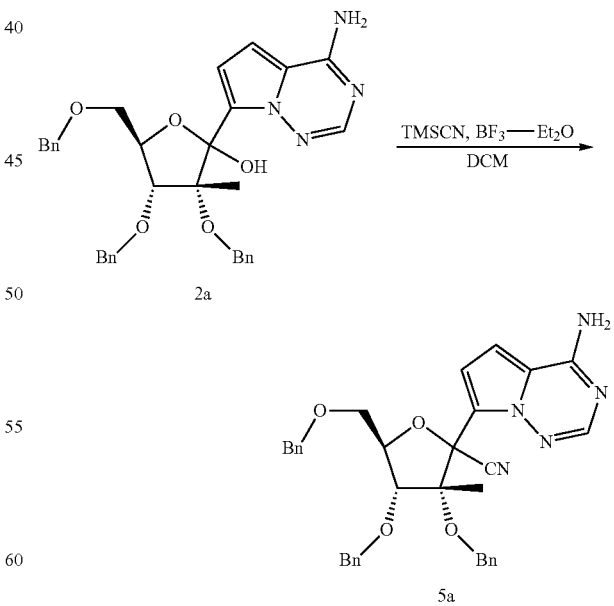

To a solution of compound 2a (1 g, 1.77 mmol) in CH$_2$Cl$_2$ (20 mL) at 0° C. was added TMSCN (1.4 mL, 10.5 mmol) and BF$_3$-Et$_2$O (1 mL, 8.1 mmol). The reaction mixture was stirred at 0° C. for 0.5 h, then at room temperature for additional 0.5 h. The reaction was quenched with NaHCO₃ at 0° C., and diluted with CH₃CO₂Et. The organic phase was separated, washed with brine, dried over Na₂SO₄, filtered and concentrated. The residue was purified by chromatography on silica gel, eluted with CH₃CO₂Et-hexanes (1:1 to 2:1), to give the desired compound 5a (620 mg, 61%) as an isomeric mixture. MS=576.1 (M+H⁺).

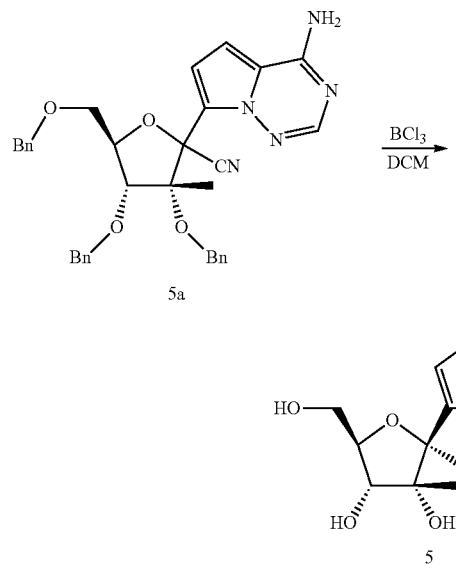

5a

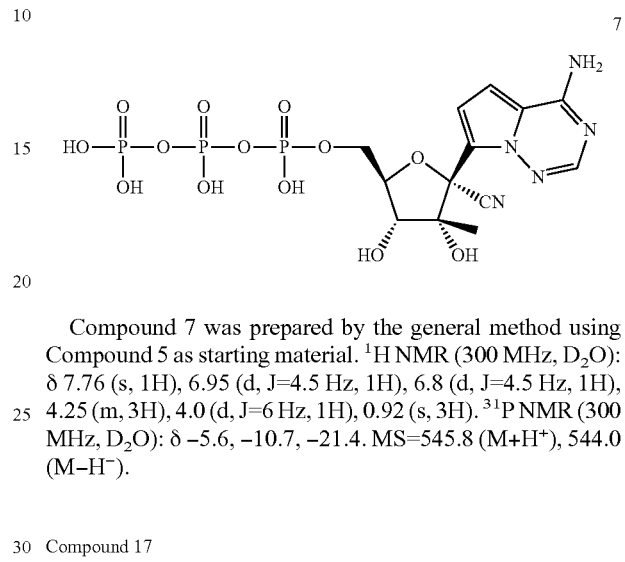

To a solution of compound 5a (150 mg, 0.26 mmol) in CH₂Cl₂ (4 mL) at −78° C. was added BCl₃ (2 mL, 1M in CH₂Cl₂). The reaction mixture was stirred at −78° C. for 1 h. The reaction was quenched at −78° C. by dropwise addition of TEA (2 mL) and MeOH (5 mL). The mixture was allowed to warm up to room temperature, evaporated, and co-evaporated with MeOH several times. The residue was treated with NaHCO₃ (1 g in 10 mL H₂O), concentrated and purified by HPLC to give the desired product Compound 5 (48 mg, 60%). ¹H NMR (300 MHz, D₂O): δ 7.74 (s 1H), 6.76 (d, J=5 Hz, 1H), 6.73 (d, J=5 Hz, 1H), 4.1 (m, 1H), 3.9 (m, 1H), 3.8 (m, 2H), 0.84 (s, 3H). MS=305.9 (M+H⁺). The other alpha-anomer was also obtained (9 mg, 11%): ¹H NMR (300 MHz, D₂O): δ 7.70 (s 1H), 6.8 (d, J=5 Hz, 1H), 6.7 (d, J=5 Hz, 1H), 4.25 (d, J=9 Hz, 1H), 4.07 (m, 1H), 3.85 (m, 1H), 3.7 (m, 1H), 1.6 (s, 3H). MS=306.1 (M+H⁺).

General Procedure for Preparation of a Nucleoside Triphosphate:

To a pear-shaped flask (5-15 mL) is charged with a nucleoside (~20 mg). Trimethyl phosphate (0.5-1.0 mL) is added. The solution is cooled with ice-water bath. POCl₃ (40-45 mg) is added and stirred at 0° C. until the reaction is complete (1 to 4 h; the reaction progress is monitored by ion-exchange HPLC; analytical samples are prepared by taking ~3 uL of the reaction mixture and diluting it with 1.0 M Et₃NH₂CO₃ (30-50 uL)). A solution of pyrophosphate-Bu₃N (250 mg) and Bu₃N (90-105 mg) in acetonitrile or DMF (1-1.5 mL) is then added. The mixture is stirred at 0° C. for 0.3 to 2.5 h, and then the reaction is quenched with 1.0 M Et₃NH₂CO₃ (~5 mL). The resulting mixture is stirred for additional 0.5-1 h while warming up to room temperature. The mixture is concentrated to dryness, re-dissolved in water (4 mL), and purified by ion exchange HPLC. The fractions containing the desired product is concentrated to dryness, dissolved in water (~5 mL), concentrated to dryness, and again dissolved in water (~5 mL). NaHCO₃ (30-50 mg) is added and concentrated to dryness. The residue is dissolved in water and concentrated to dryness again. This process is repeated 2-5 times. The residue is then subjected to C-18 HPLC purification, affording the desired product as a sodium salt.

Compound 7

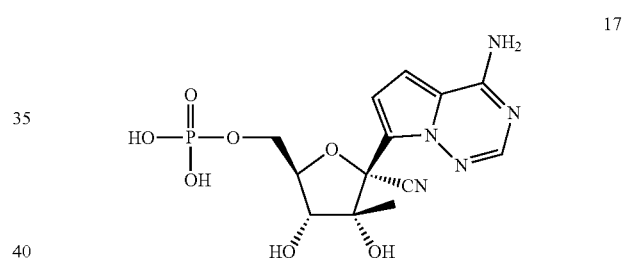

Compound 7 was prepared by the general method using Compound 5 as starting material. ¹H NMR (300 MHz, D₂O): δ 7.76 (s, 1H), 6.95 (d, J=4.5 Hz, 1H), 6.8 (d, J=4.5 Hz, 1H), 4.25 (m, 3H), 4.0 (d, J=6 Hz, 1H), 0.92 (s, 3H). ³¹P NMR (300 MHz, D₂O): δ −5.6, −10.7, −21.4. MS=545.8 (M+H⁺), 544.0 (M−H⁻).

Compound 17

17

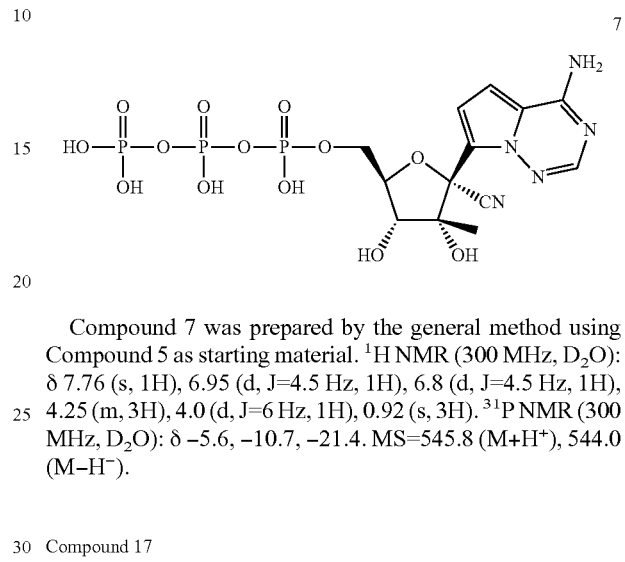

A mixture of about 0.05 mmol of Compound 5 and about 0.5 mL of trimethylphosphate is sealed in a container for about one to about 48 hours. The mixture is cooled to about −10 to about 10° C. and about 0.075 mmol of phosphorous oxychloride is added. After about one to about 24 hours, the reaction is quenched with about 0.5 mL of 1M tetraethylammonium bicarbonate and the desired fraction are isolated by anion exchange chromatography. The appropriate fractions are then desalted by reverse-phase chromatography to give Compound 17.

Mono Phosphoramidate Prodrugs

Non-limiting examples of mono-phosphoramidate prodrugs comprising the instant invention may be prepared according to general Scheme 1.

Scheme 1

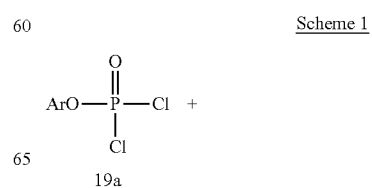

19a

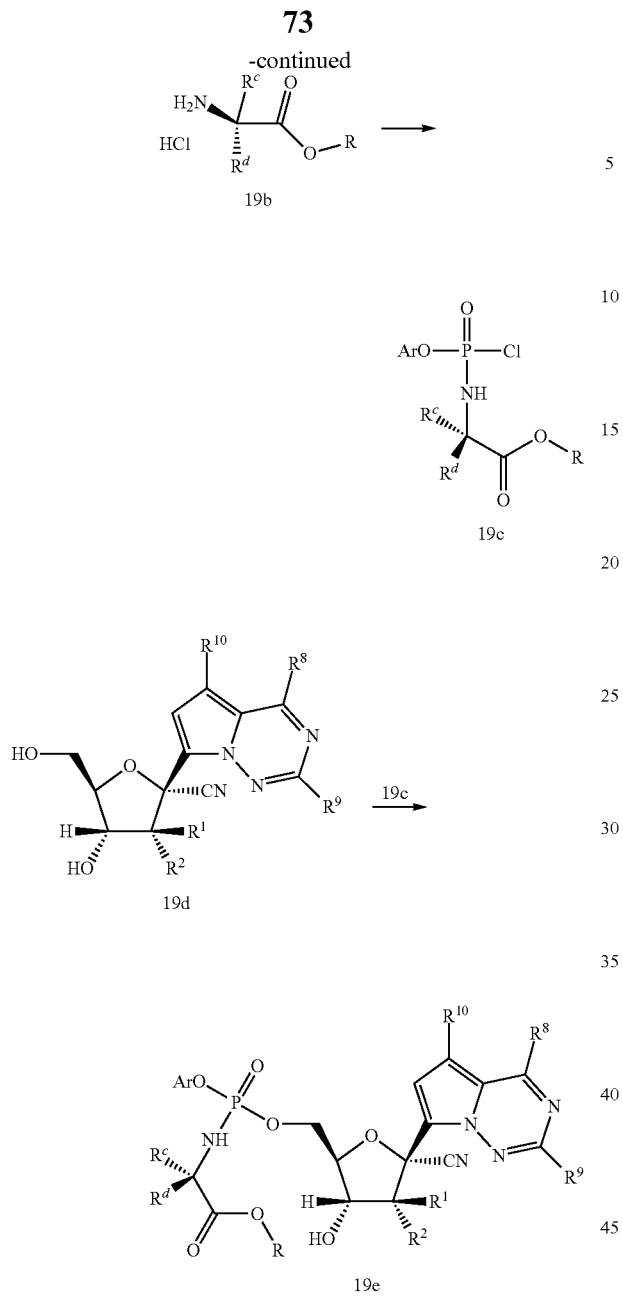

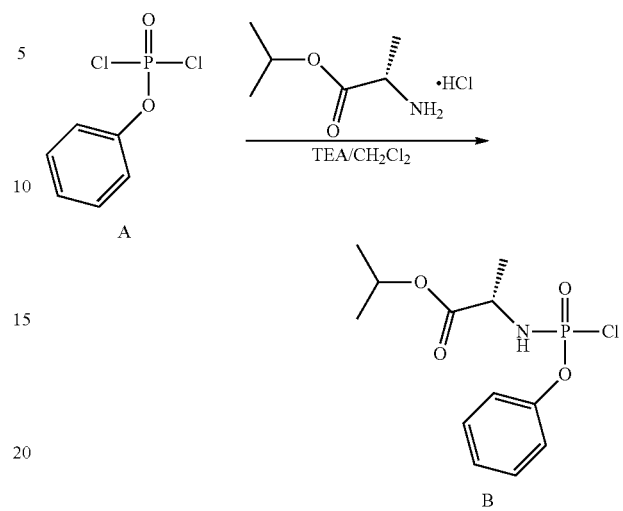

Preparation of Phosphoramidyl Chlorides

Compound A (commercially available, 4.99 g, 23.8 mmol) was dissolved in dichloromethane (100 mL) and alanine isopropyl ester hydrochloride (3.98 g, 23.8 mmol) was added. The resulting clear solution was cooled −78° C. for 30 min. Triethylamine (6.63 mL, 47.5 mmol) was added dropwise over 15 min. The mixture was then allowed to warm to room temperature. After 16 h, the solvent was removed by argon stream. The residue was re-dissolved in MTBE (25 mL) and the insoluble was removed by filtration under argon. The filtrate was then condensed by argon stream and the crude product B was used for the next reaction without further purification. $^1$H NMR (300 MHz, CDCl$_3$): 7.1-7.4 (m, 5H), 5.1 (m, 1H), 4.35 (m, 1H), 4.15 (m, 1H), 1.5 (d, 3H), 1.2 (m, 6H). $^{31}$P NMR (121.4 MHz, CDCl$_3$): δ 7.8 and 8.4 (2s).

Preparation of Compound 6

The general procedure comprises the reaction of an amino acid ester salt 19b, e.g., HCl salt, with an aryl dichlorophosphate 19a in the presence of about two to ten equivalents of a suitable base to give the phosphoramidate 19c. Suitable bases include, but are not limited to, imidazoles, pyridines such as lutidine and DMAP, tertiary amines such as triethylamine and DABCO, and substituted amidines such as DBN and DBU. Tertiary amines are particularly preferred. Preferably, the product of each step is used directly in the subsequent steps without recrystallization or chromatography. Specific, but non-limiting, examples of 19a, 19b, and 19c can be found in WO 2006/121820 that is hereby incorporated by reference in its entirety. A nucleoside base 19d reacts with the phosphoramidate 19c in the presence of a suitable base. Suitable bases include, but are not limited to, imidazoles, pyridines such as lutidine and DMAP, tertiary amines such as triethylamine and DABCO, and substituted amidines such as DBN and DBU. The product 19e may be isolated by recrystallization and/or chromatography.

To a solution of compound 5 (1.03 g, 3.37 mmol) in trimethyl phosphate (2.0 mL) and THF (20 mL) was added N-methyl imidazole (1.5 g, 18.3 mmol) at 0° C. A solution of compound B (2.5 g, 8.18 mmol) in THF (3 mL) was dropwise added. The resulting mixture was allowed to warm to room temperature over 1.5 h. The mixture was partitioned between ethyl acetate and water. The ethyl acetate layer was concentrated and the residue was purified by silica gel chromatography (ethyl acetate to 10% ethanol/ethyl acetate), affording 1.15 g (59%) of compound 6 as 1:1 diastereomeric mixture at phosphorous. $^1$H NMR (300 MHz, CDCl$_3$): δ 8.02 (s, 1H), 7.1-7.4 (m, 5H), 6.8 (2d, 1H), 6.7 (2d, 1H), 6.08 (brs, 2H), 5.03 (m, 1H), 4.6 (m, 1H), 4.4 (m, 2H), 3.9-4.1 (m, 3H), 1.31 (d, 3H), 1.2 (m, 6H), 0.83 (s, 3H). $^{31}$P NMR (121.4 MHz, CDCl$_3$): δ 2.78 (s). MS=575.1 (M+H$^+$).

Using the general procedures described for the preparation of Compound 6, Compounds 20-29 were prepared.

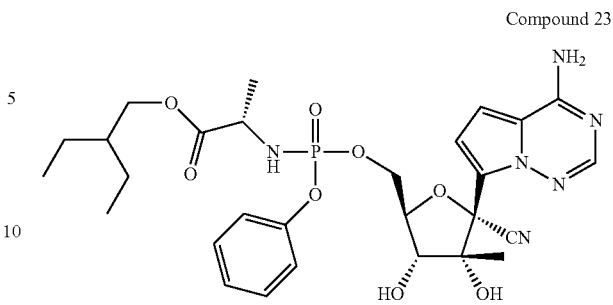
Compound 23

Compound 23: $^{31}$P NMR (162.1 MHz, CDCl$_3$): δ 2.72, 2.72. MS=617.2 (M+H$^+$).

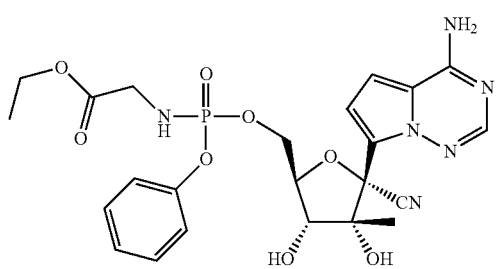
Compound 20

Compound 20: $^{31}$P NMR (121.4 MHz, CDCl$_3$): δ 3.76, 3.80. MS=547.0 (M+H$^+$).

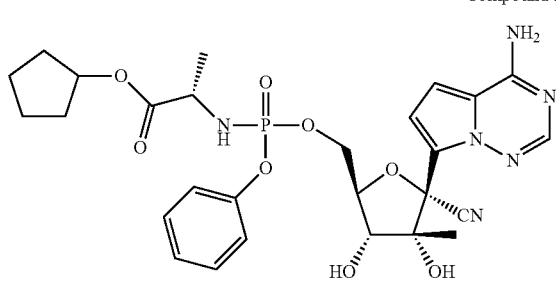
Compound 24

Compound 24: $^{31}$P NMR (162.1 MHz, CDCl$_3$): δ 2.92. MS=601.2 (M+H$^+$).

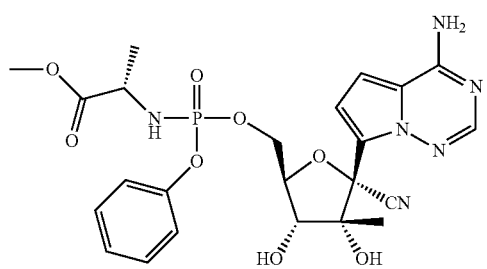
Compound 21

Compound 21: $^{31}$P NMR (162.1 MHz, CDCl$_3$): δ 2.64, 2.68. MS=547.1 (M+H$^+$).

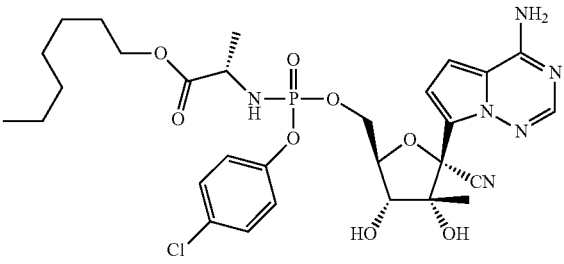
Compound 25

Compound 25: $^{31}$P NMR (162.1 MHz, CDCl$_3$): δ 2.82. MS=665.4 (M+H$^+$).

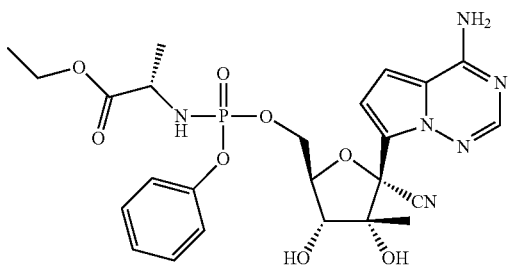
Compound 22

Compound 22: $^{31}$P NMR (162.1 MHz, CDCl$_3$): δ 3.81, 3.94. MS=561.1 (M+H$^+$).

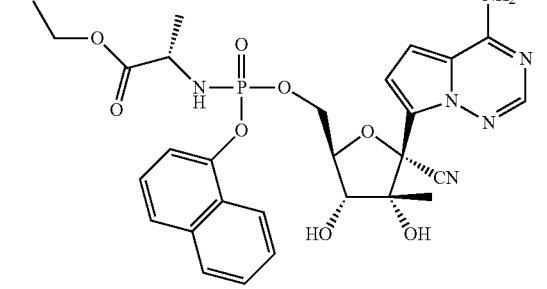
Compound 26

Compound 26: $^{31}$P NMR (121.4 MHz, CDCl$_3$): δ 3.04. MS=611.1 (M+H$^+$).

Compound 27

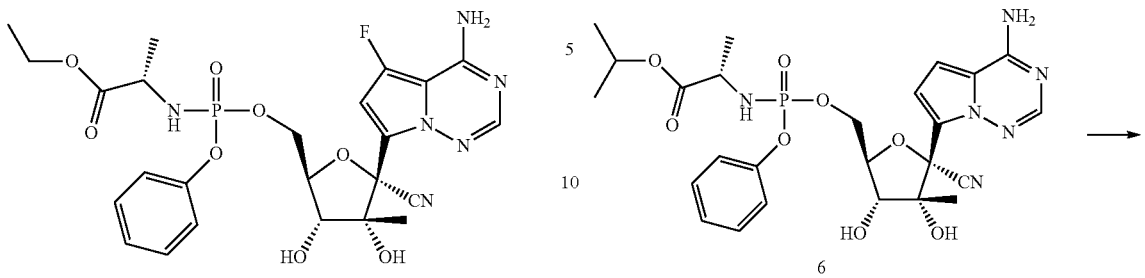

Compound 27: ³¹P NMR (162.1 MHz, CDCl₃): δ 2.75, 2.83. MS=579.0 (M+H⁺).

Compound 28

Compound 28: ³¹P NMR (162.1 MHz, CD₃OD): δ 3.83. MS=579.0 (M+H⁺).

Compound 29

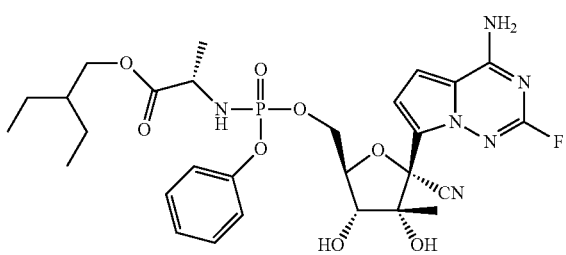

Compound 29: ³¹P NMR (121.4 MHz, CDCl₃): δ 3.71, 2.75. MS=633.3 (M−H⁺).

Preparation of Compound 8

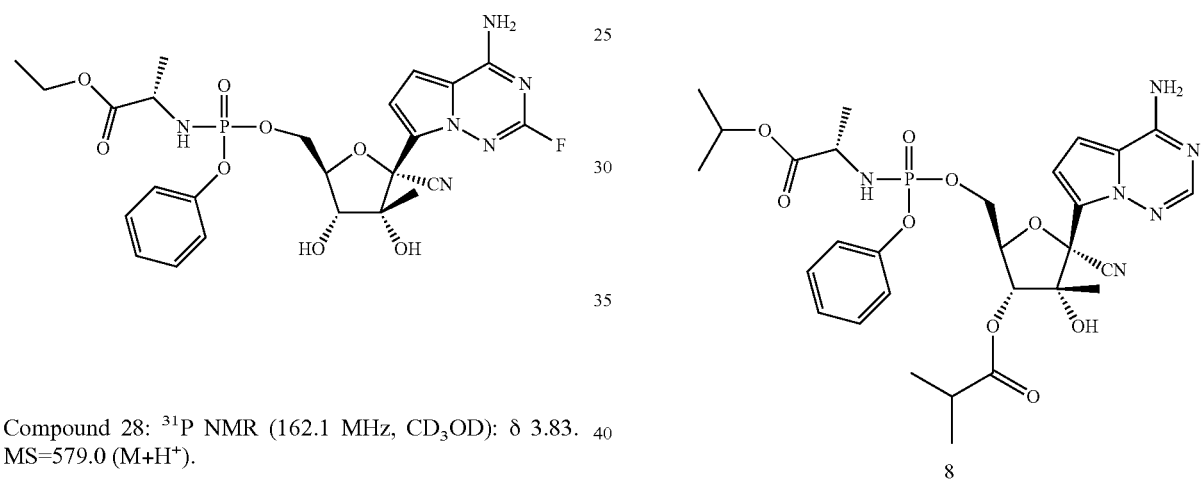

To a solution of compound 6 (175 mg, 0.305 mmol) in acetonitrile (2 mL) was added N,N-dimethyformamide dimethyl acetal (41 uL, 0.34 mmol, 1.1 eq.) and stirred at room temperature for 1 h. The reaction was complete (by LCMS). The mixture was then concentrated to dryness. To the residue were added DCC (250 mg, 1.21 mmol, 4 eq.), acetonitrile (5 mL) and isobutyric acid (55 mg, 58 uL, 2 eq.). The mixture was stirred at room temperature for 48 h. Water (0.2 mL) and trifluoroacetic acid (0.1 mL) were added at 0° C. and stirred at room temperature for 64 h. Sodium bicarbonate (500 mg) was added at 0° C. The mixture was stirred at room temperature for 0.5 h and filtered. The filtrate was concentrated and the residue was purified by silica gel column chromatography (5% methanol/dichloromethane), affording 144 mg (73%) of compound 8 as 1:1 diastereomeric mixture at phosphorus. ¹H NMR (300 MHz, CDCl₃): δ 8.00 (s, 1H), 7.1-7.4 (m, 5H), 6.83 (d, 1H), 6.71 (2d, 1H), 5.97 (brs, 2H), 5.94 (d, 1H), 5.07 (2d, 1H), 5.01 (m, 1H), 4.68 (m, 1H), 4.4 (m, 2H), 4.0 (m, 2H), 2.74 (m, 1H), 1.4 (2d, 3H), 1.2-1.3 (12H), 0.98 and 0.99 (2s, 3H). ³¹P NMR (121.4 MHz, CDCl₃): δ 2.56 and 2.65 (2s). MS=645.1 (M+H⁺).

Chiral Column Separation of the Two Diastereoisomers of Compound 8

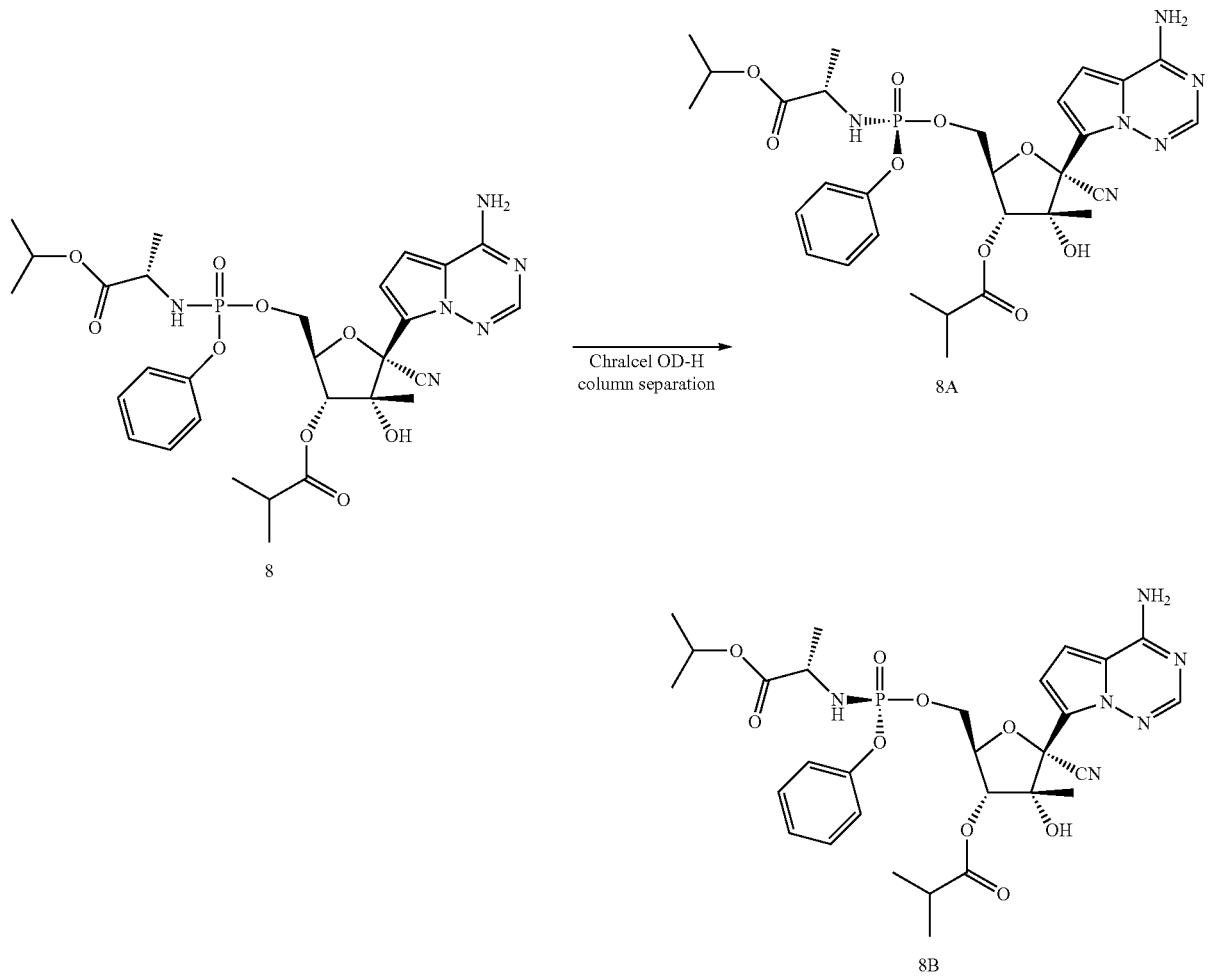

Compound 8 was dissolved in heptane and isopropanol (70%:30%, 230 mg in 4.5 mL of the mixed solvents) and subjected to chiral column separation to afford compound 8A and 8B under the following conditions;

Column: Chiralcel OD-H, 2×25 cm

Solvent system: 70% heptane and 30% isopropanol

Flow rate: 6 mL/min.

Loading volume per run: 2.5 mL

Compound 8A: retention time 20 min. $^1$H NMR (300 MHz, CDCl$_3$): δ 8.00 (s, 1H), 7.1-7.3 (m, 5H), 6.83 (d, 1H), 6.71 (d, 1H), 6.09 (brs, 2H), 5.95 (s, 1H), 5.04 (m, 2H), 4.67 (q, 1H), 4.35-4.52 (m, 2H), 4.00 (m, 2H), 2.74 (m, 1H), 1.40 (d, 3H), 1.2-1.3 (12H), 0.98 (s, 3H). $^{31}$P NMR (121.4 MHz, CDCl$_3$): δ 2.72 (s). Compound 8A was subsequently recrystallized from MTBE for x-ray quality crystals.

Compound 8B: retention time 50 min. $^1$H NMR (300 MHz, CDCl$_3$): δ 7.98 (s, 1H), 7.1-7.3 (m, 5H), 6.83 (d, 1H), 6.73 (d, 1H), 6.02 (brs, 2H), 5.95 (s, 1H), 5.08 (d, 1H), 5.00 (m, 1H), 4.68 (q, 1H), 4.38-4.56 (m, 2H), 3.98 (m, 2H), 2.74 (m, 1H), 1.40 (d, 3H), 1.2-1.3 (12H), 0.99 (s, 3H). $^{31}$P NMR (121.4 MHz, CDCl$_3$): δ 2.61 (s).

Compound 40

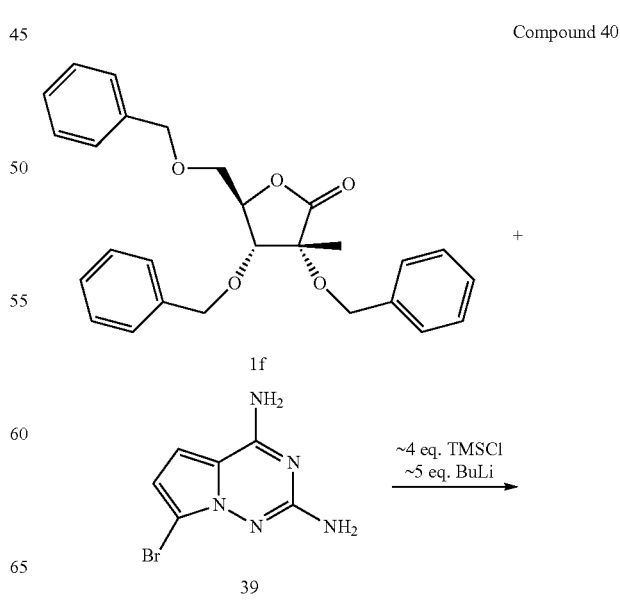

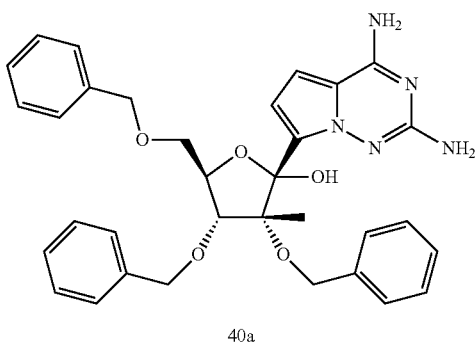

40a

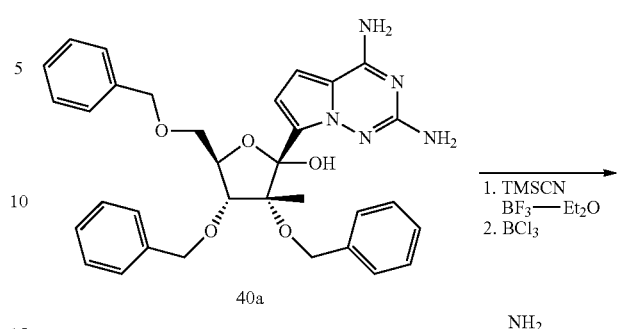

40a

A solution of about one part of 39 and about four parts of trimethylsilylchloride in THF is stirred at about 20 to about 60° C. for about 30 min to about six hours. The solution is cooled to about −70 to about −100° C. and a solution of about five parts of butyllithium in hexanes is added. After about 30 min. to about three hours, the reaction is allowed to warm to about 0° C. over about three hours. The reaction is quenched with saturated NaHCO$_3$ and the mixture is extracted with ether. The ether extracts are washed with brine, dried, and the solvent evaporated to give 40a which may be further purified by chromatography.

Compound 41 may be prepared from Compound 40a in the same manner as Compound 5 was prepared from Compound 2a.

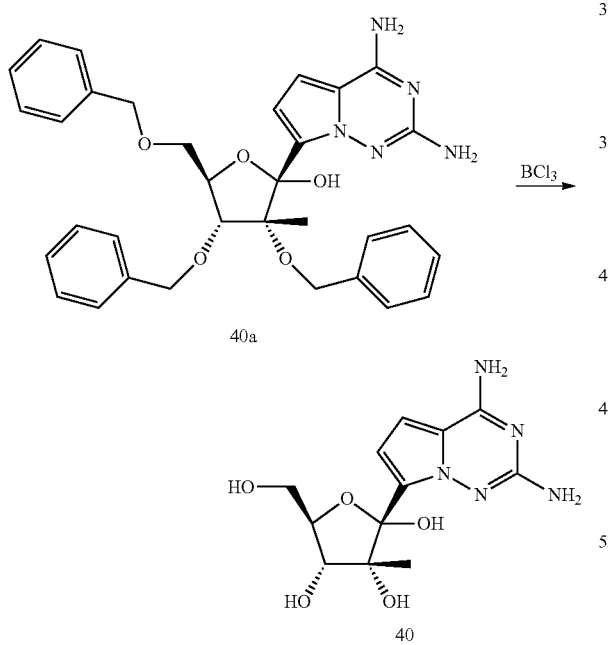

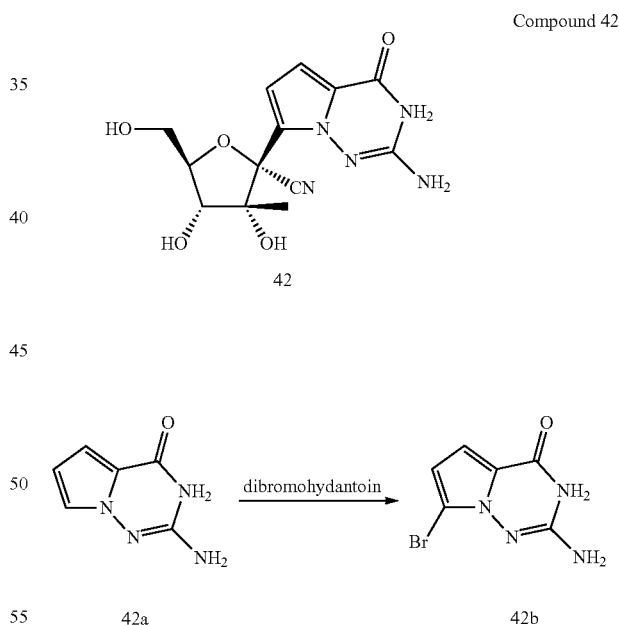

A solution of one part of 40a in dichloromethane is cooled to about −100 to about −70° C. A 1.0 M solution of BCl$_3$ in dichloromethane (about 10 to 20 parts) is added and the reaction is stirred for about 30 min. to about 3 hours. A mixture of pyridine and methanol (about 1:2) is then added to quench the reaction. The resulting mixture is slowly warmed to room temperature and concentrated. The residue is suspended in about 27% ammonium hydroxide and concentrated. This process is repeated twice. The residue is re-dissolved in methanol and concentrated. This process is repeated once. The residue is purified by RP-HPLC to give 40.

A solution of about one part Compound 42a (Path, et al.; Journal of Heterocyclic Chemistry 1994, 31(4), 781-6) in anhydrous DMF is cooled to about −20° C. and about 0.5 parts of 1,3-diromo-5,5-dimethylhydantoin is added in portions. After about one to about 24 hours, a saturate aqueous sodium bisulfate solution is added and the solids are collected by filtration. The solids are partitioned between ethyl acetate and dilute aqueous sodium carbonate. The organic phase is washed with dilute sodium carbonate then dried and concentrated to give Compound 42b.

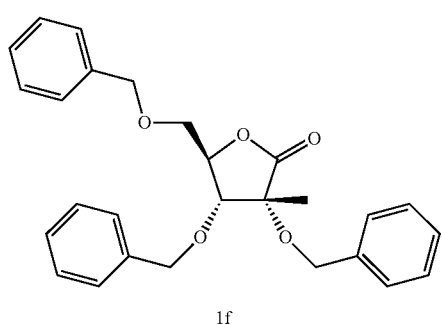

1f

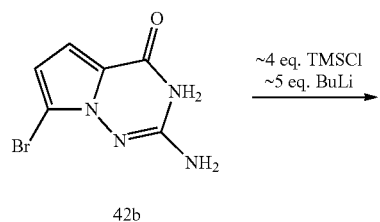

42b

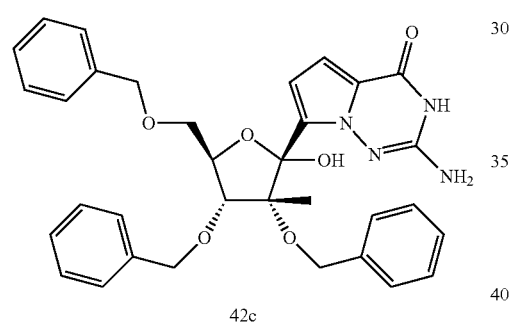

42c

A solution of about one part of 42b and about four parts of trimethylsilylchloride in THF is stirred at about 20 to about 60° C. for about 30 min to about six hours. The solution is cooled to about −70 to about −100° C. and a solution of about five parts of butyllithium in hexanes is added. After about 30 min. to about three hours, the reaction is allowed to warm to about 0° C. over about three hours. The reaction is quenched with saturated NaHCO₃ and the mixture is extracted with ether. The ether extracts are washed with brine, dried, and the solvent evaporated to give 42c which may be further purified by chromatography.

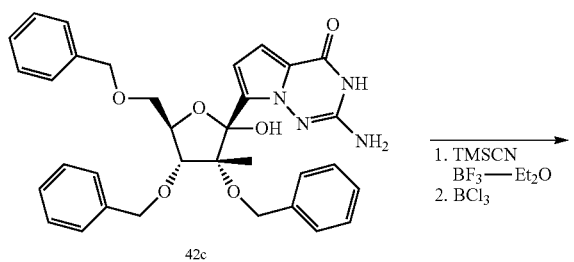

42c

1. TMSCN BF₃—Et₂O
2. BCl₃

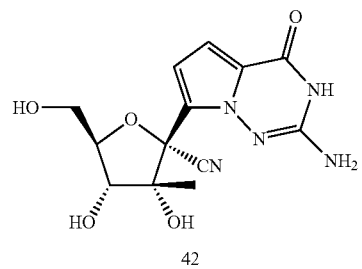

42

Compound 42 may be prepared from Compound 42a in the same manner as Compound 5 was prepared from Compound 2a.

Preparation of Compound 43

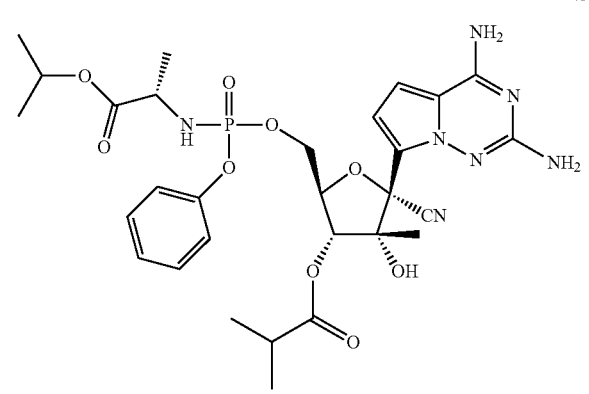

43

Compound 43 may be prepared in the same manner as Compound 8 starting with Compound 41 rather than Compound 6.

Preparation of Compound 44

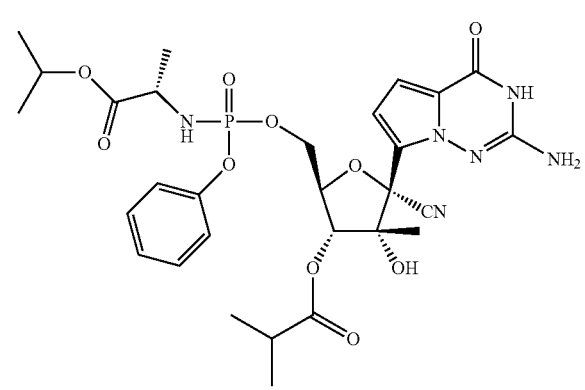

44

Compound 44 may be prepared in the same manner as Compound 8 starting with Compound 42 rather than Compound 6.

Using the same procedure for the preparation of Compound 8 from Compound 6, Compounds 50-59 may be prepared from Compounds 20-29, respectively.

-continued
Compound 50
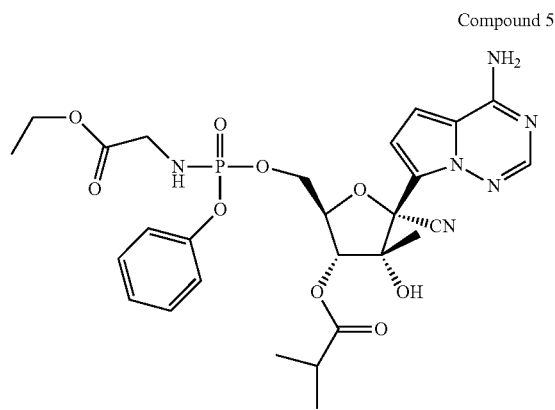
Compound 54
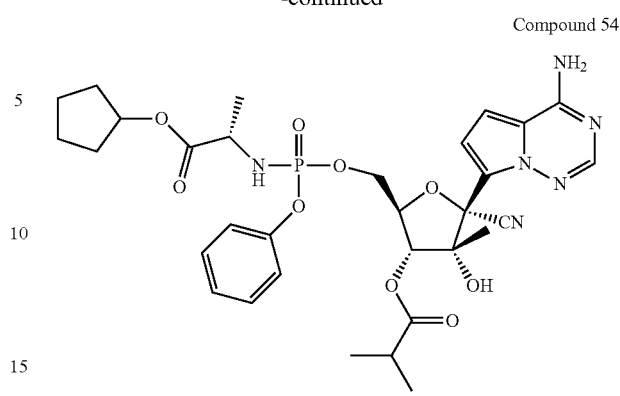
Compound 51
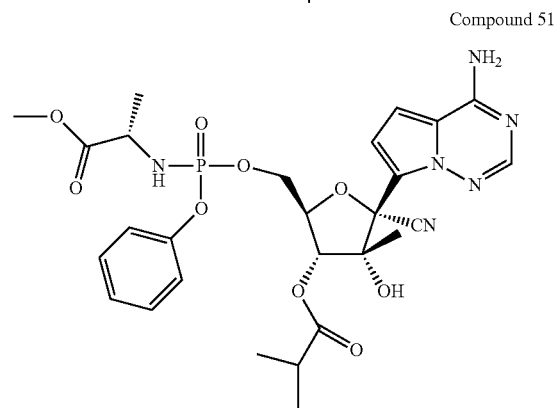
Compound 55
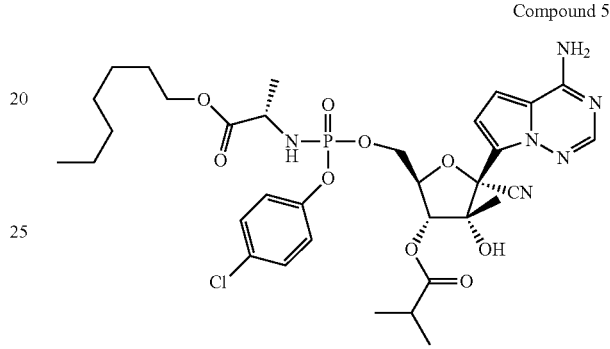
Compound 52
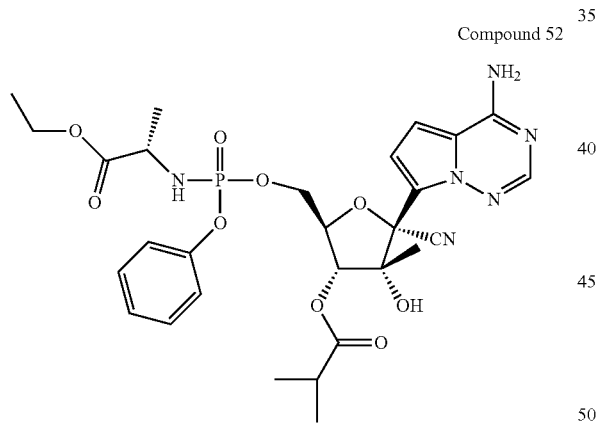
Compound 56
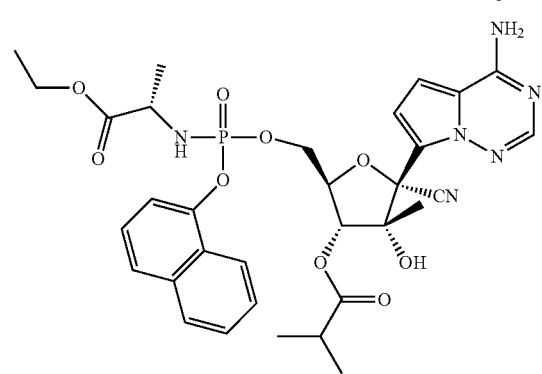
Compound 53
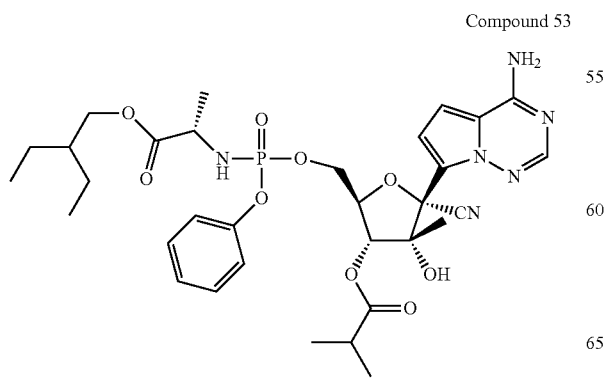
Compound 57
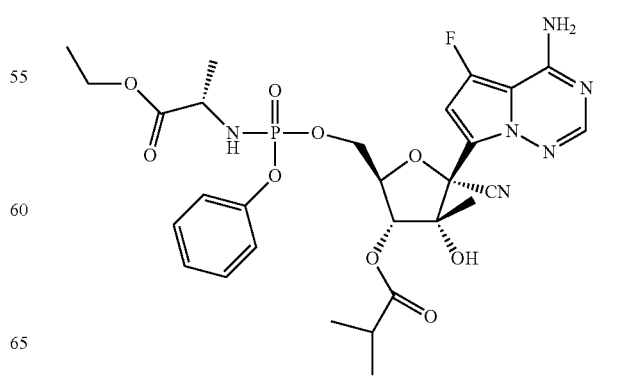

Compound 58

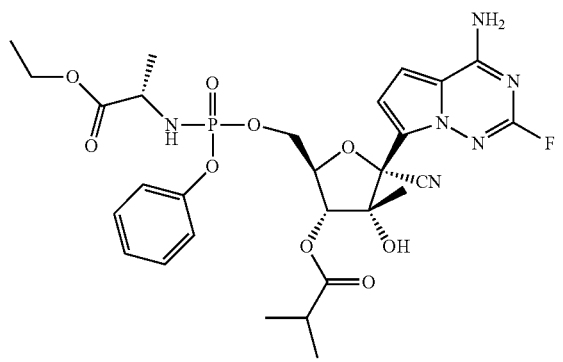

Compound 59

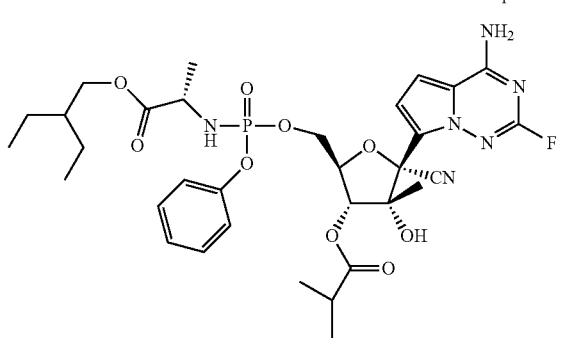

General Procedure for Preparation of Bisamidate Prodrugs

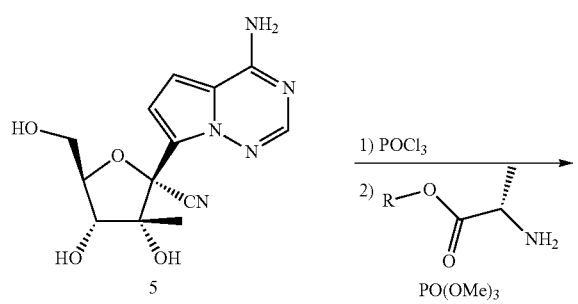

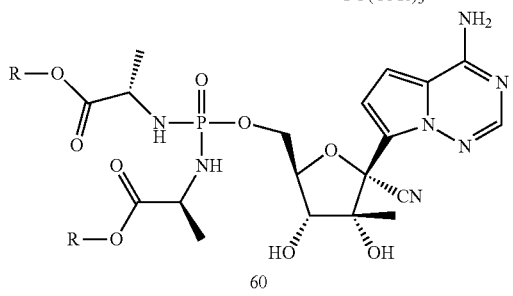

To a solution of compound 5 (0.5 mmol) in trimethoxyphosphate (1 mL) is added phosphorous oxychloride (1.0 mmol) at 0° C. and the mixture is stirred for 1 h. The mixture is then added to a freshly neutralized alanine ester (5-10 mmol) in THF (~5 mL) at 0° C., and is allowed to warm to room temperature for 1 h. The reaction is quenched with water. The mixture was extracted with ethyl acetate and the ethyl acetate extract was concentrated. The residue is purified by either silica gel chromatography or reverse-phase HPLC, to afford bisamidate 60.

Using the general procedure for the synthesis of the bisamidate prodrugs 60, Compounds 61-63 were prepared.

Compound 61

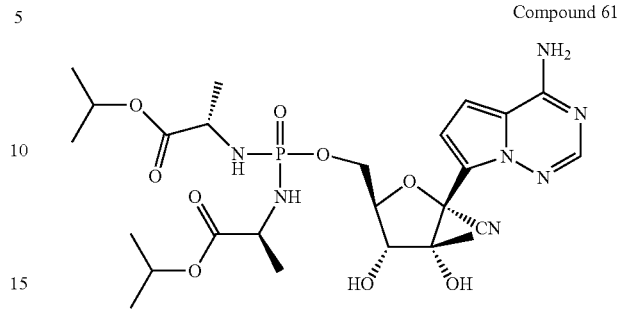

Compound 61: $^1$H NMR (400 MHz, CDCl$_3$): δ 8.03 (s, 1H), 6.84 (d, J=4.0 Hz, 1H), 6.72 (d, J=4.0 Hz, 1H), 6.1 (brs, 2H), 5.02 (m, 2H), 4.57 (q, 1H), 4.29 (dd, 2H), 3.95 (d, 1H), 3.92 (m, 2H), 3.48 (m, 2H), 1.49 (d, 6H), 1.25 (t, 12H), 0.95 (s, 3H). $^{31}$P NMR (162.1 MHz, CDCl$_3$): δ 12.59. MS=610.1 (M−H$^+$).

Compound 62

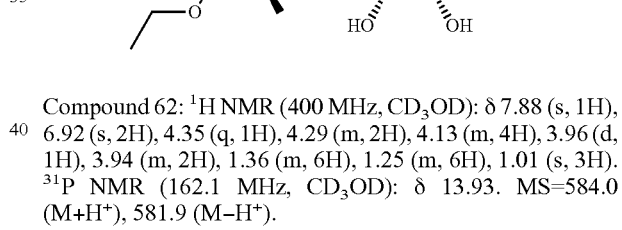

Compound 62: $^1$H NMR (400 MHz, CD$_3$OD): δ 7.88 (s, 1H), 6.92 (s, 2H), 4.35 (q, 1H), 4.29 (m, 2H), 4.13 (m, 4H), 3.96 (d, 1H), 3.94 (m, 2H), 1.36 (m, 6H), 1.25 (m, 6H), 1.01 (s, 3H). $^{31}$P NMR (162.1 MHz, CD$_3$OD): δ 13.93. MS=584.0 (M+H$^+$), 581.9 (M−H$^+$).

Compound 63

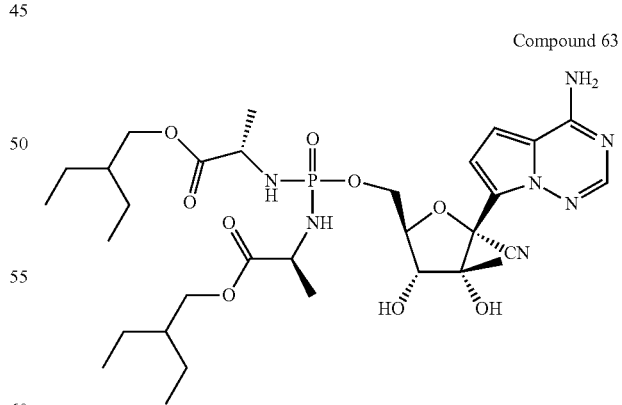

Compound 63: $^1$H NMR (300 MHz, CDCl$_3$): δ 8.02 (s, 1H), 6.83 (d, J=4.5 Hz, 1H), 6.72 (d, J=4.5 Hz, 1H), 6.2 (brs, 2H), 4.57 (q, 1H), 4.30 (dd, 2H), 3.9-4.2 (m, 7H), 3.59 (q, 2H), 1.52 (m, 2H), 1.2-1.5 (m, 14H), 0.95 (s, 3H), 0.89 (t, 12H). $^{31}$P NMR (121.4 MHz, CDCl$_3$): δ 12.62. MS=696.2 (M+H$^+$), 694.1 (M−H$^+$).

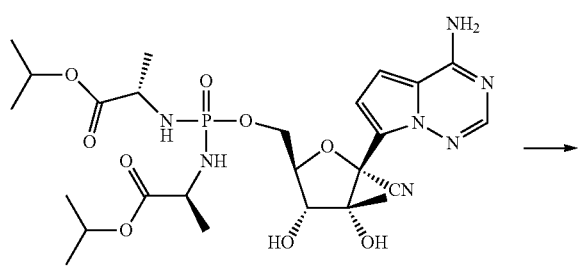

61

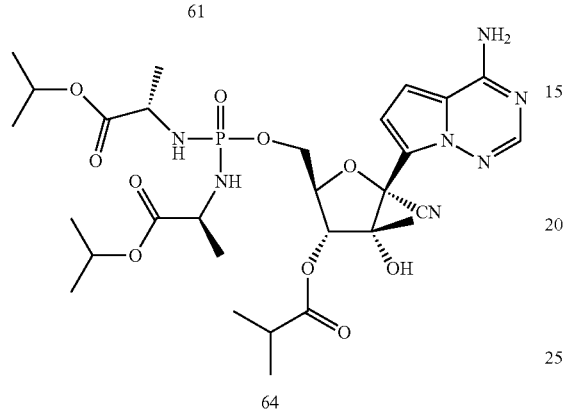

64

Compound 64 was made from Compound 61 following the procedure described for the preparation of Compound 8 from Compound 6. $^1$H NMR (400 MHz, CDCl$_3$): δ 8.00 (s, 1H), 6.87 (d, J=4.4 Hz, 1H), 6.73 (d, J=4.4 Hz, 1H), 5.98 (brs, 2H), 5.03 (m, 1H+2H), 4.66 (q, 1H), 4.33 (m, 2H), 4.29 (m, 1H), 3.92 (m, 2H), 3.44 (m, 2H), 2.74 (m, 1H), 1.39 (d, 6H), 1.2-1.3 (t, 18H), 1.04 (s, 3H). $^{31}$P NMR (162.1 MHz, CDCl$_3$): δ 12.41. MS=682.4 (M+H$^+$).

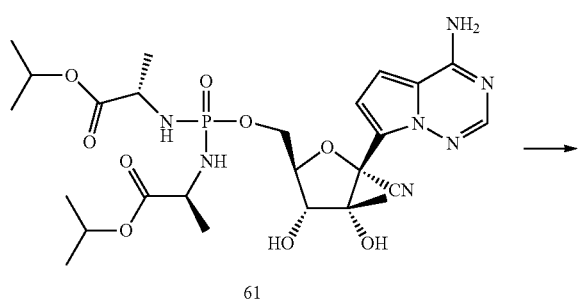

61

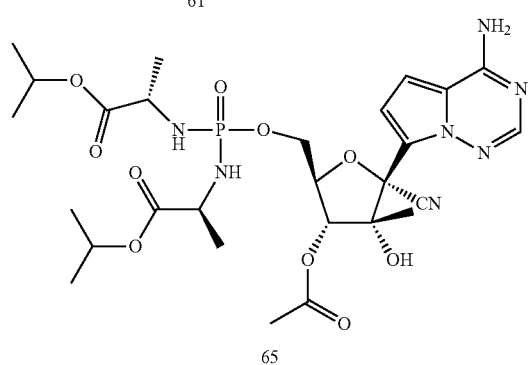

65

Compound 65 was prepared from Compound 61 following the procedure described for the preparation of Compound 8 from Compound 6 except acetic acid was substituted for isobutyric acid. $^1$H NMR (400 MHz, CDCl$_3$): δ 7.99 (s, 1H), 6.93 (s, 2H), 5.55 (brs, 2H), 5.03 (m, 1H+2H), 4.64 (q, 1H), 4.33 (m, 2H), 4.16 (m, 1H), 3.92 (m, 2H), 3.42 (m, 2H), 2.23 (s, 3H), 1.39 (2d, 6H), 1.2-1.3 (t, 12H), 1.05 (s, 3H). $^{31}$P NMR (162.1 MHz, CDCl$_3$): δ 12.5. MS=654.3 (M+H$^+$).

Using the same procedure for the preparation of Compound 8 from Compound 6, Compounds 66 and 67 may be prepared from Compounds 62 and 63, respectively.

Compound 66

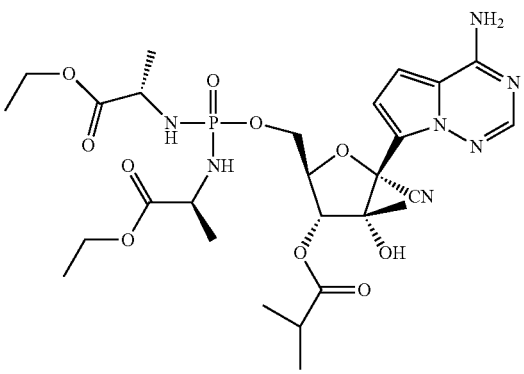

Compound 67

Antiviral Activity

Another aspect of the invention relates to methods of inhibiting viral infections, comprising the step of treating a sample or subject suspected of needing such inhibition with a composition of the invention.

Within the context of the invention samples suspected of containing a virus include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which induces a viral infection, frequently a pathogenic organism such as a tumor virus. Samples can be contained in any medium including water and organic solvent\water mixtures. Samples include living organisms such as humans, and man made materials such as cell cultures.

If desired, the anti-virus activity of a compound of the invention after application of the composition can be observed by any method including direct and indirect methods of detecting such activity. Quantitative, qualitative, and semiquantitative methods of determining such activity are all contemplated. Typically one of the screening methods described above are applied, however, any other method such as observation of the physiological properties of a living organism are also applicable.

The antiviral activity of a compound of the invention can be measured using standard screening protocols that are known. For example, the antiviral activity of a compound can be measured using the following general protocols.

HCV $IC_{50}$ Determination

Assay Protocol: NS5b polymerase assay (40 µL) was assembled by adding 28 µL polymerase mixture (final concentration: 50 mM Tris-HCl at pH 7.5, 10 mM KCL, 5 mM $MgCl_2$, 1 mM DTT, 10 mM EDTA, 4 ng/µL of RNA template, and 75 nM HCV Δ21 NS5b polymerase) to assay plates followed by 4 µL of compound dilution. The polymerase and compound were pre-incubated at 35° C. for 10 minute before the addition of 8 µL of nucleotide substrate mixture (33P-α-labeled competing nucleotide at $K_M$ and 0.5 mM of the remaining three nucleotides). The assay plates were covered and incubated at 35° C. for 90 min. Reactions were then filtered through 96-well DEAE-81 filter plates via vacuum. The filter plates were then washed under vacuum with multiple volumes of 0.125 M $NaHPO_4$, water, and ethanol to remove unincorporated label. Plates were then counted on TopCount to assess the level of product synthesis over background controls. The IC50 value is determined using Prism fitting program.

Preferably, compounds described herein inhibited NS5b polymerase with an $IC_{50}$'s below 1000 µM, more preferably below 100 µM, and most preferably below 10 µM. For example, compound 7 has an $IC_{50}$ below 1 µM.

HCV $EC_{50}$ Determination

Replicon cells were seeded in 96-well plates at a density of $8 \times 10^3$ cells per well in 100 µL of culture medium, excluding Geneticin. Compound was serially diluted in 100% DMSO and then added to the cells at a 1:200 dilution, achieving a final concentration of 0.5% DMSO and a total volume of 200 µL. Plates were incubated at 37° C. for 3 days, after which culture medium was removed and cells were lysed in lysis buffer provided by Promega's luciferase assay system. Following the manufacturer's instruction, 100 µL of luciferase substrate was added to the lysed cells and luciferase activity was measured in a TopCount luminometer. Preferably, compounds described herein have EC50's below 100 µM, more preferably below 10 µM, and most preferably below 1 µM.

Representative examples of the activity of the compounds Formula I-IV are shown in the Table below.

| Compound No. | $EC_{50}$, µM |
| --- | --- |
| 5 | >89 |
| 6 | 0.48 to 1.8 |
| 8 | 0.14 to 0.52 |
| 8A | 0.096 to 0.36 |
| 8B | 0.46 to 1.9 |
| 61 | 51 |
| 64 | 5.38 |
| 65 | 8.4 |

The specific activity observed may vary according to and depending on the particular replicon tested, the active compound selected or whether there are present pharmaceutical carriers, as well as the type of formulation and mode of administration employed, and such expected variations or differences in the results are contemplated in accordance with practice of the present invention.

The cytotoxicity of a compound of the invention can be determined using the following general protocol.

Cytotoxicity Cell Culture Assay (Determination of CC50):

The assay is based on the evaluation of cytotoxic effect of tested compounds using a metabolic substrate.

Assay Protocol for Determination of CC50:

1. Maintain MT-2 cells in RPMI-1640 medium supplemented with 5% fetal bovine serum and antibiotics.
2. Distribute the cells into a 96-well plate (20,000 cell in 100 µl media per well) and add various concentrations of the tested compound in triplicate (100 µl/well). Include untreated control.
3. Incubate the cells for 5 days at 37° C.
4. Prepare XTT solution (6 ml per assay plate) in dark at a concentration of 2 mg/ml in a phosphate-buffered saline pH 7.4. Heat the solution in a water-bath at 55° C. for 5 min. Add 50 µl of N-methylphenazonium methasulfate (5 µg/ml) per 6 ml of XTT solution.
5. Remove 100 µl media from each well on the assay plate and add 100 µl of the XTT substrate solution per well. Incubate at 37° C. for 45 to 60 min in a $CO_2$ incubator.
6. Add 20 µl of 2% Triton X-100 per well to stop the metabolic conversion of XTT.
7. Read the absorbance at 450 nm with subtracting off the background at 650 nm.
8. Plot the percentage absorbance relative to untreated control and estimate the CC50 value as drug concentration resulting in a 50% inhibition of the cell growth. Consider the absorbance being directly proportional to the cell growth.

Determination of Nucleoside Mono-, Di- and Tri-Phosphate Concentrations in Liver and Plasma of Male Golden Syrian Hamsters Experimental Design The in-life activities were conducted using the experimental design shown below.

Experimental Design

| Group | Dosage (mg-eq/kg/day) | Concentration (mg/mL) | Volume (mL/kg) | Mean Weight (kg) | N |
| --- | --- | --- | --- | --- | --- |
| Intravenous (iv) | 1 | 0.5 | 2 | 0.1 | 12 |
| Oral (po) | 5 | 2.5 | 2 | 0.1 | 12 |

Formulation

The compounds were formulated in 50/50 (PEG400/Water pH 4 by HCl) for intravenous dose. The following solution formulations were used for oral dosage.

| Compound | Solution Formulation |
| --- | --- |
| 6 | 5/30/65 EtOH/$PEG_{400}$/water (50 mM citrate buffer pH 4) |
| 8 | 5/55/40 EtOH/$PEG_{400}$/water (50 mM citrate buffer pH 4) |
| 8B | 5/55/40 EtOH/$PEG_{400}$/water (50 mM citrate buffer pH 2.2) |
| 8A | 5/55/40 EtOH/$PEG_{400}$/water (50 mM citrate buffer pH 2.2) |

Sample Collection

| Samples | Time Points (hrs) |
|---|---|
| Plasma (i.v.) | Predose, 0.083, 0.33, 1, 4, 8, and 24 |
| Plasma (p.o.) | Predose, 0.5, 1, 2, 4, 8, and 24 |
| Liver | 1, 4, 8, and 24 |

The animals were fasted overnight prior to dosing. Blood samples were collected via jugular stick at all times post-dose into Vacutainer™ tubes containing heparin (BD Biosciences). The blood samples were centrifuged at 4° C. to separate plasma. Plasma samples were frozen and shipped on dry ice. Once received, samples were stored in −80° C. freezers.

At each terminal collection, animals were anesthetized under isoflurane and livers were harvested. Collected livers were wrapped in aluminum foil and flash-frozen in liquid nitrogen immediately following removal. Livers were shipped on dry ice and stored at −80° C. until processing.

Sample Processing

Plasma was prepared by protein precipitation by adding acetonitrile to a final concentration of 70% in the presence of internal standard (300 nM 5-iodotubericidin). Samples were dried down completely for approximately 20 minutes and reconstituted with 0.2% formic acid in water.

Livers were prepared by sectioning into smaller pieces with a razor blade and collecting into pre-weighed 15 mL conical tubes kept on dry ice. Four volumes of ice-cold extraction buffer (0.1% KOH and 67 mM EDTA in 70% MeOH, containing 0.5 µM Cl-ATP) were added and samples were promptly homogenized using an Omni-Tip TH™ with disposable, hard tissue homogenizer probes (Omni International). Aliquots of homogenate were then centrifuged (20,000×g @ 4° C. for 10 minutes), and aliquots of supernatant were transferred to clean tubes, evaporated to dryness in a heated, centrifuging evaporator and reconstituted with an equal volume of 1 mM ammonium phosphate, pH-7 for LC-MS/MS analysis. For adenosine, AMP, ADP and ATP analysis, supernatant was diluted an additional 1,000-fold in ammonium phosphate buffer.

Plasma Analysis
HPLC Conditions
Column:
Phenomenex Synergi Max-RP; 150×2×4µ,
Mobile Phases:
Mobile phase A containing 0.2% formic acid in water and mobile phase B containing 0.2% formic acid in 95% acetonitrile
HPLC Pump and Autosampler:
Shimadzu LC-10AD ternary pump system was used for elution and separation and an HTC Pal autosampler from LEAP Technologies.
HPLC Elution Program:

| Time (min) | Flow Rate (ml/min) | Mobile Phase A (%) | Mobile Phase B (%) |
|---|---|---|---|
| 0.00 | 0.25 | 96 | 4 |
| 0.80 | 0.25 | 96 | 4 |
| 4.00 | 0.25 | 0 | 100 |
| 4.70 | 0.25 | 0 | 100 |
| 4.80 | 0.25 | 96 | 4 |

Mass Spectrometry
Mass Spectrometer:
API 4000 triple quadrupole mass spectrometer (Applied Biosystems/MDS Sciex)
Operation Mode:
multiple reaction monitoring (MRM)
Mass Spectrometry Parameters

| Ion source | Probe height (mm) | Spray voltage (V) | temperature (° C.) | Curtain gas (psi) | Collision gas (psi) |
|---|---|---|---|---|---|
| ESI+ | 4 | 5500 | 500 | 10 | 4 |

MRM Channels

| Analyte | Description | Parent Mass (m/z) | Product Mass (m/z) | Declustering Potential (V) | Collision Energy (eV) |
|---|---|---|---|---|---|
| Compound 5 | nucleoside | 306.3 | 216.2 | 45 | 20 |
| Compound 6 | metabolite | 575.3 | 288.2 | 116 | 31 |
| Compound 8A | prodrug | 645.3 | 358.2 | 121 | 31 |
| 5-iodotubericidin | internal standard | 393.1 | 206.1 | 77 | 30 |

Assay Performance
Calibration Curve Parameters

| Analyte | Sample matrix | Study | RT (min) | LOQ (nM) | Range (nM) | Weight Index | $R^2$ |
|---|---|---|---|---|---|---|---|
| Comp. 5 | Plasma | AD-119-2053 | 3.2 | 15.4 | 15.4-5,000 | 1/x | 1.0 |
| Comp. 6 | Plasma | AD-119-2053 | 3.7 | 15.4 | 15.4-5,000 | 1/x | 1.0 |
| Comp. 8A | Plasma | AD-119-2053 | 4.4 | 15.4 | 15.4-5,000 | 1/x | 0.99 |

Liver Analysis
HPLC Conditions
Column:
Phenomenex Luna C18 HST 2.5 µm 2.0×50 mm column (part No. 00B-4446-B0)
Mobile Phases:
Mobile phase A containing 3 mM ammonium formate (pH 5) with 10 mM dimethylhexylamine (DMH) in water and a mobile phase B containing 3 mM ammonium formate (pH 5) with 10 mM DMH in 50% acetonitrile.
HPLC Pump and Autosampler:
Shimadzu LC-10AD ternary pump system was used for elution and separation and an HTC Pal autosampler from LEAP Technologies.
HPLC Elution Program:

| Time (min) | Flow Rate (ml/min) | Mobile Phase A (%) | Mobile Phase B (%) |
|---|---|---|---|
| 0 | 0.14 | 80 | 20 |
| 0.30 | 0.14 | 80 | 20 |
| 4.00 | 0.14 | 40 | 60 |
| 6.00 | 0.14 | 0 | 100 |
| 7.50 | 0.14 | 0 | 100 |
| 7.60 | 0.14 | 80 | 20 |

Mass Spectrometry

Mass Spectrometer:

API 4000 triple quadrupole mass spectrometer (Applied Biosystems/MDS Sciex)

Operation Mode:

multiple reaction monitoring (MRM)

Mass Spectrometry Parameters

| Ion source | Probe height (mm) | Spray voltage (V) | temperature (° C.) | Curtain gas (psi) | Collision gas (psi) |
|---|---|---|---|---|---|
| ESI+ | 4 | 5500 | 500 | 10 | 4 |

MRM Channels

| Analyte | Description | Parent Mass (m/z) | Product Mass (m/z) | Declustering Potential (V) | Collision Energy (eV) |
|---|---|---|---|---|---|
| Compound 5 | Parent | 306.2 | 216.2 | 89 | 18 |
| Compound 17 | Parent-monophosphate | 386.2 | 216.2 | 110 | 22 |
| Compound 5-DP | Parent-diphosphate | 466.2 | 216.2 | 131 | 27 |
| Compound 7 | Parent-triphosphate | 466.2 | 216.2 | 152 | 31 |
| Cl-ATP | Internal standard | 542.2 | 170.2 | 125 | 29 |
| Adenosine | Natural nucleoside | 268.2 | 136.2 | 61 | 25 |
| AMP | Natural nucleotide | 348.2 | 136.2 | 70 | 30 |
| ADP | Natural nucleotide | 428.2 | 136.2 | 90 | 30 |
| ATP | Natural nucleotide | 508.2 | 136.2 | 140 | 45 |
| $^{13}C$-$^{15}N$-Adenosine | Stable isotope | 283.2 | 146.1 | 61 | 24 |
| $^{13}C$-$^{15}N$-AMP | Stable isotope | 363.2 | 146.1 | 70 | 30 |
| $^{13}C$-$^{15}N$-ADP | Stable isotope | 443.2 | 146.1 | 90 | 30 |
| $^{13}C$-$^{15}N$-ATP | Stable isotope | 523.2 | 146.1 | 140 | 40 |

TABLE 12

Mean Compound 7 Liver Concentrations Following Oral Administration of 5 mg-eq/kg of Compound 6, Compound 8, Compound 8B, or Compound 8A to Male Golden Syrian Hamsters

| | Liver Concentration Compound 7 (µM) ± SD | | | |
|---|---|---|---|---|
| Time (hr) | Compound 6 Mean | Compound 8 Mean | Compound 8B Mean | Compound 8A Mean |
| 1 | 0.179 ± 0.023 | 2.99 ± 0.43 | 3.29 ± 0.733 | 7.9 ± 2.0 |
| 4 | 0.530 ± 0.082 | 3.69 ± 1.03 | 3.14 ± 0.294 | 9.0 ± 1.2 |
| 8 | 0.241 ± 0.026 | 0.82 ± 0.27 | 1.14 ± 0.579 | 7.32 ± 0.61 |
| 24 | 0.058 ± 0.060 | 0.309 ± 0.074 | 0.896 ± 0.095 | 1.82 ± 0.46 |

Assay Performance

Calibration Curve Parameters

| Analyte | Sample matrix | Study | RT (min) | LOQ (µM) | Range (µM) | Weighting Index | $R^2$ |
|---|---|---|---|---|---|---|---|
| Compound 5 | Liver | AD-119-2053 | 2.6 | 0.648 | 0.648-17.5 | 1/x | 0.99 |
| Compound 17 | Liver | AD-119-2053 | 3.9 | 0.072 | 0.072-17.5 | 1/x | 1.0 |
| Compound 5-DP | Liver | AD-119-2053 | 4.7 | 0.072 | 0.072-17.5 | 1/x | 1.0 |
| Compound 7 | Liver | AD-119-2053 | 5.2 | 0.072 | 0.072-17.5 | 1/x | 1.0 |
| Adenosine* | Liver | AD-119-2053 | 1.9 | 74.1 | 74.1-2,000 | 1/x | 0.99 |
| AMP* | Liver | AD-119-2053 | 3.8 | 24.7 | 24.7-2,000 | 1/x | 1.0 |
| ADP* | Liver | AD-119-2053 | 4.5 | 24.7 | 24.7-2,000 | 1/x | 1.0 |
| ATP* | Liver | AD-119-2053 | 4.8 | 24.7 | 24.7-2,000 | 1/x | 1.0 |

*Based on calibration curve for respective stable isotopes ($^{13}C$—$^{15}N$)

Using the data in Table 12, the area under the curve for exposure of the Hamster livers to the Compound 7 concentrations after oral administration of 5 mg-eq/kg of Compound 6, Compound 8, Compound 8B, and Compound 8A, respectively, is shown in Table 13.

TABLE 13

Area Under The Curve For Mean Compound 7 Liver Concentrations Following Oral Administration of 5 mg-eq/kg of Compound 6, Compound 8, Compound 8B, or Compound 8A to Male Golden Syrian Hamsters

| PO @ 5 mg-eqv/kg | AUC 0-t (uM * hr) |
|---|---|
| Compound 6 | 5.1 |
| Compound 8 | 29.6 |
| Compound 8B | 46.1 |
| Compound 8A | 135 |

These data demonstrate that acylation of the 3'-hydroxyl group of a 5'-prodrug of a 1'-cyano-pyrrolo[1,2-f][1,2,4]triazine nucleoside such as Compound 6 leads to an unexpected about six to 26 fold greater exposure of the liver to the triphosphate of the pyrrolo[1,2-f][1,2,4]triazine nucleoside (Compound 7) after oral administration of the respective prodrugs. Oral administration of these 3'-O-acyl prodrugs have the advantage of producing higher concentrations of triphosphates of the nucleosides in the HCV infected liver cells of a mammal/human infected with HCV than oral administration of the non-3'-O-acylated prodrugs. These higher concentrations of triphosphates will more effectively treat the HCV infection by selectively inhibiting the HCV RdRp polyermerase.

All publications, patents, and patent documents cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:
1. A compound of Formula I:

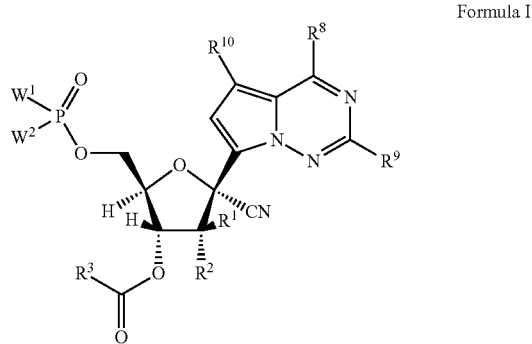

Formula I or a pharmaceutically acceptable salt or ester, thereof; wherein:
$R^1$ is H, $(C_1-C_8)$alkyl, $(C_2-C_8)$alkenyl, or $(C_2-C_8)$alkynyl;
$R^2$ is OH or $—OC(O)R^3$;
each $R^3$ is independently H, $OR^4$, $NH(R^4)$, $N(R^4)_2$, $SR^4$, $(C_1-C_8)$alkyl, $(C_2-C_8)$alkenyl, $(C_2-C_8)$alkynyl, $(C_3-C_8)$ carbocyclyl, $(C_4-C_8)$ carbocyclylalkyl, aryl$(C_1-C_8)$alkyl, heterocyclyl$(C_1-C_8)$alkyl, aryl, heterocyclyl or heteroaryl;
each $R^a$, $R^4$ or $R^6$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;
one of $W^1$ or $W^2$ is

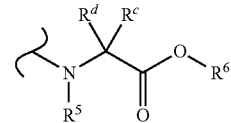

and the other of $W^1$ or $W^2$ is $OR^4$ or

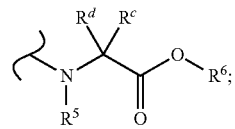

each $R^c$, $R^d$ or $R^5$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl;
each $R^8$ is halogen, $NR^{11}R^{12}$, $N(R^{11})OR^{11}$, $NR^{11}NR^{11}R^{12}$, $N_3$, NO, $NO_2$, CHO, CN, $—CH(=NR^{11})$, $—CH=NNHR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$, $(C_1-C_8)$alkyl, $(C_2-C_8)$alkenyl, $(C_2-C_8)$alkynyl, $(C_4-C_8)$carbocyclylalkyl, $(C_6-C_{20})$aryl, $(C_2-C_{20})$heterocyclyl, heteroaryl, $—C(=O)(C_1-C_8)$alkyl, $—S(O)_n(C_1-C_8)$alkyl, aryl$(C_1-C_8)$alkyl, $OR^{11}$ or $SR^{11}$;
each n is independently 0, 1, or 2;
each $R^9$ or $R^{10}$ is independently H, halogen, $NR^{11}R^{12}$, $N(R^{11})OR^{11}$, $NR^{11}NR^{11}R^{12}$, $N_3$, NO, $NO_2$, CHO, CN, $—CH(=NR^{11})$, $—CH=NHNR^{11}$, $—CH=N(OR^{11})$, $—CH(OR^{11})_2$, $—C(=O)NR^{11}R^{12}$, $—C(=S)NR^{11}R^{12}$, $—C(=O)OR^{11}$, $R^{11}$, $OR^{11}$ or $SR^{11}$;
each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl, $—C(=O)(C_1-C_8)$alkyl, $—S(O)_n(C_1-C_8)$alkyl or $R^{11}$ and $R^{12}$ taken together with a nitrogen to which they are both attached form a 3 to 7 membered heterocyclic ring wherein any one carbon atom of said heterocyclic ring can optionally be replaced with $—O—$, $—S(O)_n—$ or $—NR^a—$; and
wherein each $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl, heteroaryl of $R^c$, $R^d$, $R^1$, $R^2$, $R^3$, $R^4$, $R^5$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

2. The compound of claim 1 represented by Formula II

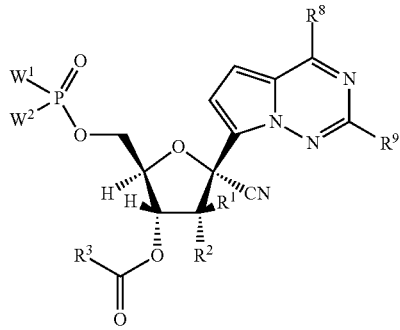

Formula II or a pharmaceutically acceptable salt or ester, thereof, wherein each $R^5$ is H.

3. The compound of claim 1 or 2 wherein $R^1$ is $(C_1\text{-}C_8)$ alkyl.

4. The compound of any one of claims 1-3 wherein $R^2$ is OH.

5. The compound of claim 1 represented by Formula III:

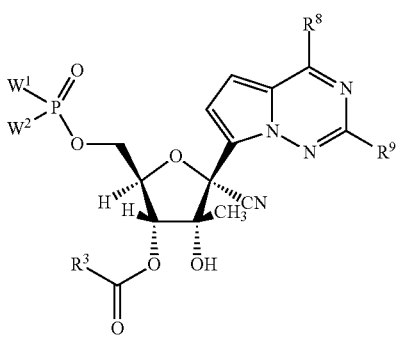

Formula III or a pharmaceutically acceptable salt or ester, thereof; wherein:

$R^3$ is $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$ carbocyclylalkyl, aryl$(C_1\text{-}C_8)$ alkyl, heterocyclyl$(C_1\text{-}C_8)$alkyl, aryl, heterocyclyl or heteroaryl;

each $R^a$ or $R^6$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$ alkyl, $(C_6\text{-}C_{20})$aryl, $(C_2\text{-}C_{20})$heterocyclyl or heteroaryl;

one of $W^1$ or $W^2$ is

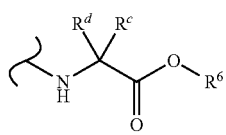

and the other of $W^1$ or $W^2$ is $OR^4$ or

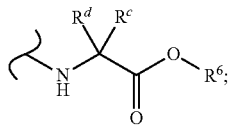

each $R^c$ or $R^d$ is independently H, $(C_1\text{-}C_8)$alkyl, $(C_2\text{-}C_8)$ alkenyl, $(C_2\text{-}C_8)$alkynyl, $(C_3\text{-}C_8)$carbocyclyl, $(C_4\text{-}C_8)$ carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

each $R^4$ is $(C_6\text{-}C_{20})$aryl or heteroaryl;

each $R^8$ is halogen, $NR^{11}R^{12}$, $N(R^{11})OR^{11}$, $NR^{11}NR^{11}R^{12}$, $N_3$, $-S(O)_n(C_1\text{-}C_8)$alkyl, $OR^{11}$ or $SR^{11}$;

each n is independently 0, 1, or 2;

each $R^9$ is independently H, halogen, $NR^{11}R^{12}$, $N(R^{11})OR^{11}$, $NR^{11}NR^{11}R^{12}$, $N_3$, $OR^{11}$ or $SR^{11}$;

each $R^{11}$ or $R^{12}$ is independently H, $(C_1\text{-}C_8)$alkyl, $(C_2\text{-}C_8)$ alkenyl, $(C_2\text{-}C_8)$alkynyl, $(C_3\text{-}C_8)$carbocyclyl, $(C_4\text{-}C_8)$ carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl, heteroaryl, $-C(=O)(C_1\text{-}C_8)$alkyl, $-S(O)_n(C_1\text{-}C_8)$ alkyl or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; and wherein each $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl $(C_1\text{-}C_8)$alkyl, heterocyclyl$(C_1\text{-}C_8)$alkyl, $(C_6\text{-}C_{20})$aryl, $(C_2\text{-}C_{20})$heterocyclyl, heteroaryl of $R^c$, $R^d$, $R^3$, $R^4$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

6. The compound of claim 1 represented by Formula IV:

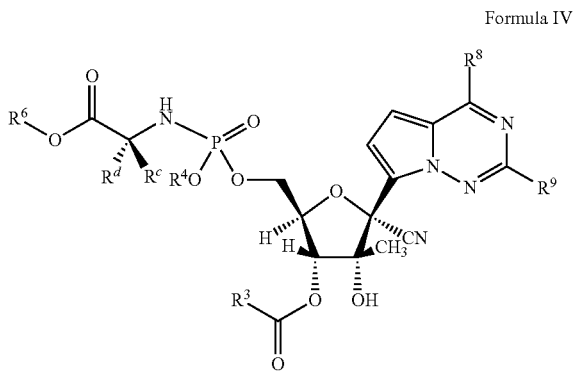

Formula IV or a pharmaceutically acceptable salt or ester, thereof; wherein:

$R^3$ is $(C_1\text{-}C_8)$alkyl, $(C_2\text{-}C_8)$alkenyl, $(C_2\text{-}C_8)$alkynyl, $(C_3\text{-}C_8)$carbocyclyl or $(C_4\text{-}C_8)$ carbocyclylalkyl;

each $R^a$ is independently $(C_1\text{-}C_8)$alkyl, $(C_2\text{-}C_8)$alkenyl, $(C_2\text{-}C_8)$alkynyl, $(C_3\text{-}C_8)$carbocyclyl, $(C_4\text{-}C_8)$carbocyclylalkyl, aryl$(C_1\text{-}C_8)$alkyl, heterocyclyl$(C_1\text{-}C_8)$alkyl, $(C_6\text{-}C_{20})$aryl, $(C_2\text{-}C_{20})$heterocyclyl or heteroaryl;

each $R^c$ or $R^d$ is independently H or methyl;

$R^4$ is $(C_6$-$C_{20})$aryl;

$R^6$ is $(C_1$-$C_8)$alkyl, $(C_2$-$C_8)$alkenyl, $(C_2$-$C_8)$alkynyl, $(C_3$-$C_8)$carbocyclyl or $(C_4$-$C_8)$carbocyclylalkyl;

each $R^8$ is halogen, $NR^{11}R^{12}$, $N(R^{11})OR^{11}$, $NR^{11}NR^{11}R^{12}$, $N_3$, —S(O)$_n$($C_1$-$C_8$)alkyl, $OR^{11}$ or $SR^{11}$;

each n is independently 0, 1, or 2;

each $R^9$ is independently H, halogen, $NR^{11}R^{12}$, $N(R^{11})OR^{11}$, $NR^{11}NR^{11}R^{12}$, $N_3$, $OR^{11}$ or $SR^{11}$;

each $R^{11}$ or $R^{12}$ is independently H, $(C_1$-$C_8)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl($C_1$-$C_8$)alkyl, heterocyclyl($C_1$-$C_8$)alkyl, $(C_6$-$C_{20})$aryl, $(C_2$-$C_{20})$heterocyclyl, heteroaryl, —C(=O)($C_1$-$C_8$)alkyl, —S(O)$_n$($C_1$-$C_8$)alkyl or $R^{11}$ and $R^{12}$ taken together with a nitrogen to which they are both attached form a 3 to 7 membered heterocyclic ring wherein any one carbon atom of said heterocyclic ring can optionally be replaced with —O—, —S(O)$_n$— or —NR$^a$—; and wherein each $(C_1$-$C_8)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, aryl($C_1$-$C_8$)alkyl, heterocyclyl($C_1$-$C_8$)alkyl, $(C_6$-$C_{20})$aryl, $(C_2$-$C_{20})$heterocyclyl, heteroaryl of $R^3$, $R^4$, $R^6$, $R^8$, $R^{11}$ or $R^{12}$ is, independently, optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $C(O)R^a$, $OC(O)R^a$, $S(O)_nR^a$, $S(O)_2N(R^a)_2$, $S(O)_2NH(R^a)$, $S(O)_2NH_2$, $OR^a$ or $R^a$.

7. The compound of claim 1 wherein the chirality of phosphorous is R.

8. The compound of claim 1 wherein the chirality of phosphorus is S.

9. The compound of any one of claim 1, 5, or 6 wherein $R^3$ is $(C_1$-$C_8)$alkyl.

10. The compound of any one of claim 1, 5, or 6 wherein one of $R^c$ or $R^d$ is H and the other of $R^c$ or $R^d$ is $(C_1$-$C_8)$alkyl.

11. The compound of any one of claim 1, 5, or 6 wherein $R^6$ is $(C_1$-$C_8)$alkyl.

12. The compound of claim 1 wherein $R^8$ is $NR^{11}R^{12}$ or $OR^{11}$.

13. The compound of any one of claim 1, 5, or 6 wherein $R^9$ is H or $NR^{11}R^{12}$.

14. The compound of claim 1 wherein each $R^{11}$ and $R^{12}$ is H.

15. The compound of any one of claim 1, 5, or 6 wherein $R^8$ is $NH_2$ and $R^9$ is H.

16. The compound of claim 1 wherein $R^4$ is $(C_6$-$C_{20})$aryl.

17. The compound of claim 1 that is

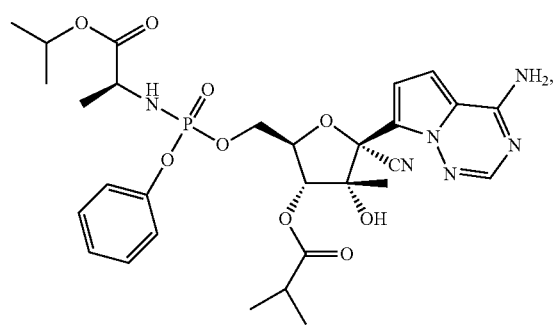

-continued

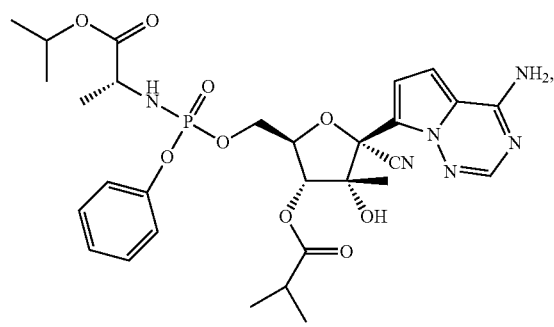

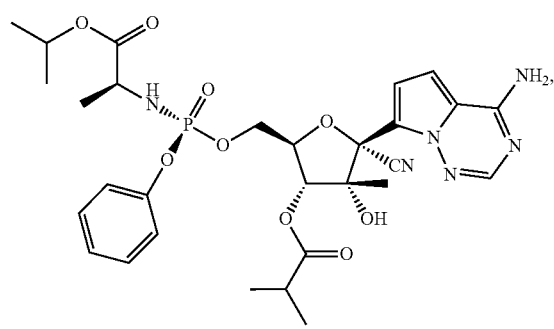

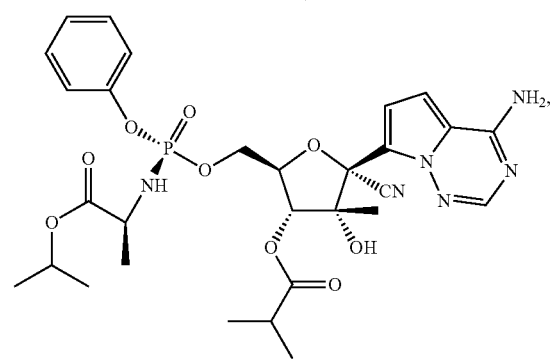

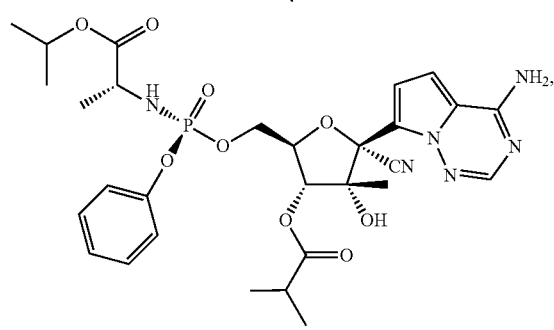

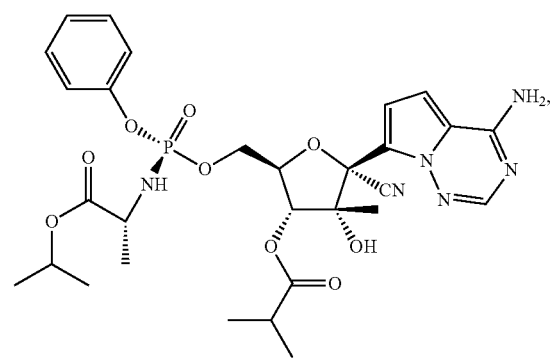

103
-continued
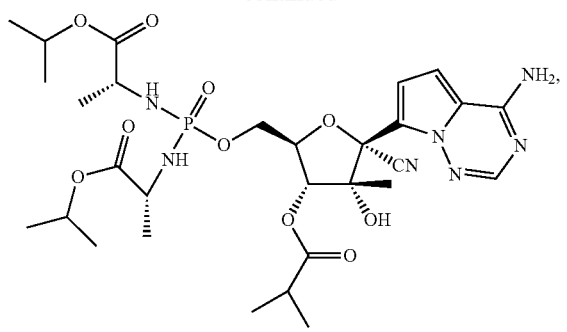
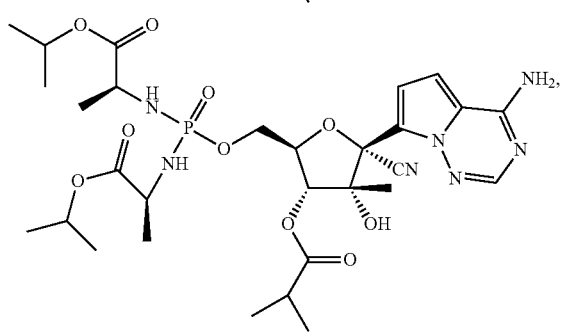
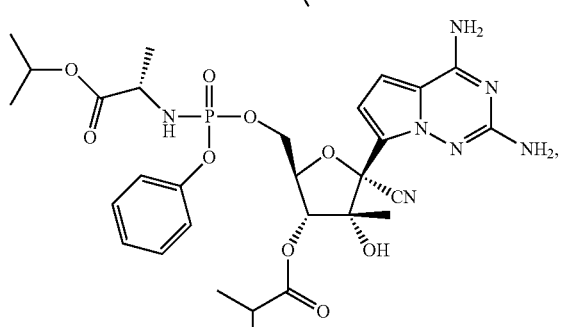
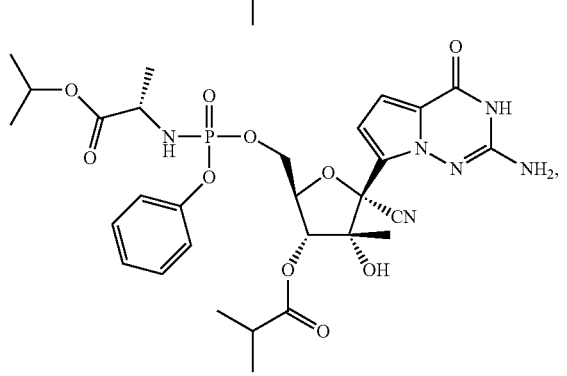
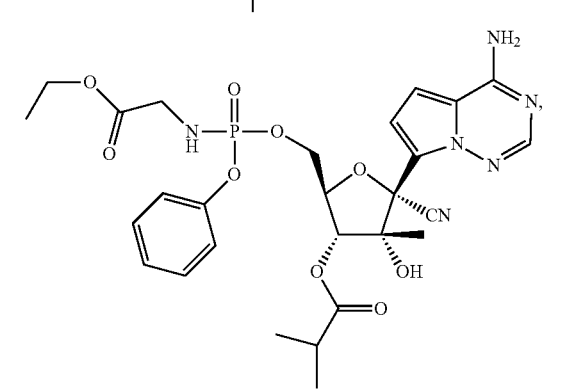
104
-continued
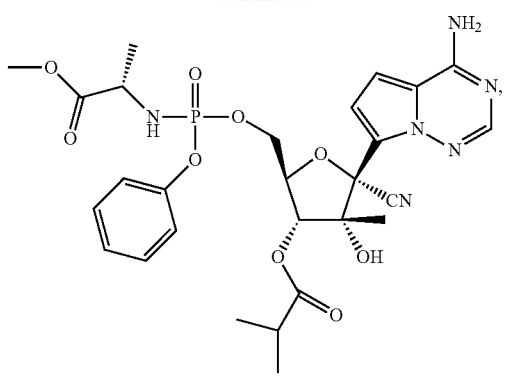
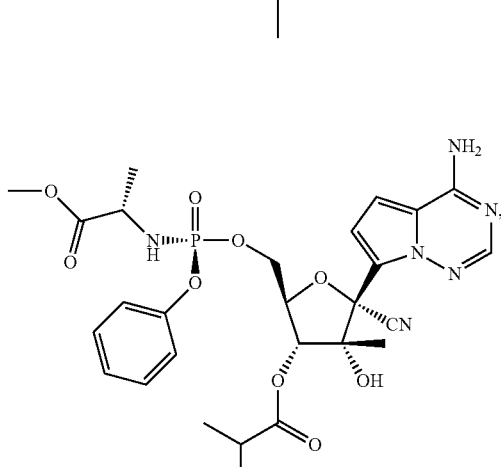
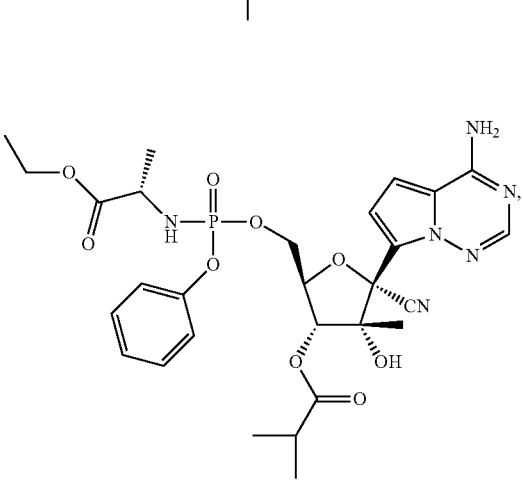
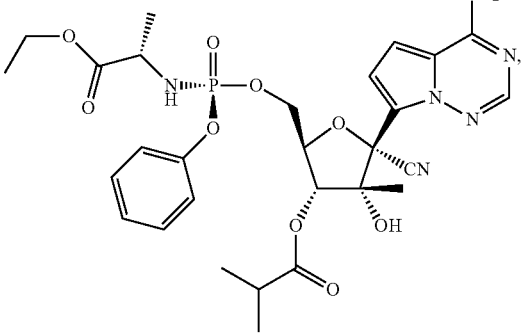

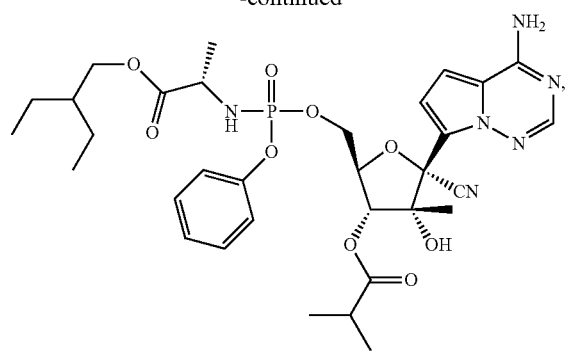
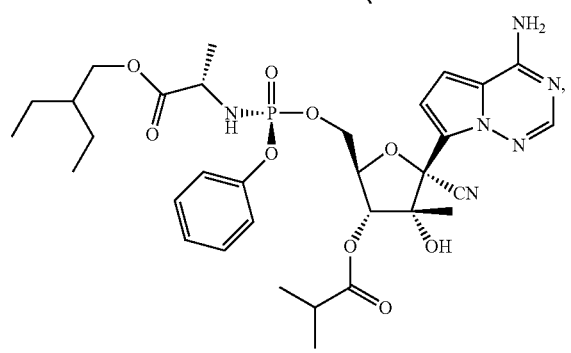
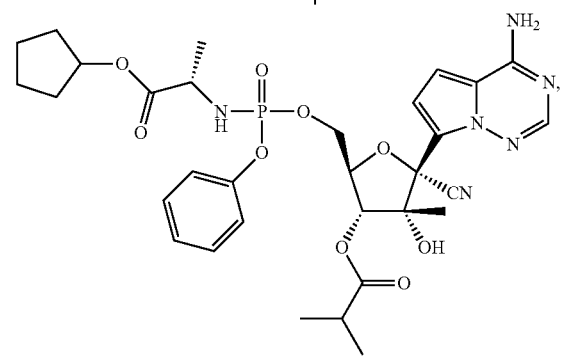
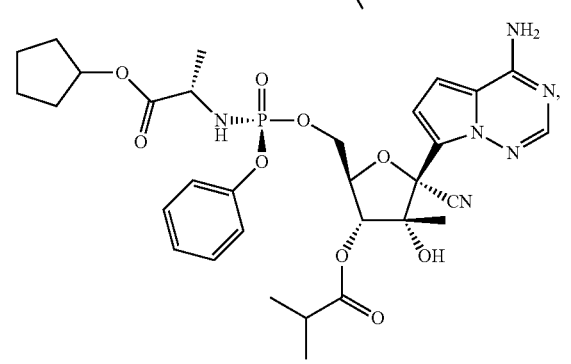
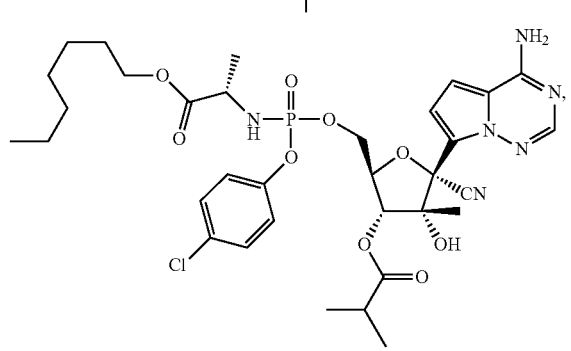
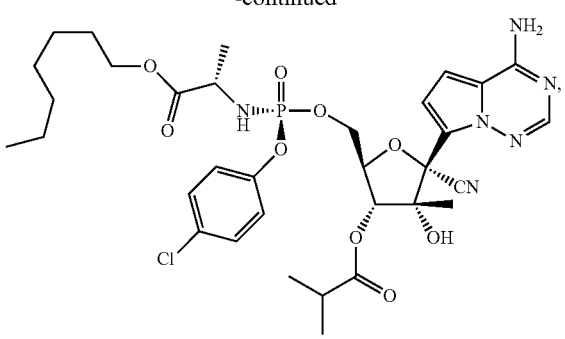
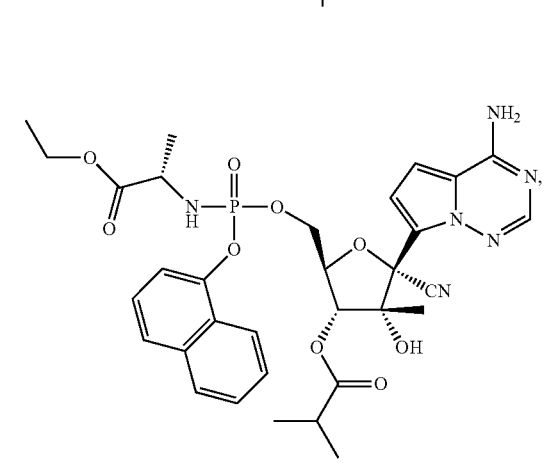
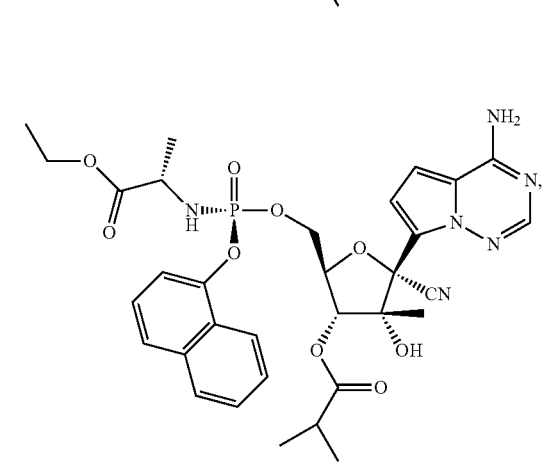
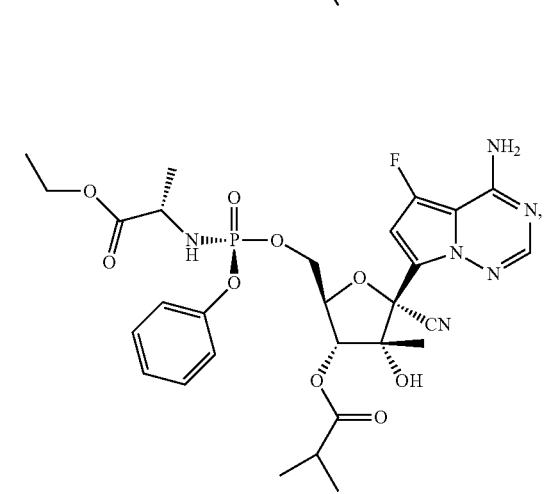

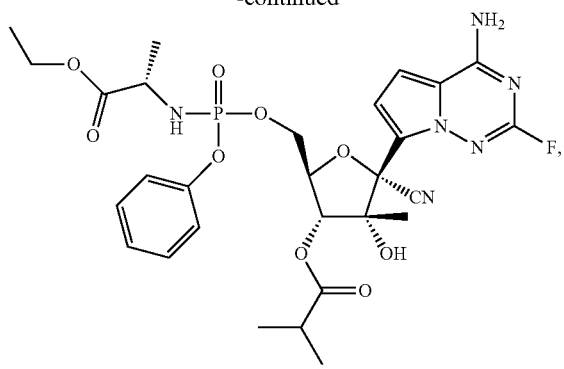

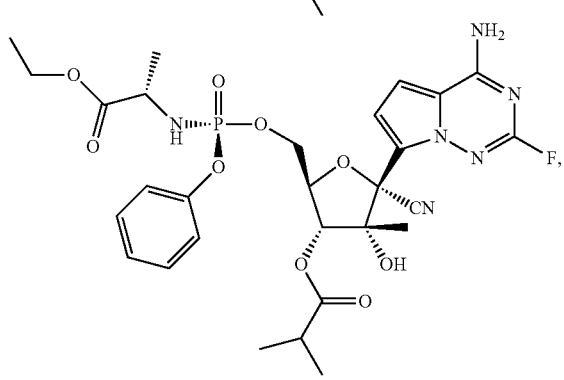

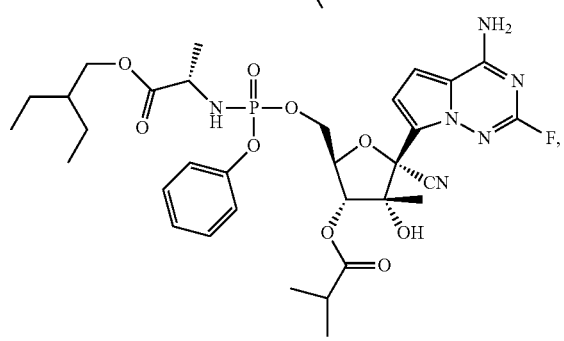

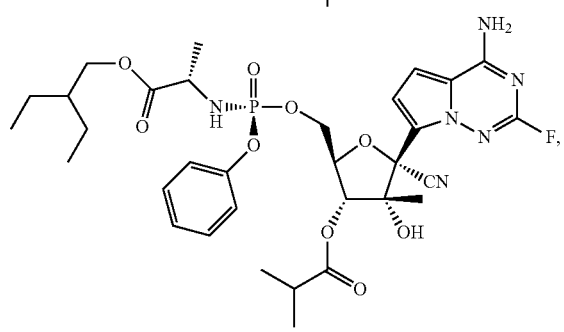

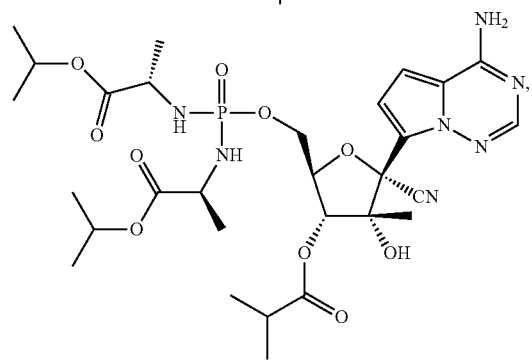

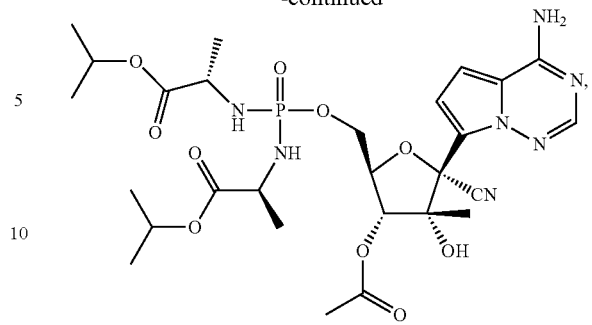

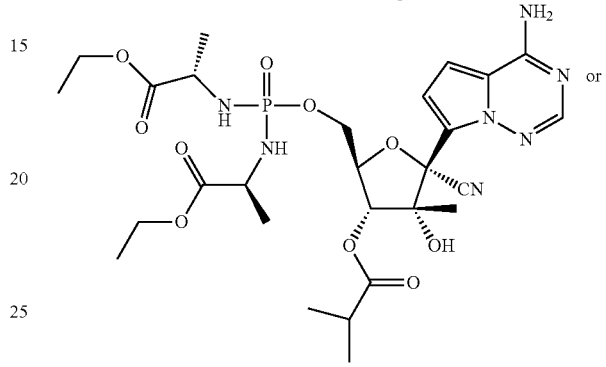

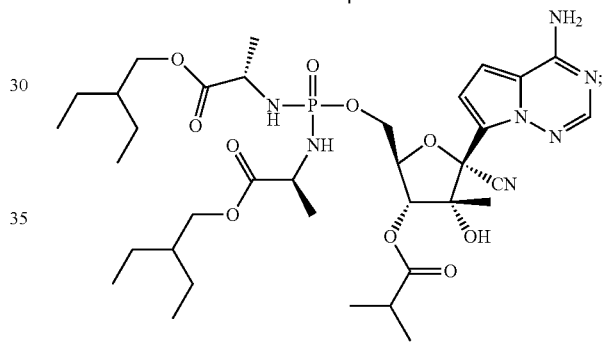

or a pharmaceutically acceptable salt or ester thereof.

18. A pharmaceutical composition comprising a therapeutically effective amount of a compound or pharmaceutically acceptable salt or ester thereof of claim 1 or 17 and a pharmaceutically acceptable carrier.

19. The pharmaceutical composition of claim 18 further comprising at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

20. A method of inhibiting HCV polymerase comprising administering to a mammal in need thereof a therapeutically effective amount of a compound or pharmaceutically acceptable salt or ester thereof of claim 1 or 17.

21. A method of treating a viral infection caused by Hepatitis C virus comprising administering to a mammal in need thereof a therapeutically effective amount of a compound or pharmaceutically acceptable salt or ester thereof or pharmaceutical composition of claim 1 or 17.

22. The method of claim 21 further comprising administering at least one additional therapeutic agent selected from the group consisting of interferons, ribavirin or its analogs, HCV NS3 protease inhibitors, NS5a inhibitors, alpha-glucosidase 1 inhibitors, hepatoprotectants, mevalonate decarboxylase antagonists, antagonists of the renin-angiotensin system, other anti-fibrotic agents, nucleoside or nucleotide inhibitors of HCV NS5B polymerase, non-nucleoside inhibitors of HCV NS5B polymerase, HCV NS5A inhibitors, TLR-7 agonists, cyclophillin inhibitors, HCV IRES inhibitors, pharmacokinetic enhancers, and other drugs for treating HCV.

* * * * *